(12) United States Patent
LaCrampe et al.

(10) Patent No.: US 7,241,763 B2
(45) Date of Patent: Jul. 10, 2007

(54) 3-FURANYL ANALOGS OF TOXOFLAVINE AS KINASE INHIBITORS

(75) Inventors: Jean Fernand Armand LaCrampe, Le Mesnil-Esnard (FR); Richard William Connors, Harleysville, PA (US); Chih Yung Ho, Drinnon Way, PA (US); Alan Richardson, Buckingham (GB); Eddy Jean Edgard Freyne, Rumst (BE); Peter Jacobus Johannes Buijnsters, JX Breda (NL); Annette Cornelia Bakker, Borgerhout (BE)

(73) Assignee: Janssen Pharmaceutica N.V. (BE)

( * ) Notice: Subject to any disclaimer, the term of this patent is extended or adjusted under 35 U.S.C. 154(b) by 171 days.

(21) Appl. No.: 10/520,641

(22) PCT Filed: Jul. 8, 2003

(86) PCT No.: PCT/EP03/50293

§ 371 (c)(1),
(2), (4) Date: Jan. 7, 2005

(87) PCT Pub. No.: WO2004/007499

PCT Pub. Date: Jan. 22, 2004

(65) Prior Publication Data

US 2006/0040943 A1    Feb. 23, 2006

(30) Foreign Application Priority Data

Jul. 15, 2002  (EP)  .................. 02077822

(51) Int. Cl.
| C07D 407/04 | (2006.01) |
| C07D 487/04 | (2006.01) |
| A61K 31/53 | (2006.01) |
| A61P 35/00 | (2006.01) |
| A61P 19/02 | (2006.01) |

(52) U.S. Cl. ...................... 514/243; 544/184
(58) Field of Classification Search ................ 544/184; 514/243
See application file for complete search history.

(56) References Cited

U.S. PATENT DOCUMENTS 4,568,649 A   2/1986   Bertoglio-Matte

FOREIGN PATENT DOCUMENTS

| GB | 2039883 A | 8/1980 |
| JP | 09-255681 A2 | 9/1997 |
| WO | WO 02/02552 A1 | 1/2002 |
| WO | WO 02/20525 A2 | 3/2002 |
| WO | WO 02/20525 A3 | 3/2002 |

OTHER PUBLICATIONS

Meijer L., et al., "Chemical Inhibitors of Cyclin-Dependent Kinases", Progress in Cell Cycle Research, vol. 1, 351-363, 1995.
Kaur, et al., "Growth Inhibition With Reversible Cell Cycle Arrest of Carcinoma Cells by Flavone L86-8275", J. Natl. Cancer Inst., vol. 84(22), 1736-1740, 1992.
Sedlacek, et al., "Flavopiridol (L86 8275; NSC 649890), a new kinase inhibitor for tumor therapy", Int. J. Oncol, vol. 9:1143-1168, 1996.
Vesely, et al., "Inhibition of cyclin-dependent kinases by purine analogues", Eur. J. Biochem, 224, 771-786, 1994.
Gennaro, et al., "Remington's Pharmaceutical Sciences", 18th edition, Mack Publishing Company, 1990 book cover & table of contents.
Nagamatsu, et al., "General syntheses of 1-alkyltoxoflavin and 8-alkylfervenulin derivatives of biological significance by the regioselective alkylation of reumycin derivatives and the rates of transalkylation from 1-alkyltoxoflavins into nucleophiles", J. Chem. Soc., Perkin Trans. 1, 130-137, 2001.
Nagamatsu, et al., "Syntheses of 3-Substituted 1-Methyl-6-phenylpyrimido[5,4-e]-1,2,4-triazine-5,7(1H,6H)-diones (6-Phenyl Analogs of Toxoflavin) and Their 4-Oxides, and Evaluation of Antimicrobial Activity of Toxoflavins and Their Analogs",, Chem. Pharm. Bull 41(2) 362-368, 1993.
Wiley & Sons, Inc., "Fused Pyrimidines Miscellaneous Fused Pyrimidines", Heterocyclic Compounds, vol. 24 (part 4) p. 261-304.
International Search Report mailed Oct. 23, 2003 for PCT/EP03/50293.

*Primary Examiner*—Venkataraman Balasubramanian
(74) *Attorney, Agent, or Firm*—Alana G. Kreigsman

(57) ABSTRACT

The present invention concerns the compounds of formula

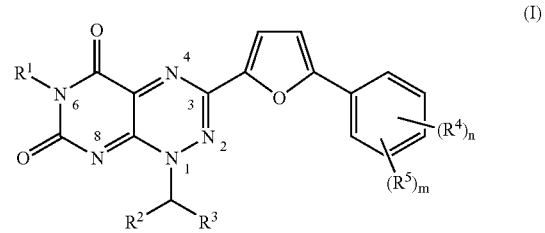

(I)

the N-oxide forms, the pharmaceutically acceptable addition salts and the stereochemically isomeric forms thereof, wherein m, n, $R^1$, $R^2$, $R^3$, $R^4$ and $R^5$ are as defined herein, the use of such compounds as inhibitors of cyclin-dependent serine/threonine kinases (Cdks), as well as kinases and phosphatases involved in cell cycle regulation such as the tyrosine kinases Wee1, Mik1 and Myt1 or the tyrosine dephosphatases such as Cdc25 and Pyp3. The present invention is further directed to pharmaceutical compositions comprising the compounds of the present invention and to methods for treating cell proliferative disorders such as atherosclerosis, restenosis and cancer.

17 Claims, No Drawings

3-FURANYL ANALOGS OF TOXOFLAVINE AS KINASE INHIBITORS

CROSS REFERENCE TO RELATED APPLICATIONS

This application is the national stage of Application No. PCT/EP03/50293, filed Jul. 8, 2003 which application claims priority from European Patent No. 02077822.1, filed Jul. 15, 2002.

This invention relates to 1H-pyrimido[5.4-e][1,2,4]triazine-5,7-dione derivatives that inhibit cyclin-dependent serine/threonine kinases (Cdks), as well as kinases and phosphatases involved in cell cycle regulation such as the tyrosine kinases Wee1, Mik1 and Myt1 or the tyrosine dephosphatases such as Cdc25 and Pyp3. Cyclin-dependent kinases belong to the main regulators of cell division in eukaryotic organisms and their deregulation results in rearrangements, amplification and loss of chromosomes, events that are causally associated with cancer. As such these compounds are useful to treat cell proliferative disorders such as atherosclerosis, restenosis and cancer.

FIELD OF THE INVENTION

1. Background of the Invention

Cell cycle kinases are naturally occurring enzymes involved in regulation of the cell cycle (Meijer L., "Chemical Inhibitors of Cyclin-Dependent Kinases", *Progress in Cell Cycle Research,* 1995; 1:35 1–363). Typical enzymes include serine/threonine kinases such as the cyclin-dependent kinases (cdk) cdk1, cdk2, cdk4, cdk5, cdk6 as well as tyrosine kinases such as AKT3 or Wee 1 kinase and tyrosine phosphatases such as cdc25 involved in cell cycle regulation. Increased activity or temporally abnormal activation or regulation of these kinases has been shown to result in development of human tumors and other proliferative disorders. Compounds that inhibit cdks, either by blocking the interaction between a cyclin and its kinase partner, or by binding to and inactivating the kinase, cause inhibition of cell proliferation, and are thus useful for treating tumors or other abnormally proliferating cells.

Several compounds that inhibit cdks have demonstrated preclinical anti-tumor activity. For example, flavopiridol is a flavonoid that has been shown to be a potent inhibitor of several types of breast and lung cancer cells (Kaur, et al., *J. Natl. Cancer Inst.,* 1992; 84:1736–1740; *Int. J. Oncol.,* 1996; 9:1143–1168). The compound has been shown to inhibit cdk2 and cdk4. Olomoucine [2-(hydroxyethylamino)-6-benzylamine-9-methylpurine] is a potent inhibitor of cdk2 and cdk5 (Vesely, et al., *Eur. J. Biochem.,* 1994; 224:77 1–786), and has been shown to inhibit proliferation of approximately 60 different human tumor cell lines used by the National Cancer Institute (NCI) to screen for new cancer therapies (Abraham, et al., *Biology of the Cell,* 1995; 83: 105–120). More recently, flavonoid derivatives such toxoflavine (J. Chem. Soc. Perkin Trans. 1, 2001, 130–137) and 7-azapteridine derivatives (Japanese Unexamined Patent Application Laid Open H9-255681) have been disclosed as antineoplastic agents.

2. Detailed Description of the Invention

The toxoflavine derivatives of the present invention differ thereof in that the substituent at position 3 is furanyl which is further substituted with water solubility enhancing functionalities such as alcohol groups, aliphatic basic amine entities and aminosulphon(amine) substituents or a combination thereof, without loss of biological activity as anti-proliferative compounds.

Accordingly, the underlying problem to be solved by the present invention was to find further toxoflavine derivatives with an improved water solubility and concomitant cellular activity.

This invention concerns compounds of formula (I)

(I)

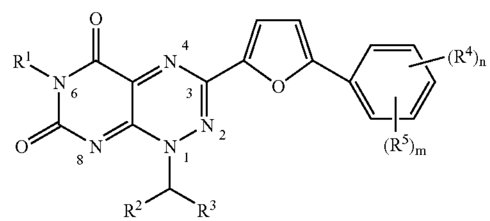

the N-oxide forms, the pharmaceutically acceptable addition salts and the stereochemically isomeric forms thereof, wherein m represents an integer being 0 or 1;

n represents an integer being 0, 1 or 2;

$R^1$ represents hydrogen, $C_{1-4}$alkyl, hydroxy$C_{1-4}$alkyl, $C_{1-4}$alkyloxycarbonyl or $C_{1-4}$alkyl substituted with phenyl, pyridinyl or morpholinyl,
- phenyl or phenyl substituted with one or where possible more substituents each independently being selected from $C_{1-4}$alkyl, $C_{1-4}$alkyloxycarbonyl, —$NO_2$ or cyano-$C_{1-4}$alkyl,
- piperidinyl or piperidinyl substituted with one or where possible more substituents each independently being selected from $C_{1-4}$alkyl, $C_{1-4}$alkyloxycarbonyl or phenyl-$C_{1-4}$alkyl,
- phenyl-$C_{1-4}$alkyl or $C_{1-4}$alkyloxycarbonyl;

$R^2$ represents hydrogen, phenyl, $C_{1-4}$alkyl or $C_{1-4}$alkyl substituted with phenyl or hydroxy;

$R^3$ represents hydrogen, phenyl, $C_{1-4}$alkyl or $C_{1-4}$alkyl substituted with phenyl or hydroxy; or $R^2$ and $R^3$ taken together with the carbon atom to which they are attached form a $C_{3-8}$cycloalkyl or $Het^1$ wherein said $C_{3-8}$cycloalkyl or $Het^1$ each independently may optionally be substituted with one, or where possible, two or three substituents each independently selected from $C_{1-4}$alkyloxycarbonyl, phenylcarbonyl $C_{1-4}$alkylsulfonyl, aminosulfonyl, mono- or di($C_{1-4}$alkyl)aminosulfonyl or —C(═NH)—$NH_2$;

$R^4$ represents halo, hydroxy, hydroxy$C_{1-4}$alkyl or $C_{1-4}$alkyloxy;

$R^5$ represents formyl, $C_{1-4}$alkyl, $C_{1-4}$alkyloxy, $Het^2$, —$NO_2$, —$SO_2$-$Het^6$, aminosulfonyl, —$SO_2$—$NR^{12}R^{13}$,
- $C_{1-4}$alkyl substituted with one or where possible more substituent being selected from hydroxy, halo, $Het^3$, $NR^6R^7$ or formyl,
- $C_{1-4}$alkyloxy substituted with one or where possible more substituents being selected from $Het^4$, $NR^8R^9$ or —C(═O)-$Het^4$;

$R^6$ and $R^7$ are each independently selected from hydrogen, $C_{1-4}$alkyl, -$Het^5$, aminosulphonyl, mono- or di($C_{1-4}$alkyl) aminosulfonyl, $C_{1-4}$alkylsulfonyl, $C_{1-4}$alkyloxycarbonyl, $C_{1-4}$alkyloxy$C_{1-4}$alkyl, methoxy$C_{1-4}$alkyl or $C_{1-4}$alkyl substituted with one or where possible more substituents being selected from hydroxy, $Het^5$, $C_{1-4}$alkyloxycarbonyl or $C_{1-4}$alkylsulfonyl;

$R^8$ and $R^9$ are each independently selected from hydrogen, mono- or di($C_{1-4}$alkyl)aminosulphonyl or aminosulphonyl;

$R^{12}$ and $R^{13}$ are each independently selected from hydrogen, $C_{1-4}$alkyl, $C_{1-4}$alkyloxy$C_{1-4}$alkyl;

$Het^1$ represents piperidinyl;

$Het^2$ represents a heterocycle selected from piperidinyl, or piperazinyl wherein said monocyclic heterocycles each independently may optionally be substituted with one, or where possible two or three substituents each independently selected from $C_{1-4}$alkyloxycarbonyl;

$Het^3$ represents a heterocycle selected from morpholinyl, pyrrolidinyl, piperidinyl, or piperazinyl wherein said monocyclic heterocycles each independently may optionally be substituted with one, or where possible two or three substituents each independently selected from hydroxy, $C_{1-4}$alkyl, $C_{1-4}$alkyloxycarbonyl, hydroxy$C_{1-4}$alkyl, aminosulfonyl, mono- or di($C_{1-4}$alkyl)aminosulfonyl, $NR^{10}R^{11}$, imidazolyl, tetrahydropyrimidinyl, amino, $NH_2$—$SO_2$—O—, mono- or di($C_{1-4}$alkyl)amino-$SO_2$—O—, $NH_2$—$SO_2$—NH—,
mono- or di($C_{1-4}$alkyl)amino-$SO_2$—NH—, hydroxy$C_{1-4}$alkyloxy$C_{1-4}$alkyl, $C_{1-4}$alkyloxy$C_{1-4}$alkyl or $C_{1-4}$alkyloxy;

$R^{10}$ and $R^{11}$ are each independently selected from hydrogen, $C_{1-4}$alkyl, $C_{1-4}$alkyloxycarbonyl, or mono- or di($C_{1-4}$alkyl)aminosulfonyl;

$Het^4$ represents a heterocycle selected from morpholinyl, piperidinyl or piperazinyl wherein said monocyclic heterocycles each independently may optionally be substituted with one, or where possible two or three substituents each independently selected from $C_{1-4}$alkyl, aminosulphonyl, mono- or di($C_{1-4}$alkyl)aminosulfonyl or $C_{1-4}$alkyl substituted with one or more hydroxy;

$Het^5$ represents a heterocycle selected from pyridinyl, pyrrolidinyl, or piperidinyl wherein said monocyclic heterocycles each independently may optionally be substituted with one, or where possible two or three substituents each independently selected from $C_{1-4}$alkyl, aminosulfonyl, $C_{1-4}$alkyloxycarbonyl or mono- or di($C_{1-4}$alkyl)aminosulfonyl;

$Het^6$ represents morpholinyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{3-8}$cycloalkyl is generic to cyclopropyl, cyclobutyl, cyclopentyl, cycloheptyl and cyclo-octanyl; $C_{1-4}$alkyloxy defines straight or branched saturated hydrocarbon radicals such as methoxy, ethoxy, propyloxy, butyloxy, 1-methylethyloxy, 2-methylpropyloxy and the like.

As used herein before, the term (=O) forms a carbonyl moiety with the carbon atom to which it is attached. The term (=NH) forms a imino moiety with the carbon atom to which it is attached. The term formyl as used herein before refers to a radical of fomula —CH(=O).

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I) are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein the azapteridine-nitrogen is N-oxidized.

A preferred group of compounds consists of those compounds of formula (I) wherein one or more of the following restrictions apply:

$R^1$ represents $C_{1-4}$alkyl preferably methyl, piperidinyl or piperidinyl substituted with phenyl-$C_{1-4}$alkyl or $C_{1-4}$alkyloxycarbonyl;

$R^2$ represents hydrogen, phenyl, $C_{1-4}$alkyl or $C_{1-4}$alkyl substituted with phenyl;

$R^2$ represents hydrogen, phenyl, $C_{1-4}$alkyl or $C_{1-4}$alkyl substituted with phenyl; or $R^2$ and $R^3$ taken together with the carbon atom to which they are attached form cyclopentyl or piperidinyl wherein said cyclopentyl or piperidinyl each independently may optionally be substituted with one, or where possible, two or three substituents each independently selected from $C_{1-4}$alkyloxycarbonyl, $C_{1-4}$alkylsulfonyl, aminosulfonyl, mono- or di($C_{1-4}$alkyl)aminosulfonyl or phenylcarbonyl;

$R^4$ represents halo, preferably Cl or $R^4$ represents $C_{1-4}$alkyloxy;

$R^5$ represents formyl, —$SO_2$-$Het^6$, $C_{1-4}$alkyl substituted with one or where possible more substituent being selected from hydroxy, $Het^3$, $NR^6R^7$ or formyl, or $R^5$ represents $C_{1-4}$alkyloxy substituted with one or where possible more substituents being selected from $Het^4$ or —C(=O)-$Het^4$;

$R^6$ and $R^7$ are each independently selected from hydrogen, $C_{1-4}$alkyl, $Het^5$, $C_{1-4}$alkylsulfonyl, $C_{1-4}$alkyloxy$C_{1-4}$alkyl, or $C_{1-4}$alkyl substituted with one or where possible more substituents being selected from hydroxy or $Het^5$;

Het³ represents a heterocycle selected from morpholinyl, pyrrolidinyl, piperidinyl, or piperazinyl wherein said monocyclic heterocycles each independently may optionally be substituted with one, or where possible two or three substituents each independently selected from hydroxy, $C_{1-4}$alkyl, $C_{1-4}$alkyloxycarbonyl, hydroxy$C_{1-4}$alkyl, aminosulfonyl, mono- or di($C_{1-4}$alkyl)aminosulfonyl, NR¹⁰R¹¹, imidazolyl, tetrahydropyrimidinyl, amino, mono- or di($C_{1-4}$alkyl)amino-SO₂—NH—, hydroxy$C_{1-4}$alkyloxy$C_{1-4}$alkyl, $C_{1-4}$alkyloxy$C_{1-4}$alkyl or $C_{1-4}$alkyloxy;

R¹⁰ and R¹¹ are each independently selected from hydrogen or $C_{1-4}$alkyl;

Het⁴ represents a heterocycle selected from morpholinyl or piperazinyl wherein said monocyclic heterocycles each independently may optionally be substituted with one, or where possible two or three $C_{1-4}$alkyl substituents, preferably methyl;

Het⁵ represents a heterocycle selected from pyridinyl, pyrrolidinyl or piperidinyl wherein said monocyclic heterocycles each independently may optionally be substituted with one, or where possible two or three substituents each independently selected from $C_{1-4}$alkyl, aminosulfonyl, $C_{1-4}$alkyloxycarbonyl or mono- or di($C_{1-4}$alkyl)aminosulfonyl.

A group of interesting compounds consists of those compounds of formula (I) wherein one or more of the following restrictions apply:

R¹ represents $C_{1-4}$alkyl preferably methyl, $C_{1-4}$alkyl substituted with pyridinyl, phenyl, piperidinyl or piperidinyl substituted with $C_{1-4}$alkyloxycarbonyl;

R² represents hydrogen or $C_{1-4}$alkyl preferably methyl;

R³ represents hydrogen or $C_{1-4}$alkyl preferably methyl; or

R² and R³ taken together with the carbon atom to which they are attached form cyclopentyl or piperidinyl wherein said cyclopentyl or piperidinyl each independently may optionally be substituted with one, or where possible, two or three substituents each independently selected from $C_{1-4}$alkyloxycarbonyl, phenylcarbonyl or —C(=NH)—NH₂;

R⁴ represents halo or $C_{1-4}$alkyloxy;

R⁵ represents Het², $C_{1-4}$alkyl substituted with one or where possible more substituents being selected from hydroxy, halo, Het³ or NR⁶R⁷, or R⁵ represents $C_{1-4}$alkyloxy substituted with one or where possible more substituents being selected from Het⁴ or —C(=O)-Het⁴;

R⁶ and R⁷ are each independently selected from hydrogen, $C_{1-4}$alkyl, Het⁵ or $C_{1-4}$alkyl substituted with one or where possible more substituents being selected from hydroxy or Het⁵;

Het² represents piperazinyl;

Het³ represents a heterocycle selected from morpholinyl, pyrrolidinyl, piperidinyl, or piperazinyl wherein said monocyclic heterocycles each independently may optionally be substituted with one, or where possible two or three substituents each independently selected from $C_{1-4}$alkyl preferably methyl, aminosulfonyl, mono- or di($C_{1-4}$alkyl)aminosulfonyl, hydroxy$C_{1-4}$alkyloxy$C_{1-4}$alkyl, $C_{1-4}$alkyloxy$C_{1-4}$alkyl or $C_{1-4}$alkyloxy;

Het⁴ represents a heterocycle selected from morpholinyl or piperazinyl wherein said monocyclic heterocycles each independently may optionally be substituted with one, or where possible two or three $C_{1-4}$alkyl substituents, preferably methyl;

Het⁵ represents a heterocycle selected from pyridinyl, pyrrolidinyl or piperidinyl wherein said monocyclic heterocycles each independently may optionally be substituted with one, or where possible two or three substituents each independently selected from aminosulfonyl, $C_{1-4}$alkyloxycarbonyl or mono- or di($C_{1-4}$alkyl)aminosulfonyl.

A further group of interesting compounds consists of those compounds of formula (I) wherein one or more of the following restrictions apply:

R¹ represents $C_{1-4}$alkyl, piperidinyl, or piperidinyl substituted with $C_{1-4}$alkyloxycarbonyl preferably t-butyloxycarbonyl;

R² represents $C_{1-4}$alkyl preferably methyl;

R³ represents $C_{1-4}$alkyl preferably methyl; or

R² and R³ taken together with the carbon atom to which they are attached form cyclopentyl or piperidinyl wherein said cyclopentyl or piperidinyl each independently may optionally be substituted with one, or where possible, two or three substituents each independently selected from $C_{1-4}$alkyloxycarbonyl, phenylcarbonyl or —C(=NH)—NH₂;

R⁴ represents halo or $C_{1-4}$alkyloxy;

R⁵ represents Het², $C_{1-4}$alkyl substituted with one or where possible more substituents being selected from hydroxy, Het³ or NR⁶R⁷, or R⁵ represents $C_{1-4}$alkyloxy substituted with one or where possible more substituents being selected from Het⁴ or —C(=O)-Het⁴;

R⁶ and R⁷ are each independently selected from hydrogen, $C_{1-4}$alkyl, -Het⁵ or $C_{1-4}$alkyl substituted with one or where possible more substituents being selected from hydroxy or Het⁵;

Het² represents piperazinyl;

Het³ represents a heterocycle selected from morpholinyl, pyrrolidinyl, or piperazinyl wherein said monocyclic heterocycles each independently may optionally be substituted with one, or where possible two or three substituents each independently selected from $C_{1-4}$alkyl preferably methyl, aminosulfonyl, mono- or di($C_{1-4}$alkyl)aminosulfonyl, hydroxy$C_{1-4}$alkyloxy$C_{1-4}$alkyl, $C_{1-4}$alkyloxy$C_{1-4}$alkyl or $C_{1-4}$alkyloxy;

Het⁴ represents a heterocycle selected from morpholinyl or piperazinyl wherein said monocyclic heterocycles each independently may optionally be substituted with one, or where possible two or three $C_{1-4}$alkyl substituents, preferably methyl;

Het⁵ represents a heterocycle selected from pyridinyl, pyrrolidinyl or piperidinyl wherein said monocyclic heterocycles each independently may optionally be substituted with one, or where possible two or three substituents each independently selected from aminosulfonyl, $C_{1-4}$alkyloxycarbonyl or mono- or di($C_{1-4}$alkyl)aminosulfonyl.

Also of interest, are the group of compounds of formula (I) wherein one or more of the following restrictions apply:

R¹ represents $C_{1-4}$alkyl preferably methyl

R² represents hydrogen, $C_{1-4}$alkyl or phenyl;

R³ represents hydrogen, $C_{1-4}$alkyl or phenyl; or

R² and R³ taken together with the carbon atom to which they are attached form cyclopentyl or piperidinyl wherein said cyclopentyl or piperidinyl may optionally be substituted with one, or where possible, two or three substituents each independently selected from $C_{1-4}$alkyloxycarbonyl preferably t-butyloxycarbonyl or aminosulfonyl;

R⁴ represents halo, preferably Cl or Br or R⁴ represents $C_{1-4}$alkyloxy preferably methoxy;

R⁵ represents $C_{1-4}$alkyl substituted with one or where possible more substituent being selected from hydroxy, Het³ or NR⁶R⁷, or R⁵ represents $C_{1-4}$alkyloxy substituted with one or where possible more substituents being selected from Het⁴ or —C(=O)-Het⁴;

$R^6$ and $R^7$ are each independently selected from hydrogen, $C_{1-4}$alkyl, -Het$^5$, $C_{1-4}$alkylsulfonyl, $C_{1-4}$alkyloxy$C_{1-4}$alkyl, or $C_{1-4}$alkyl substituted with one or where possible more substituents being selected from hydroxy or Het$^5$;

Het$^3$ represents a heterocycle selected from morpholinyl, piperidinyl, or piperazinyl wherein said monocyclic heterocycles each independently may optionally be substituted with one, or where possible two or three substituents each independently selected from hydroxy, $C_{1-4}$alkyl, hydroxy$C_{1-4}$alkyl, mono- or di($C_{1-4}$alkyl)aminosulfonyl, aminosulfonyl, NR$^{10}$R$^{11}$, imidazolyl, amino, hydroxy$C_{1-4}$alkyloxy$C_{1-4}$alkyl, $C_4$alkyloxy$C_{1-4}$alkyl or $C_{1-4}$alkyloxy;

$R^{10}$ and $R^{11}$ are each independently selected from hydrogen or $C_{1-4}$alkyl;

Het$^4$ represents morpholinyl;

Het$^5$ represents a heterocycle selected from pyridinyl, or piperidinyl wherein said monocyclic heterocycles each independently may optionally be substituted with one, or where possible two or three substituents each independently selected from aminosulfonyl or mono- or di($C_{1-4}$alkyl)aminosulfonyl.

A remarkable group of compounds are those according to formula (I) wherein one or more of the following restrictions apply;

n represents an integer being 0, 1 or 2;

$R^1$ represents $C_{1-4}$alkyl, preferably methyl or $R^1$ represents phenyl, phenyl substituted with $C_{1-4}$alkyloxycarbonyl or —NO$_2$, or $R^1$ represents $C_{1-4}$alkyl substituted with pyridinyl or morpholinyl;

$R^2$ represents hydrogen, or $C_{1-4}$alkyl preferably methyl;

$R^3$ represents hydrogen, phenyl or $C_{1-4}$alkyl preferably methyl;

$R^4$ represents halo preferably Cl;

$R^5$ represents $C_{1-4}$alkyl substituted with one or where possible more halo substituents preferably said halo substituted $C_{1-4}$alkyl being trifluoromethyl.

It is also an embodiment of the present invention to provide a group of compounds of formula (I) wherein one or more of the following restrictions apply;

$R^1$ represents $C_{1-4}$alkyl preferably methyl, $C_{1-4}$alkyl substituted with phenyl, or $R^1$ represents piperidinyl or piperidinyl substituted with $C_{1-4}$alkyloxycarbonyl;

$R^2$ represents hydrogen, phenyl, $C_{1-4}$alkyl or $C_{1-4}$alkyl substituted with phenyl;

$R^2$ represents hydrogen, phenyl, $C_{1-4}$alkyl or $C_{1-4}$alkyl substituted with phenyl; or $R^2$ and $R^3$ taken together with the carbon atom to which they are attached form cyclopentyl or piperidinyl wherein said cyclopentyl or piperidinyl each independently may optionally be substituted with one, or where possible, two or three substituents each independently selected from $C_{1-4}$alkyloxycarbonyl, $C_{1-4}$alkylsulfonyl, mono- or di($C_{1-4}$alkyl)aminosulfonyl or phenylcarbonyl;

$R^4$ represents halo, preferably Cl or $R^4$ represents $C_{1-4}$alkyloxy preferably methoxy;

$R^5$ represents formyl, $C_{1-4}$alkyl substituted with one or where possible more substituent being selected from hydroxy, Het$^3$ or NR$^6$R$^7$, or $R^5$ represents $C_{1-4}$alkyloxy substituted with one or where possible more substituents being selected from Het$^4$ or —C(=O)-Het$^4$;

$R^6$ and $R^7$ are each independently selected from hydrogen, $C_{1-4}$alkyl, -Het$^5$, $C_{1-4}$alkylsulfonyl, methoxy$C_{1-4}$alkyl, or $C_{1-4}$alkyl substituted with one or where possible more substituents being selected from hydroxy or Het$^5$;

Het$^2$ represents piperidinyl optionally substituted with $C_{1-4}$alkyloxycarbonyl;

Het$^3$ represents a heterocycle selected from morpholinyl, pyrrolidinyl, piperidinyl, or piperazinyl wherein said monocyclic heterocycles each independently may optionally be substituted with one, or where possible two or three substituents each independently selected from hydroxy, $C_{1-4}$alkyl, $C_{1-4}$alkyloxycarbonyl, hydroxy$C_{1-4}$alkyl, aminosulfonyl, mono- or di($C_{1-4}$alkyl)aminosulfonyl, NR$^{10}$R$^{11}$, imidazolyl, tetrahydropyrimidinyl, amino, hydroxy$C_{1-4}$alkyloxy$C_{1-4}$alkyl, $C_{1-4}$alkyloxy$C_{1-4}$alkyl or $C_{1-4}$alkyloxy;

$R^{10}$ and $R^{11}$ are each independently selected from hydrogen or $C_{1-4}$alkyl;

Het$^4$ represents a heterocycle selected from morpholinyl or piperazinyl wherein said monocyclic heterocycles each independently may optionally be substituted with one, or where possible two or three $C_{1-4}$alkyl substituents, preferably methyl;

Het$^5$ represents a heterocycle selected from pyridinyl, pyrrolidinyl or piperidinyl wherein said monocyclic heterocycles each independently may optionally be substituted with one, or where possible two or three substituents each independently selected from $C_{1-4}$alkyl, aminosulfonyl, $C_{1-4}$alkyloxycarbonyl or mono- or di($C_{1-4}$alkyl)aminosulfonyl.

It is also an embodiment of the present invention to provide a group of compounds of formula (I) wherein one or more of the following restrictions apply;

$R^1$ represents hydrogen, $C_{1-4}$alkyl, hydroxy$C_{1-4}$alkyl, $C_{1-4}$alkyloxycarbonyl or $C_{1-4}$alkyl substituted with pyridinyl or morpholinyl, phenyl or phenyl substituted with one or where possible more substituents each independently being selected from —NO$_2$ or cyano-$C_{1-4}$alkyl, piperidinyl or piperidinyl substituted with phenyl-$C_{1-4}$alkyl preferably benzyl, or $C_{1-4}$alkyloxycarbonyl;

$R^2$ represents hydrogen, phenyl or $C_{1-4}$alkyl preferably methyl or isopropyl;

$R^3$ represents hydrogen, phenyl, $C_{1-4}$alkyl or benzyl;

$R^4$ represents halo, hydroxy, hydroxy $C_{1-4}$alkyl or $C_{1-4}$alkyloxy;

$R^5$ represents formyl, Het$^2$, —SO$_2$-Het$^6$, $C_{1-4}$alkyl substituted with one or where possible more substituent being selected from hydroxy, halo, Het$^3$, NR$^6$R$^7$ or formyl, $C_{1-4}$alkyloxy substituted with one or where possible more substituents being selected from Het$^4$ or —C(=O)-Het$^4$;

$R^6$ and $R^7$ are each independently selected from hydrogen, $C_{1-4}$alkyl, -Het$^5$, mono- or di($C_{1-4}$alkyl)aminosulfonyl, $C_{1-4}$alkylsulfonyl, $C_{1-4}$alkyloxycarbonyl or $C_{1-4}$alkyl substituted with one or where possible more substituents being selected from hydroxy or Het$^5$;

Het$^3$ represents a heterocycle selected from morpholinyl, piperidinyl, or piperazinyl wherein said monocyclic heterocycles each independently may optionally be substituted with one, or where possible two or three substituents each independently selected from hydroxy, $C_{1-4}$alkyl, $C_{1-4}$alkyloxycarbonyl, mono- or di($C_{1-4}$alkyl)aminosulfonyl, NR$^{10}$R$^{11}$, hydroxy$C_{1-4}$alkyloxy$C_{1-4}$alkyl, $C_{1-4}$alkyloxy$C_{1-4}$alkyl or $C_{1-4}$alkyloxy;

$R^{10}$ and $R^{11}$ are each independently selected from hydrogen or mono- or di($C_{1-4}$alkyl)aminosulfonyl;

Het$^4$ represents a heterocycle selected from morpholinyl, piperidinyl or piperazinyl wherein said monocyclic heterocycles each independently may optionally be substituted with one, or where possible two or three substituents each independently selected from $C_{1-4}$alkyl, aminosulphonyl or mono- or di($C_{1-4}$alkyl)aminosulfonyl;

Het$^5$ represents a heterocycle selected from pyridinyl or piperidinyl wherein said monocyclic heterocycles each independently may optionally be substituted with one, or where possible two or three substituents each independently selected from $C_{1-4}$alkyloxycarbonyl or mono- or di($C_{1-4}$alkyl)aminosulfonyl;

Other special group of compounds are;

those compounds of formula (I) wherein $R^1$ is methyl;

those compounds of formula (I) wherein $R^2$ and $R^3$ taken together with the carbon atom to which they are attached form a $C_{3-8}$cycloalkyl, preferably $C_{5-8}$cycloalkyl, more preferably a cyclopentyl;

those compounds of formula (I) wherein $R^2$ and $R^3$ each represents a $C_{1-4}$alkyl, preferably methyl;

those compounds of formula (I) wherein Het$^3$ represent a heterocycle selected from the group consisting of morpholinyl, piperidinyl, piperazinyl and piperazinyl substituted with one $C_{1-4}$alkyl substituent, preferably methyl, more preferably with the methyl in the para position relative to the carbon atom bearing the $R^5$ substituent.

those compounds of formula (I) with $R^5$ being a $C_{1-4}$alkyloxy said $C_{1-4}$alkyloxy being substituted with either;

one Het$^4$ substituent with Het$^4$ being selected from the group consisting of morpholinyl, piperidinyl, piperazinyl and piperazinyl substituted with one $C_{1-4}$alkyl substituent, preferably methyl, more preferably with the methyl in the para position relative to the carbon atom bearing the $R^5$ substituent, or one —C(=O)-Het$^4$ substituent with Het$^4$ being piperazinyl preferably substituted with $C_{1-4}$alkyl, more preferably substituted with methyl.

those compounds of formula (I) wherein $R^6$ or $R^7$ each represent Het$^5$ with said Het$^5$ being selected from the group consisting of piperidinyl, piperidinyl substituted with aminosulfonyl or mono- or di($C_{1-4}$alkyl)aminosulfonyl, preferably dimethylaminosulfonyl, and pyrolidinyl optionally substituted $C_{1-4}$alkyloxycarbonyl, preferably ethoxycarbonyl.

those compounds of formula (I) wherein $R^6$ or $R^7$ represent $C_{1-4}$alkyl substituted with Het$^5$ said Het$^5$ being selected from pyridinyl.

those compounds of formula (I) wherein m represents 0 and $R^4$ represents halo, preferably chloro.

In order to simplify the structural representation of the compounds of formula (I), the group

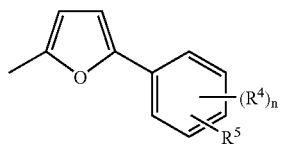

will hereinafter be represented by the symbol Q.

The compounds of this invention can be prepared by any of several standard synthetic processes commonly used by those skilled in the art of organic chemistry and described for instance in the following references; "Heterocyclic Compounds"—Vol. 24 (part4) p 261–304 Fused pyrimidines, Wiley—Interscience; Chem. Pharm. Bull., Vol 41(2) 362–368 (1993); J. Chem. Soc., Perkin Trans. 1, 2001, 130–137.

As further exemplified in the experimental part of the description, the compounds of formula (I) were generally prepared using three alternative synthesis schemes. In a first alternative, the compounds of formula (I) were prepared by nitrosative cyclisation of intermediates of formula (II) with NaNO$_2$ in acetic acid (AcOH). The thus obtained azapteridines comprising the 5-nitroso intermediates of formula (III) are subsequently converted in the final compounds with formula (I) by refluxing the mixture in for example acetic anhydride or ethanol (EtOH) comprising dithiothreitol (DTT).

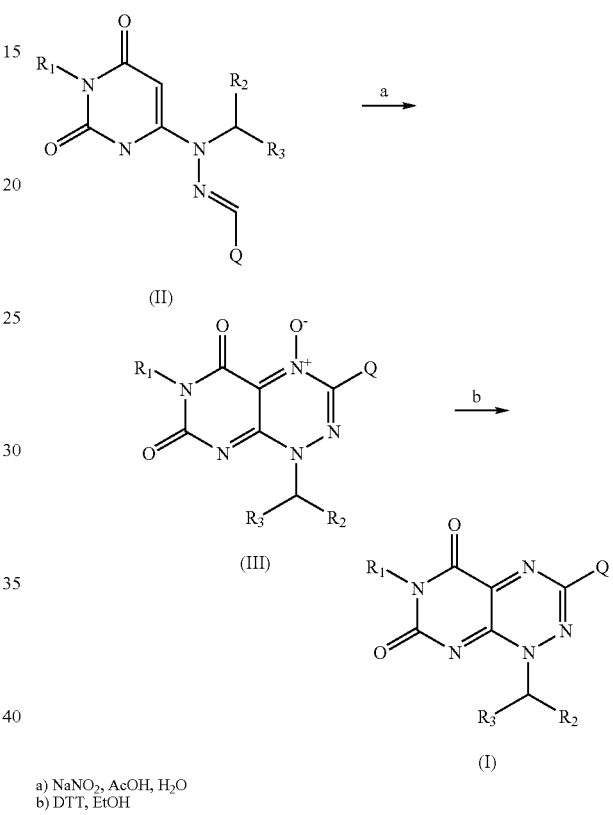

a) NaNO$_2$, AcOH, H$_2$O
b) DTT, EtOH

Alternatively, the intermediates of formula (III) are dealkylated by heating in N,N-Dimethylformamide (DMF) at temperatures ranging from 90–150° C. for 3–6 hours. The thus obtained reumycin derivatives of formula (IV) are subsequently alkylated in 1,4-dioxane further comprising an appropriate base such as anhydrous potassium carbonate, sodium hydride or sodium hydrogen carbonate, preferably anhydrous potassium carbonate and an alkylating agent such as dialkylsulfate, alkyliodide or alkylbromide, preferably alkylbromide, yielding the final compounds of formula (I).

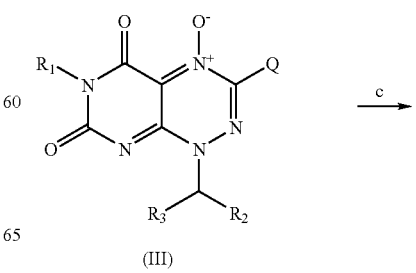

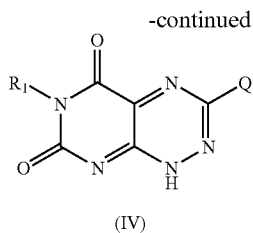

(IV)

c) DMF, 90° C.
d) K₂CO₃, 1,4-Dioxane, 120° C.,

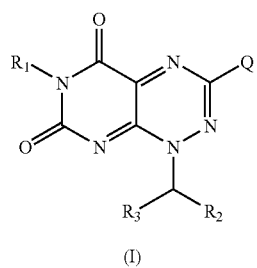

(I)

In the aforementioned reaction schemes, the substituted imines or Schiff's bases of formula (II) can generally be prepared by reacting a primary amine of formula (V) with an aldehyde of formula (VI) in a traditional condensation reaction using amongst others ethanol as a suitable solvent.

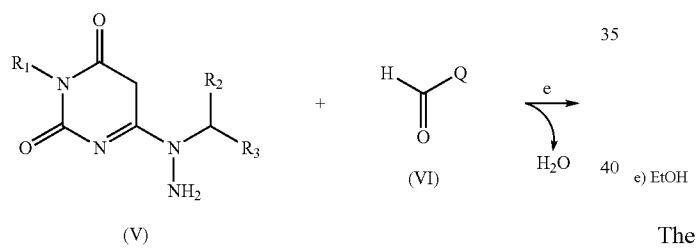

(II)

Finally, as an alternative to the above, the compounds of formula (I) can be prepared in a condensation reaction between a primary amine of formula (Va) with an aldehyde of formula (VI) using amongst others, ethanol as a suitable solvent.

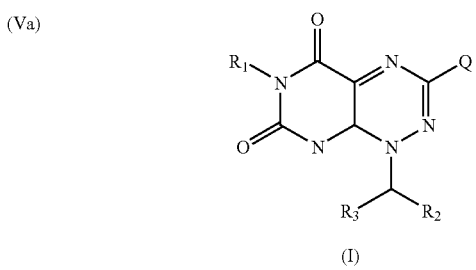

(I)

The intermediates of formula (V) and (Va) were generally prepared as depicted in reaction scheme 1.

Scheme 1

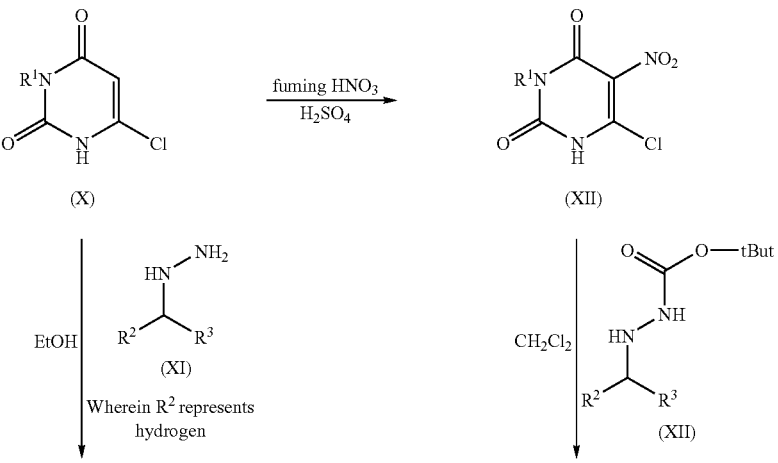

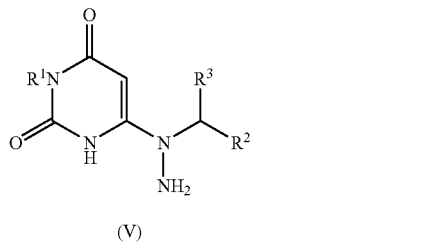

(V)  (Va)

In order to introduce further R2 substituents the urea derivative of formula (XI) was shielded with the protective group t-butoxycarbonyl. This is introduced by treating a ketone of formula formula (XIV) with t-butoxycarbonylhydrazine and subsequent reduction with Pt/C/H$_2$ in EtOH or by the slow addition of NaBH$_4$ in THF.

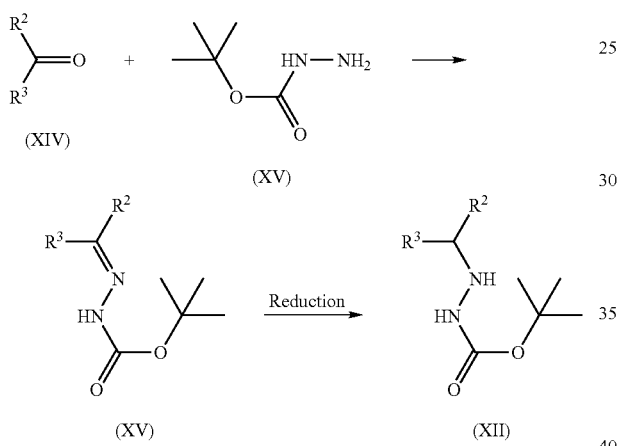

The protecting group is easily removed by treating the protected amine with trifluoroacetic acid (TFA) in CH$_2$Cl$_2$ as a solvent.

As depicted in scheme 2, art known techniques such as described in "Introduction to Organic Chemistry"—A. Streitweiser, second ed. Macmillan Publishing Inc. p 1104, were used to prepare the pyrimidines of formula (IX). In general, the synthesis of said pyrimidines consists of a condensation between 1,3-dicarbonyl compounds such as diethylpropanedioate and a material containing the general structure N—C—N such as urea and the compounds of formula (VIII). The urea compounds of formula (VIII) are prepared using art know techniques, in particular the reaction of isocyanates such as benzoylisocyanate with an amine such as represented by formula (VII). In this particular reaction scheme, the benzoyl substituent is released from the urea complex of formula (VIIIa) by hydratation with water.

Scheme 2

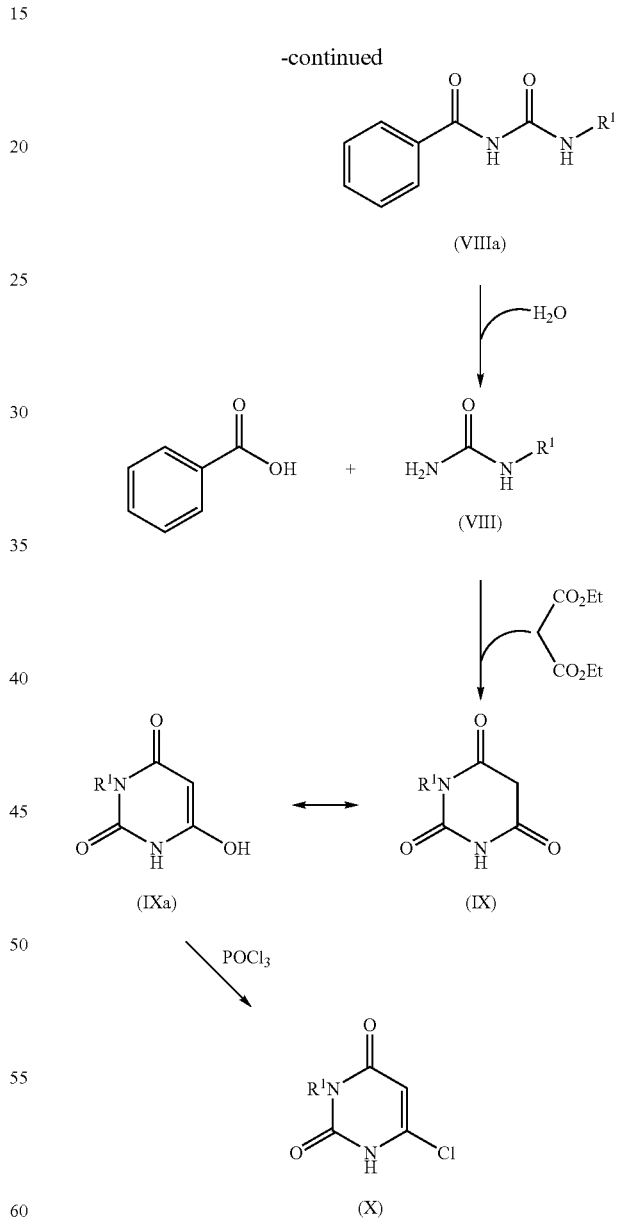

In a final step the tautomeric form of the thus obtained pyrimidines (IXa) were halogenated using an appropriate halogenating agent such as SOCl$_2$, POCl$_3$, PCl$_5$ or PBr$_3$.

The starting furanyl aldehyde of formula (VI) was prepared by the two coupling reaction described as followed:

Scheme 3

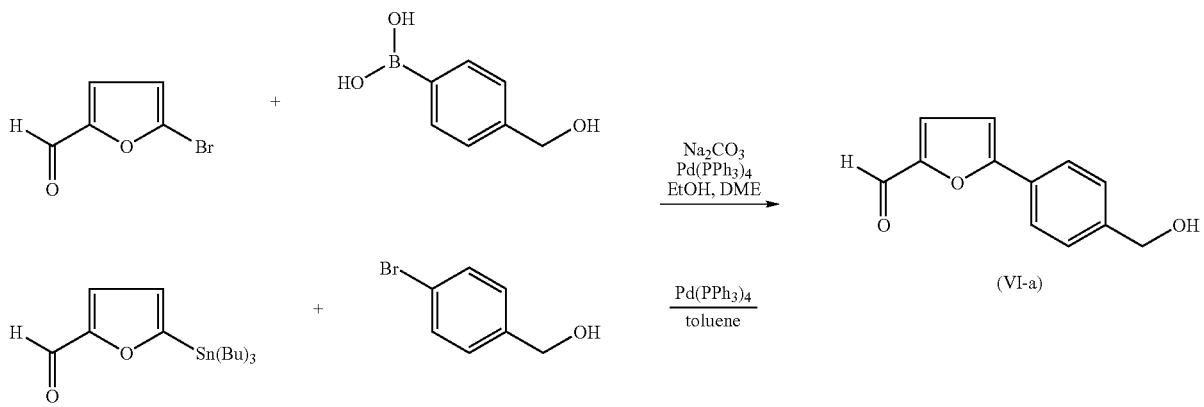

Wherein (VI-a) could be further converted using art known procedures such as the Mitsunobu reaction using the corresponding amino-alcohol. For example;

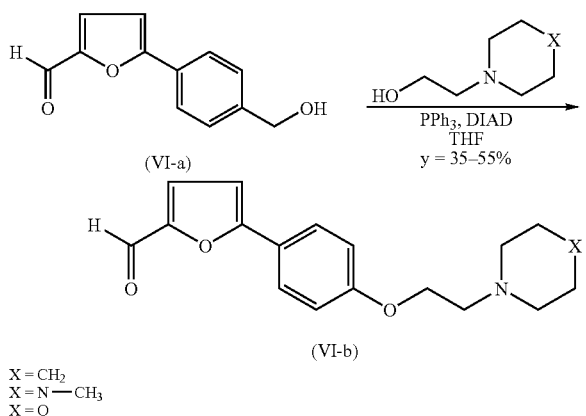

X = CH$_2$
X = N—CH$_3$
X = O

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof,
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art, for example:

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include C$_{(1-6)}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' 2$^{nd}$ edition, T W Greene & P G M Wutz, Wiley Interscience (1991).

Additionally, the N-atoms in compounds of formula (I) can be methylated by art-known methods using CH$_3$—I in a suitable solvent such as, for example 2-propanone, tetrahydrofuran or dimethylformamide.

The compounds of formula (I) can also be converted into each other following art-known procedures of functional group transformation of which some examples are mentioned hereinabove.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydro-carbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

The compounds of the present invention are useful because they possess pharmacological properties. They can therefore be used as medicines.

As described in the experimental part hereinafter, the growth inhibitory effect and anti-tumor activity of the present compounds has been demonstrated in vitro, in enzymatic assays on kinases and phosphatases involved in cell cycle regulation. Anti-tumor activity was also demonstrated in vitro in a cell based assay comprising contacting the cells with the compounds and assessing the effect of AKT3 on MAPK phosphorylation. In an alternative assay, the growth inhibitory effect of the compounds was tested on the ovarian carcinoma cell line A2780 using art known cytotoxicity assays such as LIVE/DEAD (Molecular Probes) or MTT.

Accordingly, the present invention provides the compounds of formula (I) and their pharmaceutically acceptable N-oxides, addition salts, quaternary amines and stereochemically isomeric forms for use in therapy. More particular in the treatment or prevention of cell proliferation mediated diseases. The compounds of formula (I) and their pharmaceutically acceptable N-oxides, addition salts, quaternary amines and the stereochemically isomeric forms may hereinafter be referred to as compounds according to the invention.

Disorders for which the compounds according to the invention are particularly useful are atherosclerosis, restinosis and cancer.

In view of the utility of the compounds according to the invention, there is provided a method for the treatment of an animal, for example, a mammal including humans, suffering from a cell proliferative disorder such as atherosclerosis, restinosis and cancer, which comprises administering an effective amount of a compound according to the present invention.

Said method comprising the systemic or topical administration of an effective amount of a compound according to the invention, to warm-blooded animals, including humans.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.01 mg/kg to 50 mg/kg body weight, in particular from 0.05 mg/kg to 10 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins or ethers and mixed ethers thereof wherein one or more of the hydroxy groups of the anhydroglucose units of the cyclodextrin are substituted with $C_{(1-6)}$alkyl, particularly methyl, ethyl or isopropyl, e.g. randomly methylated β-CD; hydroxy $C_{(1-6)}$alkyl, particularly hydroxyethyl, hydroxypropyl or hydroxybutyl; carboxy $C_{(1-6)}$alkyl, particularly carboxymethyl or carboxyethyl; $C_{(1-6)}$alkylcarbonyl, particularly acetyl; $C_{(1-6)}$alkyloxycarbonyl $C_{(1-6)}$alkyl or carboxy-$C_{(1-6)}$alkyloxy $C_{(1-6)}$alkyl, particularly carboxymethoxypropyl or carboxyethoxypropyl; $C_{(1-6)}$alkylcarbonyloxy $C_{(1-6)}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques, preferably, as measured by mass spectrometry, the M.S. ranges from 0.125 to 10.

The average substitution degree (D.S.) refers to the average number of substituted hydroxyls per anhydroglucose unit. The D.S. value can be determined by various analytical techniques, preferably, as measured by mass spectrometry, the D.S. ranges from 0.125 to 3.

Experimental Part

Hereinafter, the term 'RT' means room temperature, 'THF' means tetrahydrofuran, 'AcOH' means Acetic Acid, 'EtOH' means ethanol, DME means dimethyl ether, DIPE means diisopropyl ether, TFA means trifluoroacetic acid.

A. Preparation of the Intermediates

Example A1 a) A solution of 5-Bromo-2-furancarboxaldehyde (0.0171 mol) in DME (65 ml) was added dropwise to a solution of Pd(PPh$_3$)$_4$ (0.00007 mol) in DME (50 ml) at room temperature under N$_2$. The mixture was stirred for 15 minutes. A solution of (3-hydroxyphenyl)boronic acid (0.0257 mol) in EtOH (18 ml) was added. The mixture was stirred for 15 minutes. 2M K$_2$CO$_3$ (75 ml) was added. The mixture was stirred and refluxed for 4 hours, cooled to room temperature, concentrated and taken up by CH$_2$Cl$_2$. The organic layer was washed by H$_2$O, dried over MgSO$_4$, filtered and evaporated. The residue (5.9 g) was purified by column chromatography over silica gel (eluent: CH$_2$Cl$_2$/CH$_3$OH 98/2; 15–40 μm). The pure fractions were collected and the solvent was evaporated. Yielding: 3 g of intermediate 1 (88%).

b) Preparation of (intermediate 2)

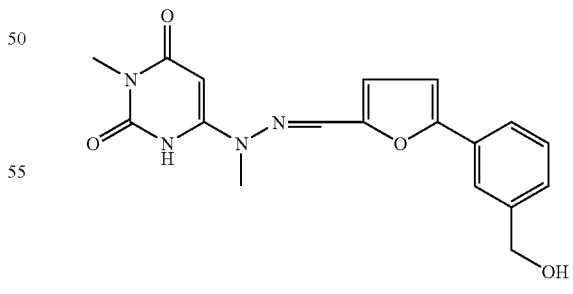

A mixture of intermediate 1 (0.0046 mol) and 3-methyl-6-(1-methylhydrazino)-2,4(1H,3H)-Pyrimidinedione (0.0046 mol) in EtOH (20 ml) was stirred at 60° C. for 3 hours, cooled to room temperature. A precipitate was filtered off, washed with diethyl ether then EtOH and dried. Yielding: 1 g of intermediate 2 (60%).

c) Preparation of

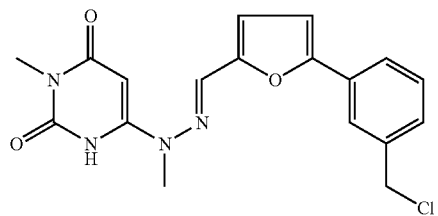
(intermediate 3)

SOCl2 (0.0485 mol) was added dropwise at 5° C. to a mixture of intermediate 2 (0.0121 mol) in CH$_2$Cl$_2$ (80 ml). The mixture was brought to room temperature, then stirred for 8 hours and the solvent was evaporated till dryness. Yielding: 6.2 g intermediate 3 (>100%). This product was used directly in the next reaction step.

d) Preparation of

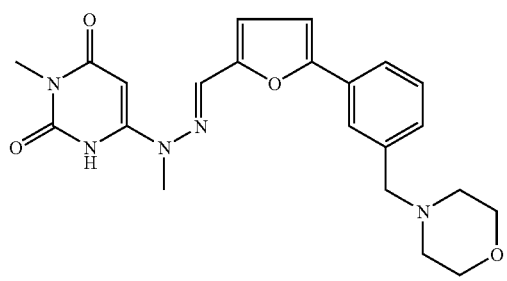
(intermediate 4)

A mixture of intermediate 3 (0.0121 mol) and morpholine (0.0242 mol) in CH$_3$CN (110 ml) was stirred and refluxed for 4 hours, then brought to room temperature. The precipitate was filtered, washed with H$_2$O, then washed twice with EtOH, then washed with diethyl ether and dried. The residue (4.5 g) was purified by column chromatography over silica gel (eluent: CH$_2$Cl$_2$ 100 to CH$_2$Cl$_2$/CH$_3$OH 98/2; 15–40 μm). The pure fractions were collected and the solvent was evaporated. Yielding: 3.2 g intermediate 4 (62%).

Example A2 a) Preparation of

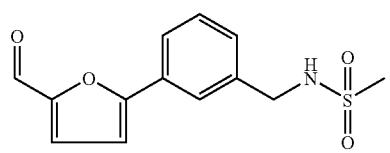
(intermediate 5)

A mixture of 5-(Tributylstannyl)furan-2-carbaldehyde (0.032 mol), N-(3-Bromobenzoyl)methanesulfonamide (0.016 mol) and Pd(PPh$_3$)$_4$ (0.0016 mol) in toluene (120 ml) was stirred and refluxed for 5 hours, then brought to room temperature. The mixture was filtered. The filtrate was evaporated. The residue (16 g) was purified by column chromatography over silica gel (eluent: CH$_2$Cl$_2$/CH$_3$OH 99/1; 15–35 μm). The pure fractions were collected and the solvent was evaporated. Yielding: 1.6 g intermediate 5 (35%).

b) Preparation of

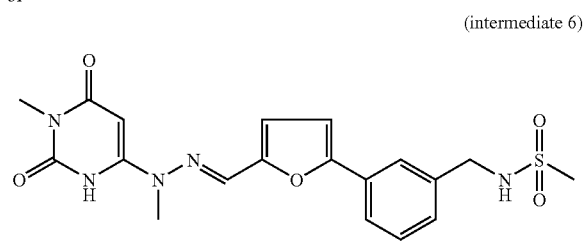
(intermediate 6)

A mixture of 3-methyl-6-(1-methylhydrazino)-2,4(1H, 3H)-Pyrimidinedione (0.0059 mol) and intermediate 5 (0.0057 mol) in EtOH (15 ml) was stirred and refluxed for 3 hours, then brought to room temperature. The mixture was filtered. The filtrate was evaporated. Yielding: intermediate 6 (48%).

Example A3 a) Preparation of

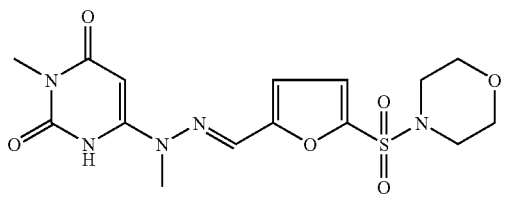
(intermediate 7)

A mixture of 3-methyl-6-(1-methylhydrazino)-2,4(1H, 3H)-Pyrimidinedione (0.0077 mol) and 4-[(5-formyl-2-furanyl)sulfonyl]-morpholine (0.01 mol) in EtOH (15 ml) was stirred and refluxed for 3 hours then brought to room temperature. The precipitate was filtered, rinsed with EtOH and dried. Yielding: intermediate 7 (58%) brought to room temperature. The precipitate was filtered, rinsed with EtOH and dried. Yielding: intermediate 7 (58%).

Example A4 a) Preparation of

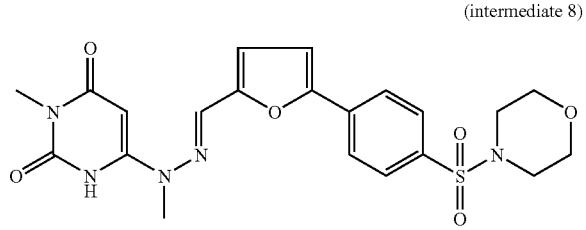
(intermediate 8)

A mixture of [[4-(5-formyl-2-furanyl)phenyl]sulfonyl]-morpholine (0.0105 mol), and methyl-6-(1-methylhydrazino)-2,4(1H,3H)-Pyrimidinedione (0.0105 mol) in EtOH (70 ml) was stirred and refluxed for 2 hours then brought to room temperature. The precipitate was filtered, washed with EtOH and dried with diethyl ether. Yielding: intermediate 8 (92%).

Example A5 a) Preparation of

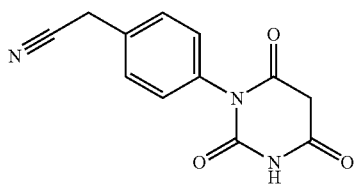
(intermediate 11)

A mixture of N-[4-(cyanomethyl)phenyl]urea (intermediate 10) (0.1141 mol), diethyl ester propanedioic acid (0.1141 mol) and EtONa/EtOH 21% (0.1198 mol) in EtOH (250 ml) was stirred and refluxed for 5 days, then brought to room temperature. The precipitate was filtered, washed with EtOH, then taken up in H$_2$O, acidified with HCl 3N and filtered. The precipitate was washed with H$_2$O, then with diethyl ether and dried. Yielding: 16.5 g intermediate 11 (59%).

b) Preparation of

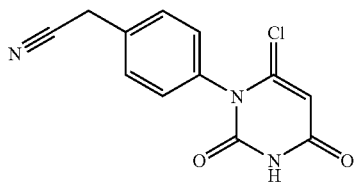
(intermediate 12)

and preparation of

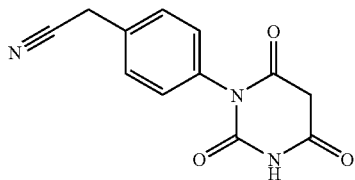
(intermediate 13)

H$_2$O (0.183 mol) was added very slowly to a mixture of intermediate 11 (0.0678 mol) and POCl$_3$ (0.848 mol). The mixture was stirred and refluxed for 40 minutes, then brought to room temperature and the solvent was evaporated till dryness. Ice water was added very slowly. The mixture was stirred for 10 minutes. The precipitate was filtered, washed with H$_2$O, then with diethyl ether and dried. The residue (14.6 g) was purified by column chromatography over silica gel (eluent: CH$_2$Cl$_2$/CH$_3$OH 97.5/2.5; 15–35 µm). Two fractions were collected and the solvent was evaporated. Yielding: 6.1 g intermediate 12 and 0.3 g intermediate 13.

c) Preparation of

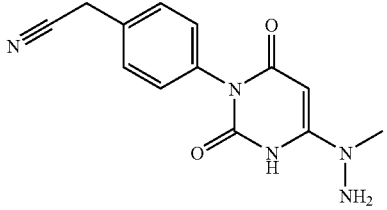
(intermediate 14)

and preparation of

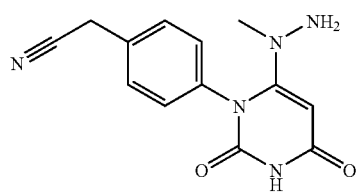
(intermediate 15)

Methyl-hydrazine (0.183 mol) was added very slowly to a mixture of intermediate 12 (0.0678 mol) and intermediate 13 (0.848 mol). The mixture was stirred and refluxed for 40 minutes, then brought to room temperature and the solvent was evaporated till dryness. Ice water was added very slowly. The mixture was stirred for 10 minutes. The precipitate was filtered, washed with H$_2$O, then with diethyl ether and dried. The residue (14.6 g) was purified by column chromatography over silica gel (eluent: CH$_2$Cl$_2$/CH$_3$OH 97.5/2.5; 15–35 µm). Two fractions were collected and the solvent was evaporated. Yielding: 6.1 g intermediate 14 and 0.3 g intermediate 15.

d) Preparation of

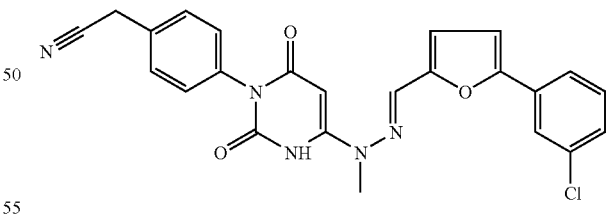
(intermediate 16)

A mixture of intermediate 14 (0.0055 mol), intermediate 15 (0.0055 mol) and 5-(3-chlorophenyl)-2-furancarboxaldehyde (0.011 mol) in EtOH (80 ml) was stirred and refluxed for 1 hour and 30 minutes, then brought to room temperature. The precipitate was filtered, washed with EtOH, then with diethyl ether and dried. The residue (4.2 g) was purified by column chromatography over silica gel (eluent: CH$_2$Cl$_2$/CH$_3$OH 97/3; 15–40 µm). Three fractions were collected and the solvent was evaporated. Yielding: intermediate 16 (20%)

Example A6 a) Preparation of

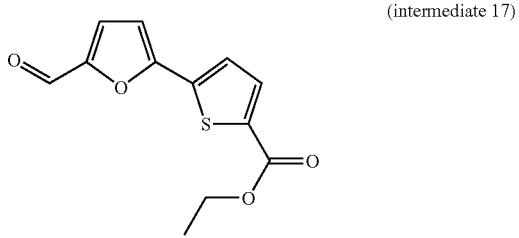
(intermediate 17)

A mixture of 5-bromo-ethyl ester 2-thiophenecarboxylic acid (0.0213 mol), 5-(tributylstannyl)-2-furancarboxaldehyde (0.0425 mol) and Pd(PPh$_3$)$_4$ (0.0021 mol) in methylphenyl (164 ml) was stirred and refluxed for 3 hours. The solvent was evaporated till dryness. The residue was purified by column chromatography over silica gel (eluent: CH$_2$Cl$_2$/EtOAc 100/0 to 98/2; 15–35 μm). The pure fractions were collected and the solvent was evaporated. Yielding: 3.42 g intermediate 17 (64%).

b) Preparation of

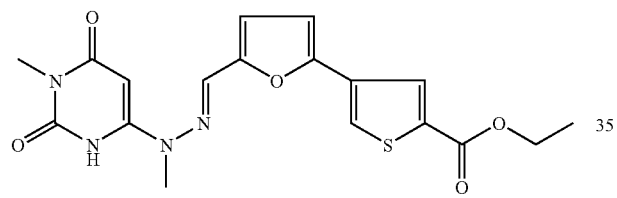
(intermediate 18)

A mixture of 3-methyl-6-(1-methylhydrazino)-2,4(1H,3H)-pyrimidinedione (0.0088 mol) and intermediate 17 (0.0088 mol) in EtOH (50 ml) was stirred and refluxed for 4 hours. The precipitate was filtered off and dried. Yielding: 2.9 g intermediate 18 (82%).

Example A7 a) Preparation of

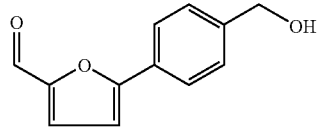
(intermediate 19)

A solution of 5-bromo-2-furancarboxaldehyde (0.0171 mol) in DME (15 ml) was added dropwise at room temperature to a solution of Pd(PPh$_3$)$_4$ (0.0045 mol) in DME (50 ml) under N$_2$ flow. The mixture was stirred for 20 minutes. A suspension of [4-(hydroxymethyl)phenyl]-boronic acid (0.0257 mol) in EtOH (18 ml) was added. The mixture was stirred for 20 minutes. Na$_2$CO$_3$ (0.15 mol) was added. The mixture was stirred and refluxed for 4 hours, then brought to room temperature. The organic layer was evaproated. The residue was taken up in CH$_2$Cl$_2$ and washed with H$_2$O. The organic layer was separated, dried (MgSO$_4$), filtered, and the solvent was evaporated. The residue (4.1 g) was purified by column chromatography over silica gel (eluent: CH$_2$Cl$_2$/CH$_3$OH 99/1; 15–40 μm). The pure fractions were collected and the solvent was evaporated. Yielding: 2.8 g intermediate 19 (82%).

b) Preparation of

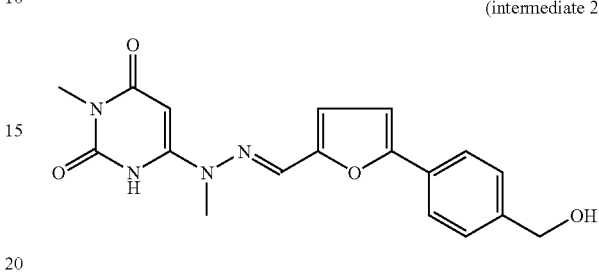
(intermediate 20)

A mixture of intermediate 19 (0.0133 mol) and 3-methyl-6-(1-methylhydrazino)-2,4(1H,3H)-pyrimidinedione (0.0133 mol) in EtOH (81 ml) was stirred and refluxed for 2 hours. The precipitate was filtered, washed twice with EtOH and dried with diethyl ether. Yielding: 4.1 g intermediate 20 (87%).

c) Preparation of

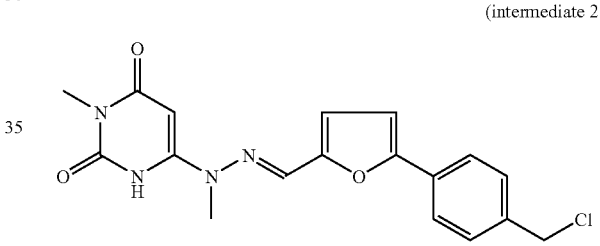
(intermediate 21)

SOCl$_2$ (0.0349 mol) was added dropwise at 5° C. to a mixture of intermediate 20 (0.0087 mol) in CH$_2$Cl$_2$ (60 ml). The mixture was brought to room temperature and stirred for 4 hours and 30 minutes. The solvent was evaporated till dryness. Yielding: 3.8 g intermediate 21 (>100%). This product was used directly in the next reaction step.

Example A8

Preparation of

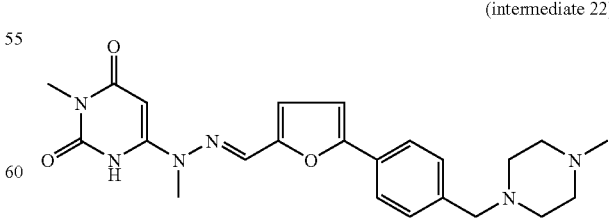
(intermediate 22)

A mixture of intermediate 21 (0.005 mol) and B (0.0101 mol) in CH$_3$CN (50 ml) was stirred and refluxed for 3 hours, then brought to room temperature. H$_2$O was added. The mixture was extracted twice with EtOAc. The aqueous layer was satured with NaCl. The organic layer was extracted with EtOAc and dried. The residue was taken up in EtOH/diethyl ether. The precipitate was filtered off and dried. Yielding: 1.2 g intermediate 22.

Example A9 a) Preparation of

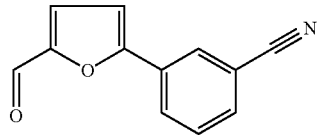
(intermediate 23)

Na$_2$CO$_3$ (83 ml) then a mixture of 3-Cyanophenylboronic acid (0.0396 mol) in methanol (41 ml) were added to a mixture of 5-bromo-2-furancarboxaldehyde (0.0322 mol) and Pd(PPh$_3$)$_4$ (0.0009 mol) in methylphenyl (166 ml) under N$_2$ flow. The mixture was stirred and refluxed for 4 hours and extracted with EtOAc. The precipitate was filtered off and dried. Yielding: 2.76 g intermediate 23 (43%).

b) Preparation of

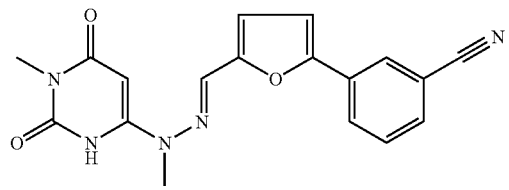
(intermediate 24)

A mixture of methyl-6-(1-methylhydrazino)-2,4(1H,3H)-pyrimidinedione (0.0088 mol) and intermediate 23 (0.0088 mol) in EtOH (50 ml) was stirred and refluxed for 5 hours. The precipitate was filtered off and dried. Yielding: 2.07 g intermediate 24 (67%).

c) Preparation of

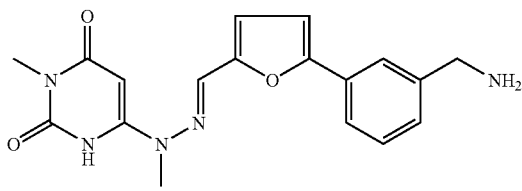
(intermediate 25)

A mixture of intermediate 25 (0.0059 mol) and Raney Nickel (2.07 g) in NH$_3$/CH$_3$OH 7N (100 ml) was hydrogenated at room temperature for 4 hours under a 3 bar pressure of H$_2$, then filtered over celite. The filtrate was evaporated. Yielding: 2.09 g intermediate 25 (>100%).

d) Preparation of

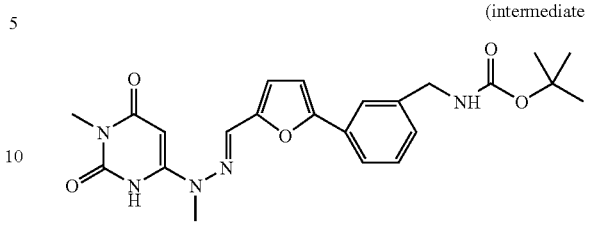
(intermediate 26)

Bis(1,1-dimethylethyl) ester dicarbonic acid (0.0059 mol) was added portionwise at 0° C. to a mixture of intermediate 25 (0.0059 mol) and Et$_3$N (0.0059 mol) in CH$_2$Cl$_2$ (21 ml). The precipitate was filtered off and dried. Yielding: 2.68 g intermediate 26 (>100%).

Example A10 a) Preparation of

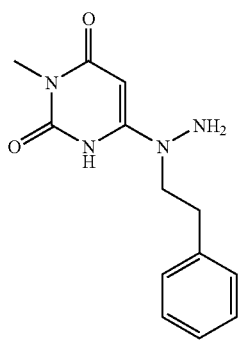
(intermediate 27)

A mixture of 6-chloro-3-methyl-2,4(1H,3H)-pyrimidinedione (0.0195 mol) and 1-(2-Phenylethyl)hydrazine (0.044 mol) in EtOH (50 ml) was stirred and refluxed for 5 hours. The solvent was evaporated. The residue was purified by column chromatography over silica gel (eluent: CH$_2$Cl$_2$/CH$_3$OH 95/5; 15–35 µm). The pure fractions were collected and the solvent was evaporated. Yielding: 2.2 g intermediate 27 (43%).

b) Preparation of

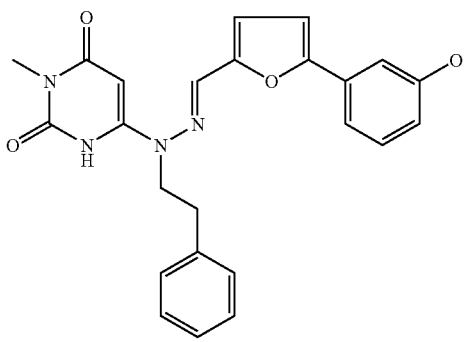
(intermediate 28)

A mixture of intermediate 27 (0.0041 mol) and 5-(3-chlorophenyl)-2-furancarboxaldehyde (0.0041 mol) in EtOH (11 ml) was stirred and refluxed for 5 hours. The precipitate was filtered off and dried. Yielding: 1.58 g intermediate 28 (85%).

Example A11 a) Preparation of

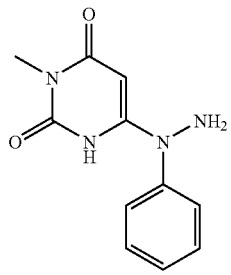
(intermediate 29)

A mixture of 6-Chloro-3-methyluracil (0.0622 mol) and phenylhydrazine (0.137 mol) in C (100 ml) was stirred and refluxed for 3 hours, then filtered. This fraction was washed with hot EtOH and dried. The mother layer was purified by column chromatography over silica gel (eluent: CH2Cl2/CH3OH 94/6; 15–35 µm). Two fractions were collected and the solvent was evaporated. Yielding: 8.5 g intermediate 29 (80%).

b) Preparation of

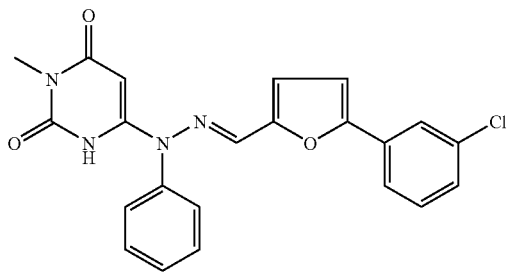
(intermediate 30)

A mixture of intermediate 29 (0.005 mol) and 5-(3-chlorophenyl)-2-furaldehyde (0.0057 mol) in EtOH (20 ml) was stirred and refluxed for 1 hour, then brought to room temperature. The precipitate was filtered off and dried. Yielding: 1.8 g intermediate 30.

Example A12

(a) Preparation of

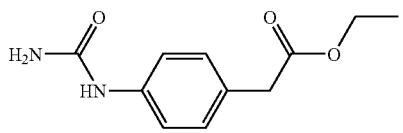
(intermediate 31)

A mixture of ethyl-2-(4-aminophenyl)acetate (0.161 mol), KOCN (0.322 mol) and TFA (0.225 mol) in toluene (250 ml) was stirred at 60° C. for 24 hours, then brought to room temperature and filtered. The precipitate was washed with H₂O, then with diethyl ether and dried under a vacuo. Yielding: intermediate 31 (100%).

b) Preparation of

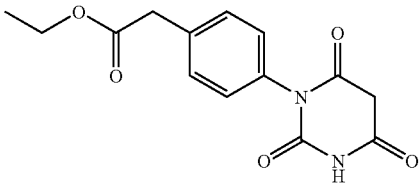
(intermediate 32)

A mixture of intermediate 31 (0.223 mol), diethyl malonate (0.223 mol) and EtONa/EtOH 21% (0.234 mol) in EtOH (500 ml) was stirred and refluxed for 4 days, then brought to room temperature and the solvent was evaporated. The residue was taken up in ice water, acidified with HCl 3N, taken up in CH₂Cl₂ and washed with H₂O. The organic layer was separated, dried (MgSO₄), filtered, and the solvent was evaporated. The residue was crystallized from diethyl ether. The precipitate was filtered off and dried. Yielding: 27.8 g intermediate 32 (62%).

c) Preparation of

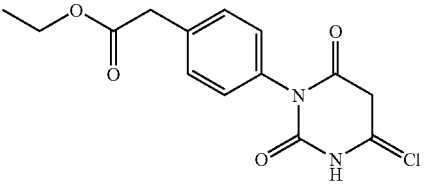
(intermediate 33)

H₂O (0.258 mol) was added dropwise slowly to a mixture of intermediate 33 (0.0957 mol) and POCl₃ (1.197 mol). The mixture was stirred and refluxed for 30 minutes, then brought to room temperature and the solvent was evaporated till dryness. Ice water was added. The mixture was extracted twice with CH₂Cl₂. The organic layer was separated, dried (MgSO₄), filtered and the solvent was evaporated. The residue was purified by column chromatography over silica gel (eluent: CH₂Cl₂/CH₃OH/NH₄OH 94/6/0.1 to 90/10/0.2; 15–40 µm). The pure fractions were collected and the solvent was evaporated. Yielding: 8.5 g intermediate 33 (28%).

d) Preparation of

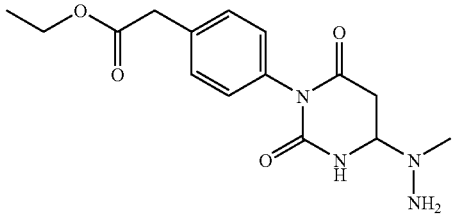
(intermediate 34)

A mixture of intermediate 34 (0.029 mol) and methylhydrazine (0.038 mol) in EtOH (85 ml) was stirred and refluxed for 6 hours, cooled to room temperature and stirred at this temperature overnight. A precipitate was filtered off, washed with Et$_2$O and dried. Yielding: 7.7 g of intermediate 34 (82%).

e) Preparation of (intermediate 35)

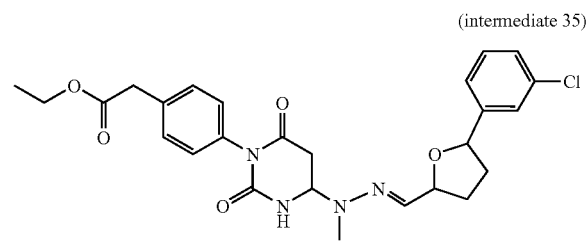

A mixture of intermediate 34 (0.0109 mol) and 5-(3-chlorophenyl)-2-furaldehyde (0.0109 mol) in C (70 ml) was stirred and refluxed for 1 hour then cooled to room temperature. A precipitate was filtered off and washed by EtOH and Et$_2$O then dried. Yielding: 4.3 g of intermediate 35 (76%).

f) Preparation of (intermediate 36)

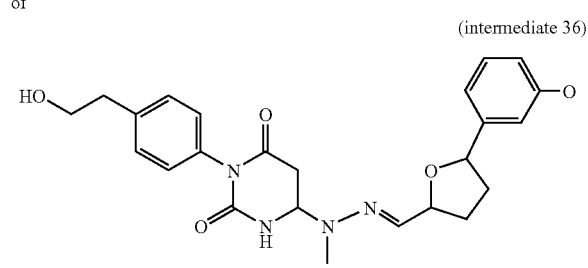

A solution of intermediate 35 (0.0078 mol) in THF (80 ml) was stirred and refluxed. KBH$_4$ (0.039 mol) and LiCl (0.039 mol) were added portionwise. The mixture was stirred and refluxed 24 hours, cooled to room temperature, poured out into ice water and extracted with CH$_2$Cl$_2$. A precipitate was crystallized in the organic layer, filtered off and dried. 0.3 g of was taken up in a little quantity of MeOH, CH$_2$Cl$_2$ and DIPE. The precipitate was filtered off and dried. Yielding: 0.2 g of intermediate 36.

Example A13 a) Preparation of (intermediate 37)

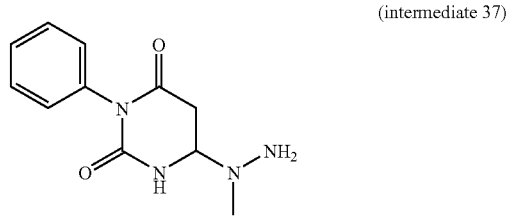

A mixture of 6-chloro-3-phenyl-2,4(1H,3H)-Pyrimidinedione (0.0179 mol) and methylhydrazine (0.039 mol) in EtOH (40 ml) was stirred and refluxed for 90 minutes, then cooled and stirred at room temperature for 1 hour. The precipitate was filtered, washed with diethyl ether and dried. Yielding: 4.3 g of intermediate 37 (>100%)

b) Preparation of (intermediate 38)

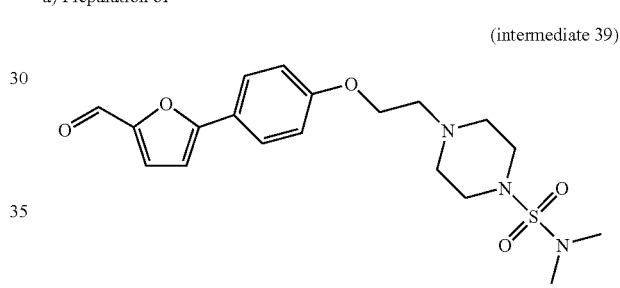

A mixture of intermediate 37 (0.0053 mol) and 5-(3-chlorophenyl)-2-furaldehyde (0.0053 mol) in EtOH (15 ml) was stirred and refluxed for 2 hours, then cooled to room temperature, cooled to 5° C. in a bath of ice. The precipitate was filtered, washed with diethyl ether and dried. Part of this fraction (0.3 g) was crystallized from EtOH. The precipitate was filtered, washed with diethyl ether and dried. Yielding: 0.2 g intermediate 38.

Example A14 a) Preparation of (intermediate 39)

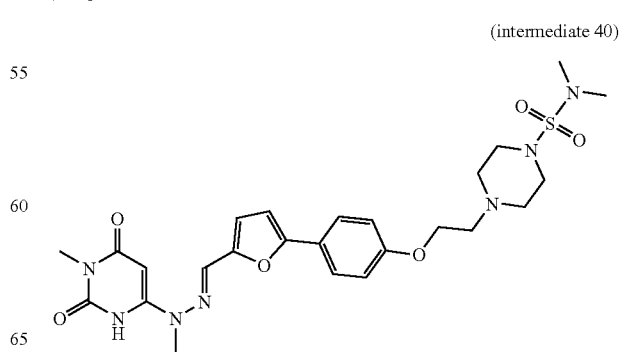

4-(4,5-dihydro-4,4-dimethyl-2-oxazolyl)-Pyridine (0.0092 mol) was added dropwise at 5° C. to a mixture of 5-(4-hydroxyphenyl)-2-Furancarboxaldehyde (0.007 mol), 4-(2-hydroxyethyl)-N,N-dimethyl-1-piperazinesulfonamide (0.0085 mol) and PPh$_3$ (0.0121 mol) in THF. The mixture was stirred at 5° C. for 2 hours, poured out into H$_2$O, then into HCl 3N. The mixture was washed with EtOAc. The aqueous layer was basified with K$_2$CO$_3$. The mixture was extracted with EtOAc. The organic layer was separated, dried (MgSO$_4$), filtered, and the solvent was evaporated. Yielding: 2.6 g intermediate 39 (75%).

b) Preparation of (intermediate 40)

A mixture of 3-methyl-6-(1-methylhydrazino)-2,4(1H,3H)-Pyrimidinedione (0.017 mol) and intermediate 39 (0.0373 mol) in EtOH (50 ml) was stirred and refluxed for 2 hours, then cooled. The precipitate was filtered, rinsed with EtOH and dried. Yielding: 2.12 g intermediate 40 (59%).

Example A15 a) Preparation of (intermediate 41)

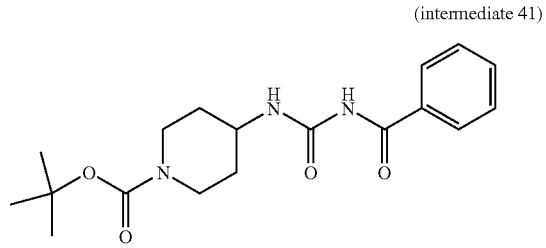

4-amino-1-Boc-piperidine (0.0484 mol) was added portionwise at 0° C. to a mixture of benzoyl isocyanate (0.0533 mol) in $CH_2Cl_2$ (28o ml) under $N_2$ flow. The mixture was stirred at room temperature for 3 hours. The solvent was evaporated. The residue was crystallized from DIPE. The precipitate was filtered off and dried. Yielding: 7.75 g of intermediate 41 (46%).

b) Preparation of (intermediate 42)

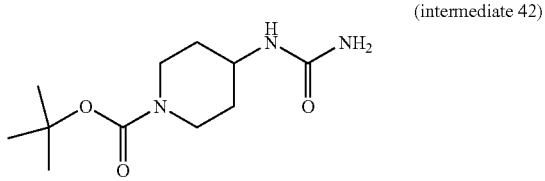

A mixture of intermediate 41 (0.0223 mol) and NaOH (0.38 mol) in $CH_3OH$ (100 ml) and $H_2O$ (100 ml) was stirred at room temperature for 12 hours, then stirred and refluxed for 1 hour and brought to room temperature. $CH_3OH$ was evaporated. The precipitate was filtered, washed with $H_2O$ and dried. Yielding: 4.46 g of intermediate 42 (82%).

c) Preparation of (intermediate 43)

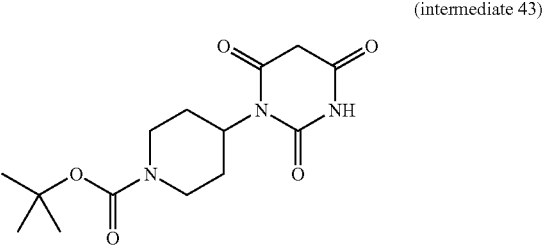

A mixture of intermediate 42 (0.0183 mol), diethyl malonate (0.02 mol) and EtONa/EtOH 21% (0.02 mol) in EtOH (60 ml) was stirred and refluxed for a week-end, then brought to room temperature and the solvent was half evaporated. The mixture was taken up in $H_2O$. HCl 3N was added till pH 5.5 was obtained. The mixture was extracted twice with $CH_2Cl_2$. The organic layer was separated, dried ($MgSO_4$), filtered, and the solvent was evaporated. The residue was taken up in cyclohexane. The precipitate was filtered off and dried. Yielding: 5.4 g of intermediate 43 (94%).

d) Preparation of (intermediate 44)

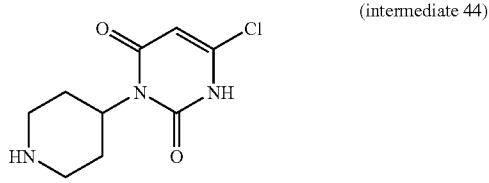

$H_2O$ (0.0459 mol) was added dropwise slowly at room temperature to a mixture of intermediate 43 (0.017 mol) and $POCl_3$ (0.21 mol). The mixture was stirred and refluxed for 30 minutes, then brought to room temperature and the solvent was evaporated. The residue was taken up in ice. $K_2CO_3$ was added till pH 7 obtained. The mixture was washed with $CH_2Cl_2$ and the solvent was evaporated. The residue was taken up in DIPE. The precipitate was filtered off and dried. Yielding: 3.63 g of intermediate 44.

d) Preparation of (intermediate 45)

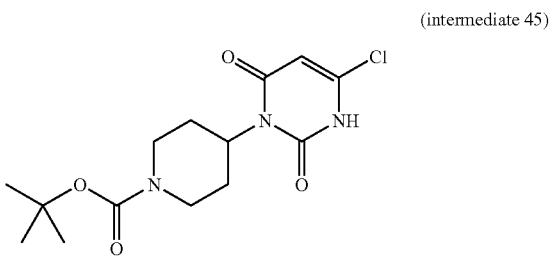

A mixture of intermediate 44 (0.017 mol) and Boc-anhydride (0.026 mol) in $CH_2Cl_2$ (70 ml) and $CH_3OH$ (15 ml) was stirred at room temperature for 12 hours. $H_2O$ was added. The mixture was decanted. The solvent was evaporated. The residue was taken up in $CH_2Cl_2$. Activated carbon was added. The mixture was filtered over celite. The solvent was evaporated. The residue was taken up in DIPE. The precipitate was filtered off and dried. Yielding: 1.7 g of intermediate 45.

f) Preparation of (intermediate 46)

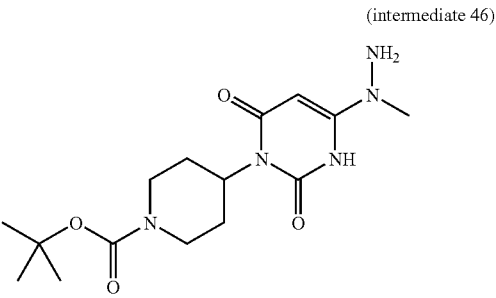

A mixture of intermediate 45 (0.0052 mol) and methylhydrazine (0.012 mol) in EtOH (20 ml) was stirred and refluxed for 1 hours, then brought to room temperature. The solvent was evaporated. Yielding: 1.76 g of intermediate 46.

g) Preparation of

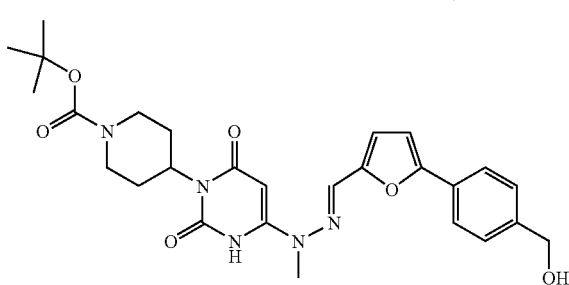
(intermediate 47)

A mixture of intermediate 46 (0.0285 mol) and 5-(4-hydroxyphenyl)-2-furancarboxaldehyde (0.0285 mol) in EtOH (150 ml) was stirred and refluxed for 2 hours, then brought to room temperature and the solvent was evaporated. The residue was taken up in $CH_2Cl_2$. The organic layer was washed with $H_2O$, dried ($MgSO_4$), filtered and the solvent was evaporated. The residue (16 g) was purified by column chromatography over silica gel (eluent: $CH_2Cl_2$/EtOAc 60/40; 15–40 μm). The pure fractions were collected and the solvent was evaporated. Yielding: 7.8 g of intermediate 47 (52%).

Example A16 a) Preparation of

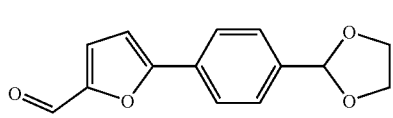
(intermediate 48)

A mixture of 2-(4-bromophenyl)-1,3-dioxolane (0.061 mol), 5-(tributylstannyl)furan-2-carbaldehyde (0.079 mol) and $Pd(PPh_3)_4$ (3.5 g) in toluene (200 ml) was stirred and refluxed for 3 hours, then brought to room temperature and filtered over celite. Celite was washed with $CH_2Cl_2$. The filtrate was evaporated. The residue (53 g) was purified by column chromatography over silica gel (eluent: $CH_2Cl_2$ 100; 15–35 μm). The pure fractions were collected and the solvent was evaporated. Yielding: 7.2 g intermediate 48 (48%).

b) Preparation of

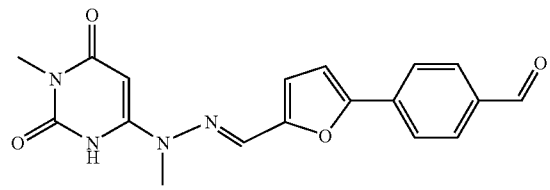
(intermediate 49)

A mixture of 4-(4,5-dihydro-4,4-dimethyl-2-oxazolyl)-Pyridine (0.026 mol) and intermediate 48 (0.03 mol) in EtOH (100 ml) was stirred and refluxed for 2 hours, then brought to room temperature. The precipitate was filtered, washed with EtOH and dried. Yielding: 8.25 g of intermediate 49 (90%).

Example A17 a) Preparation of

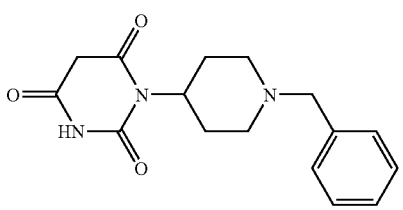
(intermediate 50)

A mixture of [1-(phenylmethyl)-4-piperidinyl]-urea (0.0248 mol), diethyl malonate (0.0248 mol) and EtONa/EtOH (0.0248 mol) in EtOH (90 ml) was stirred and refluxed for 6 days. The solvent was evaporated till dryness. The residue was taken up in $H_2O$. HCl 1N was added till pH 7 was obtained. The solvent was evaporated till dryness. Yielding: 7.5 g of intermediate 50 (>100%).

b) Preparation of

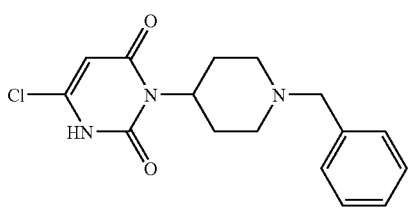
(intermediate 51)

$H_2O$ (0.0755 mol) was added dropwise very slowly to a mixture of intermediate 50 (0.0282 mol) and $POCl_3$ (0.355 mol). The mixture was stirred and refluxed for 30 minutes. The solvent was evaporated till dryness. The residue was poured out on ice and basified with $K_2CO_3$. The residue was dried. Yielding: 6.56 g of intermediate 51 (73%).

c) Preparation of

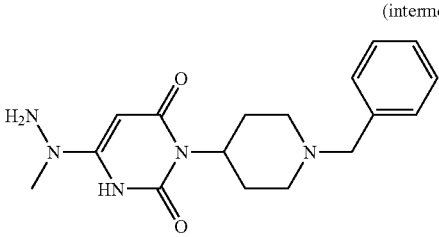
(intermediate 52)

A mixture of intermediate 51 (0.0205 mol) and methylhydrazine (0.041 mol) in EtOH (66 ml) was stirred and refluxed for 3 hours and filtered. The filtrate was evaporated till dryness. The residue was taken up in $CH_2Cl_2/CH_3OH/NH_4OH$ (90/10/0.5) and purified over $SiO_2$ (35–70 μm). The pure fractions were collected and the solvent was evaporated. Yielding: 2.65 g of intermediate 52 (39%).

d) Preparation of

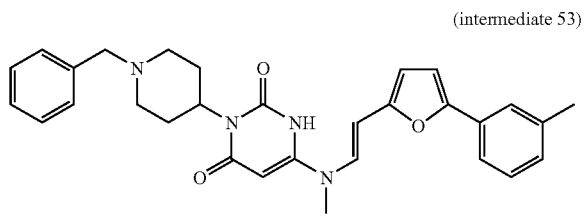
(intermediate 53)

A mixture of intermediate 52 (0.0034 mol) and 2-(3-chlorophenyl)-2-furancarboxaldehyde (0.0034 mol) in EtOH (11 ml) was stirred and refluxed for 5 hours. The precipitate was filtered off and dried. Yielding: 1.2 g of intermediate 53 (68%).

Example A18 a) Preparation of

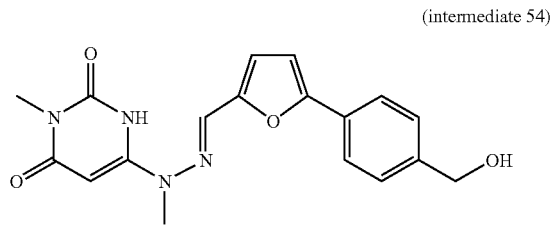
(intermediate 54)

A mixture of 5-(4-hydroxymethylphenyl)-2-furancarboxaldehyde (0.0133 mol) and 3-methyl-6-(1-methylhydrazino)-2,4(1H,3H)-Pyrimidinedione (0.0133 mol) in EtOH (81 ml) was stirred and refluxed for 2 hours. The precipitate was filtered, washed twice with EtOH and dried with diethylether. Yielding: 4.1 g of intermediate 54 (87%).

b) Preparation of

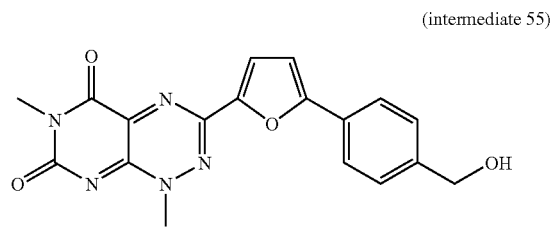
(intermediate 55)

NaNO$_2$ (0.0033 mol) was added at 5° C. to a mixture of intermediate 54 (0.0022 mol) in AcOH (8 ml) and H$_2$O (0.8 ml). The mixture was brought to room temperature and stirred overnight. Diethyl ether was added. The precipitate was filtered off and dried. Yielding: 6 g of intermediate 55 and its nitrosoderivative c) Preparation of

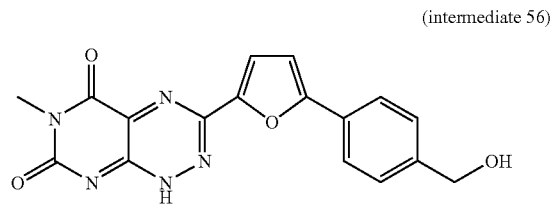
(intermediate 56)

A mixture of intermediate 55 (0.0158 mol) and its nitrosoderivative (0.0158 mol) in DMF (120 ml) was stirred at 90° C. for 2 hours, then brought to room temperature. Ice and water were added. The mixture was stirred for 10 minutes. the precipitate was filtered off and dried. Yielding: 5.9 g of intermediate 56 (59%).

Example A19 a) Preparation of

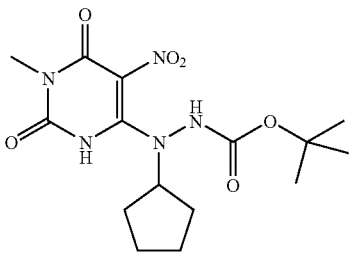
(intermediate 61)

A mixture of 6-chloro-2-hydroxy-3-methyl-5-nitro-3,5-dihydropyrimidine-4-one (0.114 mol) in CH$_2$Cl$_2$ (250 ml) was stirred at room temperature and a solution of

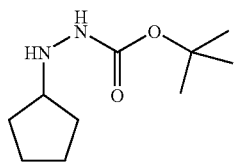

(t-butoxycarbonyl-cyclopentylhydrazine) (0.17 mol) in CH$_2$Cl$_2$ (50 ml) was added dropwise. After addition of t-butoxycarbonyl-cyclopentylhydrazine, the mixture was stirred at room temperature for 4 hours. The precipitate was filtered off, and washed with DIPE and dried under vacuum at 50° C. The residual fraction was stirred in a mixture of CH$_2$Cl$_2$/DIPE (8/2). The precipitate was filtered off, washed and dried under vacuum at 50° C. Yielding 36.4 g of intermediate 61 (87%).

b) Preparation of

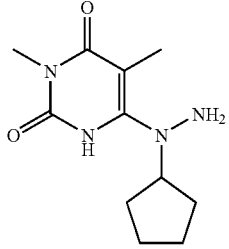
(intermediate 62)

A solution of intermediate 61 (0.054 mol), CF$_3$COOH (40 ml) and CH$_2$Cl$_2$ (160 ml) was stirred at room temperature for 4 hours. The reaction was completed and the solvent was removed under reduced pressure. The residual fraction was stirred in DIPE/2-propanol (1/1). The precipitate was filtered off, washed and dried under vacuum at 50° C. Yielding: 13.1 g of intermediate 62 (90%).

B. Preparation of the Compounds

Example B1

Preparation of (compound 1)

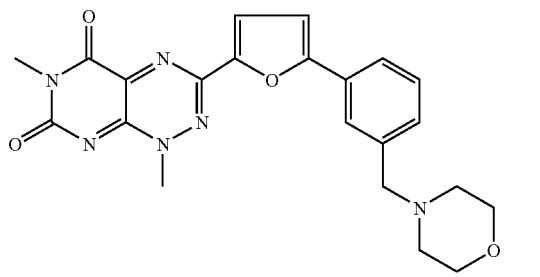

a) NaNO₂ (0.0113 mol) was added portionwise at 5° C. to a mixture of intermediate 4 (0.0075 mol) in AcOH (32 ml) and H₂O (1.6 ml). The mixture was brought to room temperature and stirred overnight. Diethyl ether was added. The precipitate was filtered off and dried. Yielding: 6 g compound I and its nitrosoderivative (global yield: >100%). This product was used directly in the next reaction step.

b) A mixture of (0.0011 mol) compound 1 and the nitrosoderivative thereof (0.001 mol) and 1,4-dimercapto-2,3-butanediol (0.0033 mol) in EtOH (10 ml) was stirred at room temperature for a week-end. The precipitate was filtered, washed twice with EtOH/H₂O then washed three times with CH₃OH/diethyl ether and dried. Yielding: 0.337 g compound 1 (34%)

Example B2

Preparation of (compound 2)

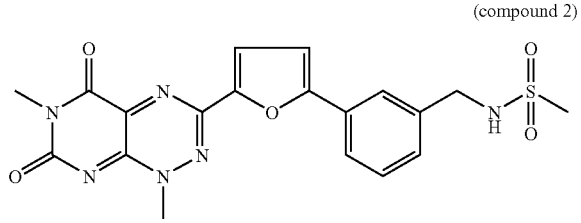

a) A mixture of intermediate 6 (0.0028 mol) and NaNO₂ (0.0042 mol) in H₂O (0.7 ml) and AcOH (12 ml) was stirred at room temperature for 36 hours, then diluted in diethyl ether. The precipitate was filtered off and dried. Yielding: 1.3 g compound 2 and its nitrosoderivative (>100%).

b) A mixture of (0.0003 mol) compound 2 and its nitrosoderivative (0.0003 mol) and 1,4-dimercapto-2,3-butanediol (0.0013 mol) in EtOH (10 ml) was stirred at room temperature for 24 hours. 1,4-Dimercapto-2,3-butanediol (0.0013 mol) was added again. The mixture was stirred for 6 days. The precipitate was filtered off and dried. Yielding: 0.162 g nitrosoderivative. This fraction was taken up in EtOH/CH₃OH. The precipitate was filtered off and dried. Yielding: 0.11 g compound 2 (37%).

Example B3

Preparation of (compound 4)

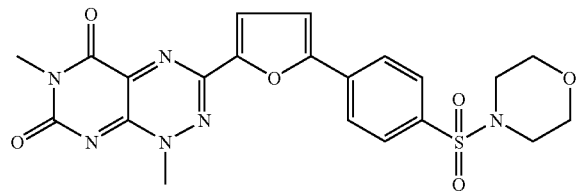

a) NaNO₂ (0.0047 mol) was added at 5° C. to a mixture of intermediate 8 (0.031 mol) in AcOH (15 ml) and H₂O (0.7 ml). The mixture was brought to room temperature and stirred at room temperature for 5 hours. Diethyl ether was added. The precipitate was filtered off and dried. Yielding: 1.8 g compound 4 (quantitative) and the nitrosoderivative

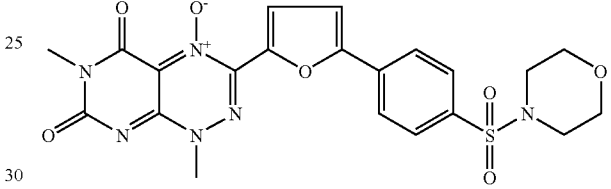

(intermediate 9) thereof. The product was used without further purification in the next reaction step.

b) A mixture of (0.0010 mol) compound 4 and its nitrosoderivative (0.0010) and 1,4-dimercapto-2,3-butanediol (0.0029 mol) in EtOH (20 ml) was stirred at room temperature for 3 days. 1,4-dimercapto-2,3-butanediol (0.0029 mol) was added. The mixture was stirred at room temperature for 4 days. The precipitate was filtered off and dried. Yielding 0.8 g fraction 1. A solution of 1,4-dimercapto-2,3-butanediol (0.0029 mol) in EtOH (20 ml) was added to this fraction. The mixture was stirred at room temperature for 2 days. The precipitate was filtered off and dried. Yielding: 0.6 g fraction 2. This fraction was washed with diethyl ether. The precipitate was filtered off and dried. Yielding: 0.5 g fraction 3. This fraction was dried at 50° C. under a vaccuo for 6 hours. Yielding: 0.258 g fraction 4. This fraction was dried at 80° C. under a vaccuo for 6 hours. Yielding: 0.242 g compound 4.

Example B4

Preparation of (compound 5)

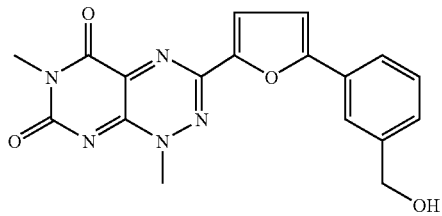

a) A mixture of intermediate 2 0.0033 mol) in AcOH (12 ml) and H₂O (0.6 ml) was cooled to 0° C. KNO₂ (0.0050 mol) was added portionwise. The mixture was brought to room temperature and stirred at room temperature for 24 hours. Diethyl ether was added. The precipitate was filtered off and dried. Yielding: 1.5 g compound 5 and its nitrosoderivative. The product was used without further purification in the next reaction step.

b) A mixture of (0.002 mol) compound 5 and its nitrosoderivative (0.0020 mol) and 1,4-dimercapto-2,3-butanediol (0.0059 mol) in methanol (15 ml) was stirred at room temperature for 48 hours. The precipitate was filtered, washed with H₂O, with EtOH then with diethyl ether and dried. The residue was taken up in CH₃OH/THF/CH₂Cl₂. The precipitate was filtered off and dried. Yielding: 0.65 g compound 5 (46%).

Example B5

Preparation of (compound 6)

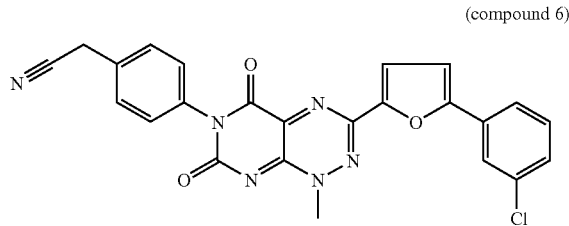

a) NaNO₂ (0.0026 mol) was added at 5° C. to a mixture of intermediate 16 (0.0017 mol) in AcOH (8 ml) and H₂O (0.8 ml). The mixture was brought to room temperature, then stirred for 20 days. Diethyl ether was added. The precipitate was filtered off and dried. Yielding: 1.5 g compound 6 (>100%) and the nitrosoderivative thereof.

b) A mixture of compound 6(0.0015 mol) and its nitrosoderivative (0.0015 mol) and 1,4-dimercapto-2,3-butanediol (0.0046 mol) in EtOH (15 ml) was stirred at room temperature for 5 days. The precipitate was filtered, washed twice with EtOH, then washed twice with H₂O, then with EtOH, diethyl ether and dried. This fraction was taken up in H₂O, washed with EtOH/THF and dried with diethyl ether. This fraction was taken up in H₂O, washed with methanol and dried with diethyl ether. This fraction was washed with H₂O/EtOH and dried with diethyl ether. Yielding: 0.21 g compound 6 (15%).

Example B6

Preparation of (compound 8)

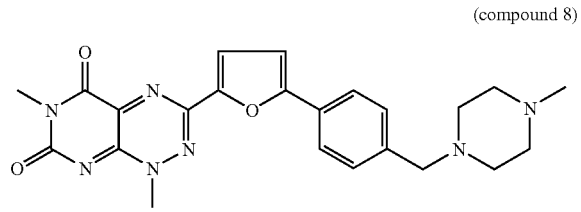

a) NaNO₂ (0.0082 mol) was added at 5° C. to a mixture of intermediate 22 (0.0027 mol) in AcOH (12 ml) and H₂O (1.2 ml). The mixture was brought to room temperature and stirred overnight. Diethyl ether was added. The precipitate was filtered off and dried. Yielding: 1.6 g compound 8 and the nitrosoderivative thereof (>100%). This product was used directly in the next reaction step.

b) A mixture of compound 8 (0.0013 mol) and its nitrosoderivative (0.0013 mol) and 1,4-dimercapto-2,3-butanediol (0.0051 mol) in ethanol (10 ml) was stirred at room temperature for 10 days. The precipitate was filtered, washed with EtOH, then with diethyl ether and dried. The residue (1 g) was purified by column chromatography over silica gel (eluent: CH₂Cl₂/CH₃OH 80/20; 15–40 μm). The pure fractions were collected and the solvent was evaporated. Yielding: 0.19 g fraction 1 and 0.6 g fraction 2 (38%). Part of F2 (0.25 g) was washed with K₂CO₃ 10% and extracted with CH₂Cl₂. The organic layer was separated, dried (MgSO₄), filtered, and the solvent was evaporated. Yielding: 0.08 g compound 9.

Example B7

Preparation of (compound 9)

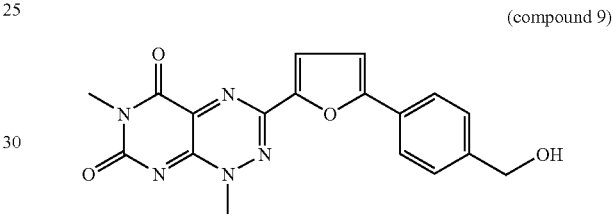

a) NaNO₂ (0.0033 mol) was added at 5° C. to a mixture of intermediate 21 (0.0022 mol) in AcOH (8 ml) and H₂O (0.8 ml). The mixture was brought to room temperature and stirred overnight. The precipitate was filtered. The filtrate was washed with diethyl ether and dried. Yielding: 1.2 g compound 9 and the nitrosoderivative thereof. This product was used without further purification.

b) A mixture of compound 9 (0.0015 mol) and its nitrosoderivative (0.0015 mol) and 1,4-dimercapto-2,3-butanediol (0.0047 mol) in methanol (10 ml) was stirred at room temperature for 4 days. The precipitate was filtered, washed with H₂O, twice with EtOH and dried with diethyl ether. Yielding: compound 10 (58%).

Example B8

Preparation of (compound 10)

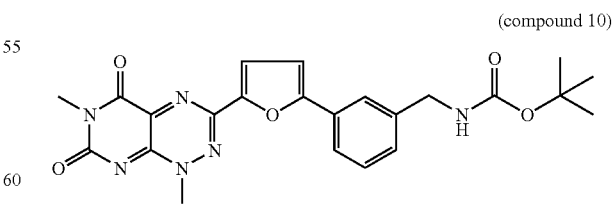

a) NaNO₂ (0.0065 mol) was added portionwise at 0° C. to a mixture of intermediate 26 (0.0059 mol) in AcOH (29 ml) and H₂O (1.06 ml). The mixture was stirred at room temperature overnight. The precipitate was filtered off and dried. Yielding: 2.06 g compound 10 (74%).

b) A mixture of compound 10 (0.0021 mol) and its nitrosoderivative (0.0021 mol) and 1,4-dimercapto-2,3-butanediol (0.0087 mol) in EtOH (178 ml) and THF (38 ml) was stirred at room temperature for 5 days. The precipitate was fitlered off and dried. Yielding: 1.2 g compound 10 (59%).

Example B9

Preparation of (compound 11)

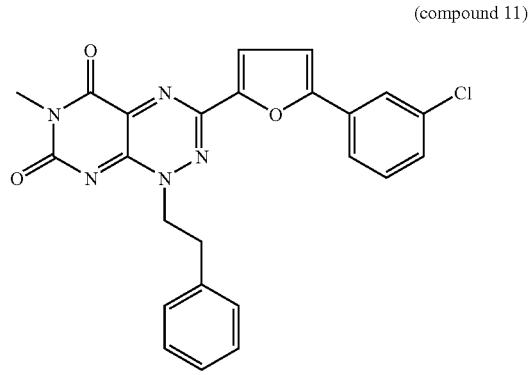

a) NaNO$_2$ (0.0033 mol) was added portionwise at 0° C. to a mixture of intermediate 28 (0.003 mol) in AcOH (16 ml) and H$_2$O (0.55 ml). The mixture was stirred at room temperature overnight. The precipitate was filtered off and dried. Yielding: 1.46 g nitorsoderivative (>100%).

b) A mixture of this nitrosoderivative (0.003 mol) and 1,4-dimercapto-2,3-butanediol (0.0061 mol) in EtOH (125 ml) and THF (26 ml) was stirred at room temperature for 3 days. The precipitate was filtered and purified by column chromatography over silica gel (eluent: CH$_2$Cl$_2$/EtOAc 80/20; 15–40 μm). The pure fractions were collected and the solvent was evaporated. Yielding: 0.65 g compound 11 (46%).

Example B10

Preparation of (compound 12)

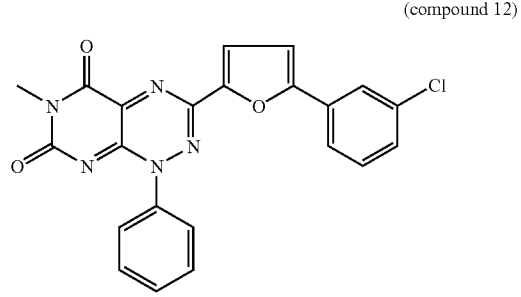

a) NaNO$_2$ (0.0045 mol) was added at a temperature between 0 and 5° C. to a mixture of intermediate 30 (0.0037 mol) in H$_2$O (0.65 ml) and AcOH (18 ml). The mixture was stirred at room temperature for 7 days. The precipitate was filtered, washed with diethyl ether and dried. Yielding: 1.24 g compound 12 and and the nitrosoderivative thereof b) A mixture of compound 12 (0.0014 mol) and its nitrosoderivative (0.0014 mol) and 1,4-dimercapto-2,3-bu-tanediol (0.0083 mol) in methanol (15 ml) was stirred at room temperature for 3 days. The precipitate was filtered, washed with CH$_3$OH, then with H$_2$O, then with methanol and dried. The residue (1 g) was purified by column chromatography over silica gel (eluent: CH$_2$Cl$_2$/CH$_3$OH 98/2; 15–40 μm). Two fractions were collected and the solvent was evaporated. Yielding: 0.3 g compound 13 (global yield: 58%).

Example B11

Preparation of (compound 13)

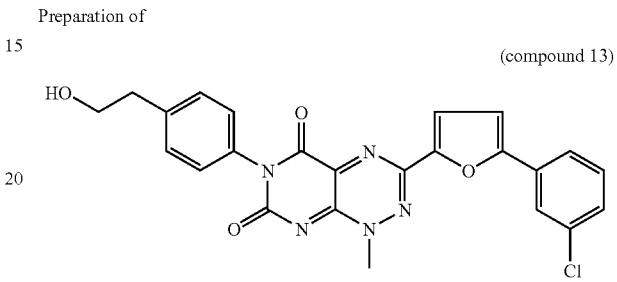

a) A mixture of intermediate 36 (0.0032 mol) in AcOH (15 ml) and H$_2$O (1.5 ml) was cooled to 5° C. NaNO$_2$ (0.0097 mol) was added. The mixture was brought to room temperature, then stirred at room temperature overnight. The precipitate was filtered, washed with EtOH, then with diethyl ether and dried. Yielding: compound 13 and the nitrosoderivative thereof. This product was used directly in the next reaction step.

b) A mixture of compound 13 (0.0018 mol) and its nitrosoderivative (0.0018 mol) and 1,4-dimercapto-2,3-butanediol (0.0056 mol) in EtOH (40 ml) was stirred at room temperature for 36 hours. The precipitate was filtered, washed twice with EtOH, then with diethyl ether and dried. Yielding: 1.1 g fraction 1 (61%). This fraction was dried at 40° C. in a vacuo. Yielding: 0.33 g fraction 2. This fraction was dried in a vacuo. Yielding: 0.3 g fraction 3. This fraction was taken up in diethyl ether. The precipitate was filtered off and dried. Yielding: 0.29 g fraction 4. This fraction was dried in a vacuo. Yielding:0.28 g fraction 5. This fraction was washed with H$_2$O, taken up in EtOH, washed again and dried. Yielding: 0.28 g compound 13.

Example B12

Preparation of (compound 14)

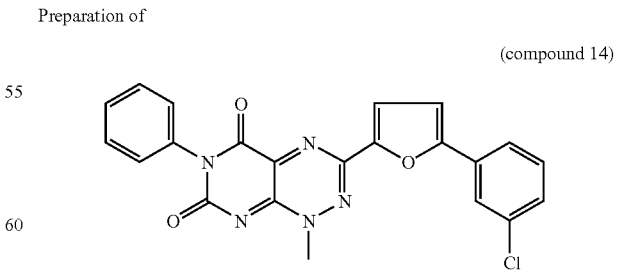

a) NaNO$_2$ (0.0064 mol) was added at 5° C. to a mixture of intermediate 36 (0.0042 mol) in AcOH (18 ml) and H$_2$O (0.9 ml). The mixture was stirred at room temperature for 48 hours and poured out into H$_2$O. The precipitate was filtered, washed with H₂O and dried. The residue was taken up in CH₂Cl₂ and washed with H₂O. The organic layer was separated, dried (MgSO₄), filtered, and the solvent was evaporated. Yielding: 1.6 g compound 14 and and the nitrosoderivative thereof (85%).

b) A mixture of compound 14 (0.0018 mol) and its nitrosoderivative (0.0018 mol) and 1,4-dimercapto-2,3-butanediol (0.0072 mol) in EtOH (30 ml) was stirred at room temperature for 15 days. The precipitate was filtered, washed with diethyl ether and dried. The residue (1 g) was taken up in EtOH (hot). The precipitate was filtered, washed with EtOH, then with diethyl ether and dried. Yielding: 0.6 g compound 14 (38%).

Example B13

Preparation of (compound 15)

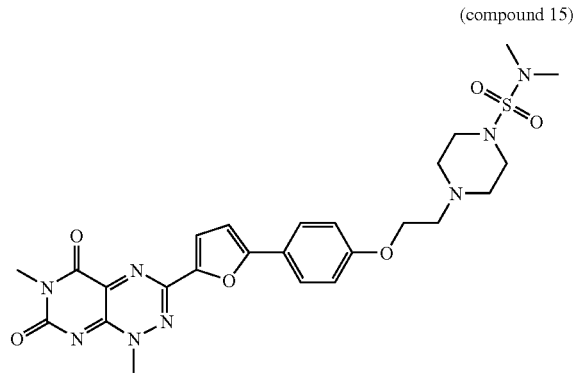

a) NaNO₂ (0.0056 mol) was added at 5° C. to a mixture of intermediate 40 (0.0037 mol) in AcOH (20 ml) and H₂O (0.65 ml). The mixture was stirred at room temperature for 5 hours. DIPE was added. The precipitate was filtered off and dried. Yielding: 2.6 g of compound 15 and its nitrosoderivative.

Preparation of (intermediate 57))

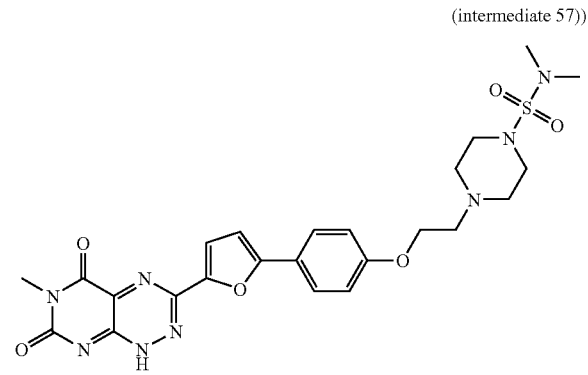

b) A mixture of compound 15 (0.0018 mol) and its nitrosoderivative (0.0018 mol) in DMF (20 ml) was stirred at 100° C. for 1 hour, then brought to room temperature. The precipitate was diluted in H₂O, filtered off and dried. Yielding: 1.8 g of intermediate 57

Preparation of (compound 16)

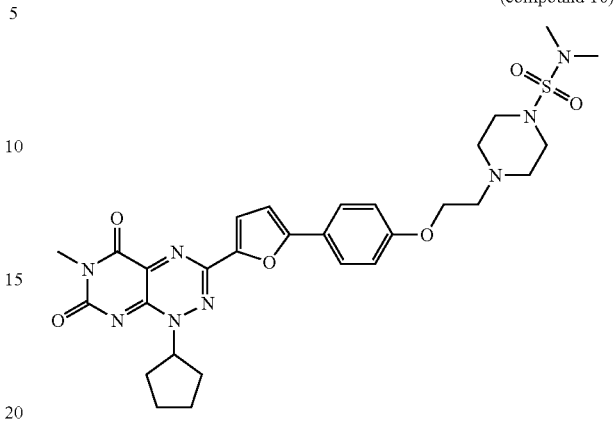

c) A mixture of intermediate 57 (0.0037 mol), bromocyclopentane (0.017 mol) and K₂CO₃ (0.011 mol) in dioxane (185 ml) was stirred at at 120° C. for 2 days, then brought to room temperature. The solvent was evaporated. The residue was taken up in H₂O. The mixture was extracted with CH₂Cl₂. The organic layer was separated, dried (MgSO₄), filtered, and the solvent was evaporated. The residue (2.4 g) was purified by column chromatography over silica gel (eluent: CH₂Cl₂/CH₃OH/98/2; 15–40 μm). The pure fractions were collected and the solvent was evaporated. Yielding: 0.069 of compound 16 (2.6%).

Example B14

Preparation of (compound 17)

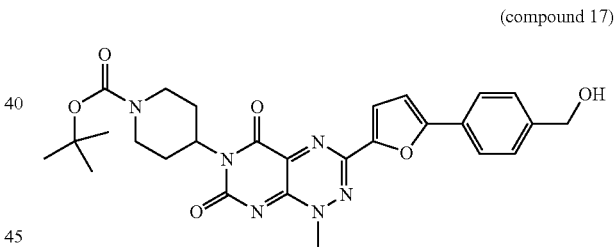

a) NaNO₂ (0.0217 mol) was added at 5° C. to a mixture of intermediate 47 (0.0145 mol) in AcOH (76 ml) and H₂O (3.8 ml). The mixture was stirred at room temperature for 6 hours. DIPE was added. The precipitate was filtered off and dried. Yielding: 6.4 g of compound 17 and its nitrosoderivative.

Preparation of (compound 58)

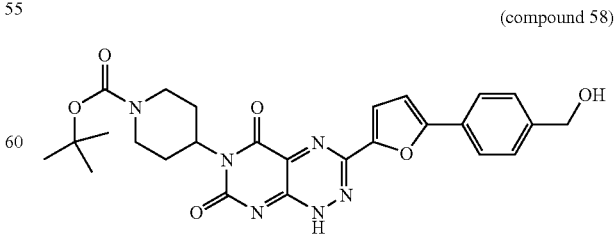

b) A mixture of compound 17 (0.0057 mol) and its nitrosoderivative (0.0057 mol) in DMF (60 ml) was stirred at 100° C. for 30 minutes, then brought to room temperature.

The precipitate was diluted in ice and H₂O, filtered off and dried. Yielding: 7.1 g of intermediate 58

Preparation of (compound 18)

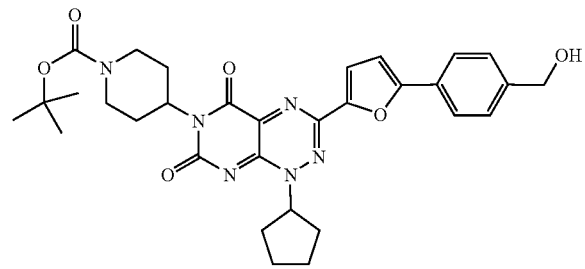

c) A mixture of intermediate 58 (0.0019 mol), bromocyclopentane (0.0076 mol) and K₂CO₃ (0.0057 mol) in dioxane (100 ml) was stirred and refluxed for 7 hours, then brought to room temperature. The solvent was evaporated. The residue was taken up in H₂O. The mixture was extracted with CH₂Cl₂. The organic layer was separated, dried (MgSO₄), filtered, and the solvent was evaporated. The residue (2.4 g) was purified by column chromatography over silica gel (eluent: CH₂Cl₂/CH₃OH/98/2; 15–40 μm). The pure fractions were collected and the solvent was evaporated. Yielding: 1.1 g of compound 18 (27%).

Preparation of (compound 19)

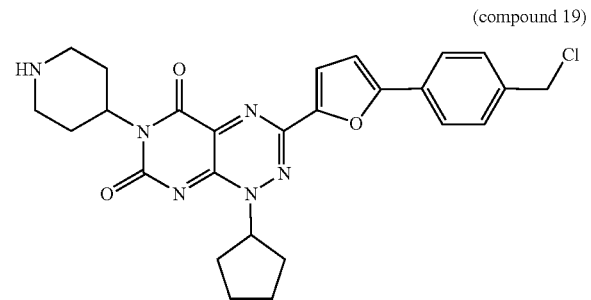

d) SOCl₂ (0.0067 mol) was added at room temperature to a mixture of compound 18 (0.0016 mol) in CH₂Cl₂ (20 ml). The mixture was stirred at room temperature for 4 hours. The solvent was evaporated. Yielding: 19 of compound 19. This product was used directly in the next reaction step.

Preparation of (compound 20)

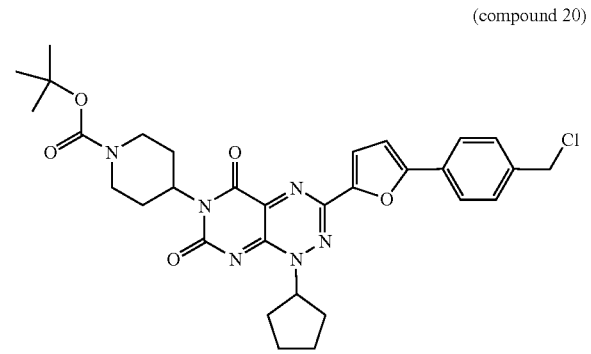

e) (Boc)₂O (0.0029 mol) was added portionwise to a mixture of compound 19 (0.0019 mol) in CH₂Cl₂ (50 ml). The mixture was stirred at room temperature for 1 hour. Ice and water were added. The organic layer was separated, dried (MgSO₄), filtered, and the solvent was evaporated. yielding: 1.15 g of compound 20. This product was used directly in the next reaction step.

Preparation of (compound 21)

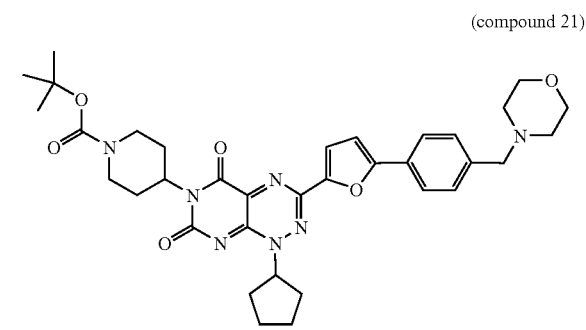

f) A mixture of compound 20 (0.0019 mol), morpholine (0.0038 mol) and Et₃N (0.0028 mol) in CH₃CN was stirred at room temperature for 12 hours, then at 80° C. for 3 hours, then brought to room temperature. The solvent was evaporated. The residue was taken up in CH₂Cl₂. The organic layer was washed with H₂O, dried (MgSO₄), filtered and the solvent was evaporated. The residue (1.6 g) was purified by column chromatography over silica gel (eluent: CH₂Cl₂/CH₃OH/98/2; 15–40 μm). The pure fractions were collected and the solvent was evaporated. Yielding: 0.15 g of compound 21 (16%).

Preparation of (compound 22)

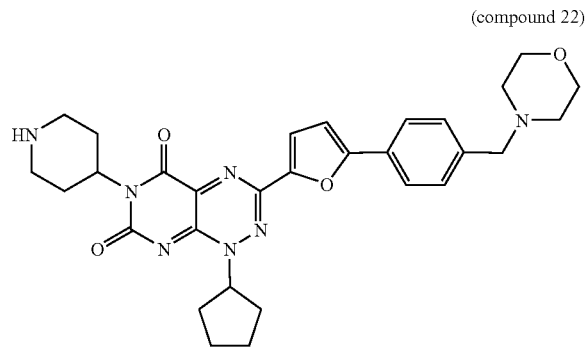

g) HCl/isopropanol 5/6N (0.2 ml) was added to a mixture of compound 21 (0.0001 mol) in isopropanol (1 ml). The mixture was stirred at 60° C. for 6 hours, then brought to room temperature. The precipitate was filtered off and dried with diethylether. Yielding: 0.073 g of compound 22 (76%).

Example B15

Preparation of (compound 23)

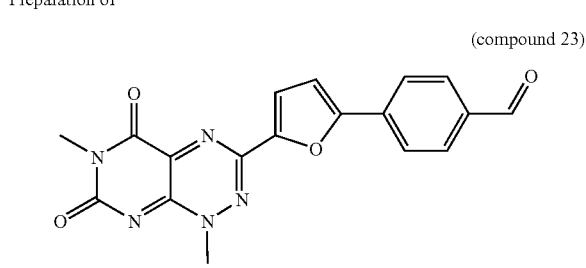

a) NaNO₂ (0.035 mol) was added at 5° C. to a mixture of intermediate 49 (0.0234 mol) in AcOH (100 ml) and H₂O (4.8 ml). The mixture was stirred at room temperature for 18 hours. DIPE was added. The precipitate was filtered off and dried. Yielding: 9.1 g of compound 23 and its nitrosoderivative.

Preparation of (intermediate 59)

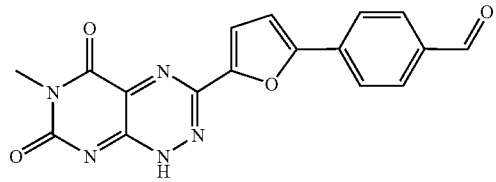

b) A mixture of compound 23 (0.0117 mol) and its nitrosoderivative (0.0117 mol) in DMF (70 ml) was stirred at 90° C. for 2 hours, then brought to room temperature. The precipitate was diluted in ice and H₂O, filtered off and dried. Yielding: 7.75 g of intermediate 59

Preparation of (compound 24)

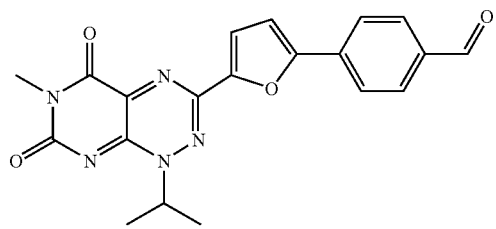

c) A mixture of intermediate 59 (0.0091 mol), 2-iodopropane (0.0412 mol) and K₂CO₃ (0.0394 mol) in dioxane (400 ml) was stirred and refluxed at 120° C. for 48 hours, then brought to room temperature. The solvent was evaporated. The residue was taken up in CH₂Cl₂. The mixture was extracted with CH₂Cl₂. The organic layer was separated, dried (MgSO₄), filtered, and the solvent was evaporated. The residue (3.2 g) was purified by column chromatography over silica gel (eluent: CH₂Cl₂/CH₃OH/98/2; 15–40 µm). The pure fractions were collected and the solvent was evaporated. Yielding: 0.7 g of compound 24 (20%).

Preparation of (compound 25)

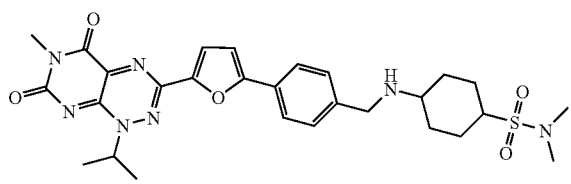

d) A mixture of compound 24 (0.0016 mol), 4-amino-1-dimethylaminosulfonyl-piperidine (0.002 mol) and NEt₃ in EtOH (50 ml) was stirred at 60° C. for 3 hours, then brought to room temperature. NaBH₄ (0.0033 mol) was added portionwise. The mixture was stirred at room temperature for 1 hour, poured out into H₂) and extracted with CH₂Cl₂. The organic layer was separated, dried (MgSO₄), filtered and the solvent was evaporated. The residue was taken up in EtOH. The precipitate was filtered off and dried. Yielding: 0.867 g of compound 25 (89%).

Example B16

Preparation of (compound 26)

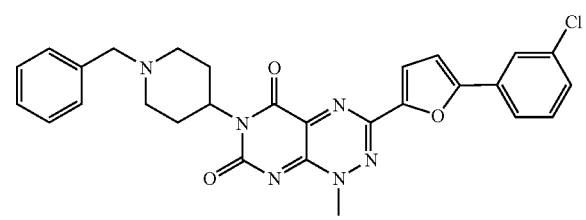

a) NaNO₂ (0.0021 mol) was added at 0° C. to a mixture of intermediate 53 (0.0019 mol) in AcOH (10 ml) and H₂O (0.36 ml). The mixture was stirred at room temperature for 24 hours, poured out on ice, basified with K₂CO₃ and extracted with CH₂Cl₂. The organic layer was separated, dried (MgSO₄), filtered and the solvent was evaporated. The residue was purified by column chromatography over silica gel (eluent: CH₂Cl₂/CH₃OH/98/2; 15–40 µm). The pure fractions were collected and the solvent was evaporated. Yielding: 0.19 g of compound 26 (19%)

Preparation of (intermediate 60)

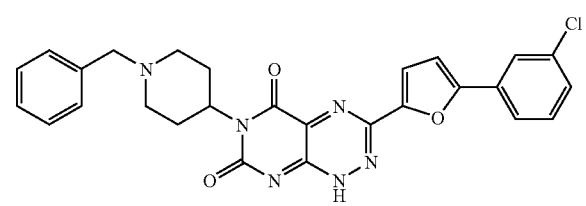

b) A mixture of compound 26 (0.013 mol) and its nitrosoderivative (0.013 mol) in DMF (100 ml) was stirred at 50° C. for 3 hours, then brought to room temperature. The residue was taken up in diethyl ether. The precipitate filtered off and dried. Yielding: 8.54 g of intermediate 60 (64%).

Preparation of (compound 27)

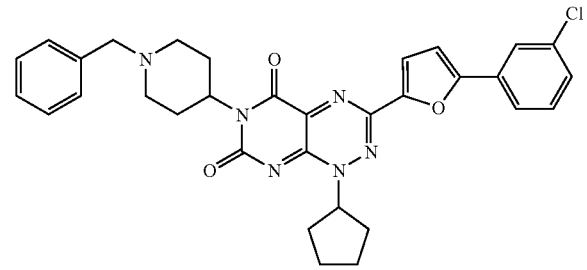

c) A mixture of intermediate 60 (0.0006 mol), bromocyclopentane (0.0023 mol) and K₂CO₃ (0.0018 mol) in dioxane (30 ml) was stirred and refluxed at 120° C. for 4 hours, then brought to room temperature. The solvent was evaporated. The residue was taken up in CH₂Cl₂. The mixture was extracted with CH₂Cl₂. The organic layer was separated, dried (MgSO₄), filtered, and the solvent was evaporated. The residue was taken up in EtOH. The precipitate was filtered off and dried. Yielding: 0.082 g of compound 27 (24%).

Preparation of (compound 28)

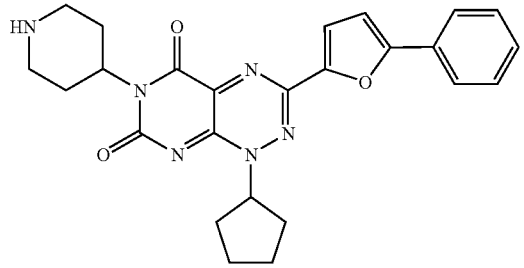

d) A mixture of compound 27 (0.0008 mol) and Pd(OH)₂ (0.04 g) in methanol (10 ml) was hydrogenated at room temperature for 50 hours under 60 PsI. The precipitate was filtered over celite. The filtrate was evaporated. The residue (0.44 g) was purified by column chromatography over silica gel (eluent: CH₂Cl₂/CH₃OH/NH₄OH 92/8/0.1; 15–40 µm). The pure fractions were collected and the solvent was evaporated. The residue (0.2 g, 50%) was taken up in DIPE. The precipitate was filtered off and dried. Yielding 0.13 g of compound 28).

Preparation of (compound 29)

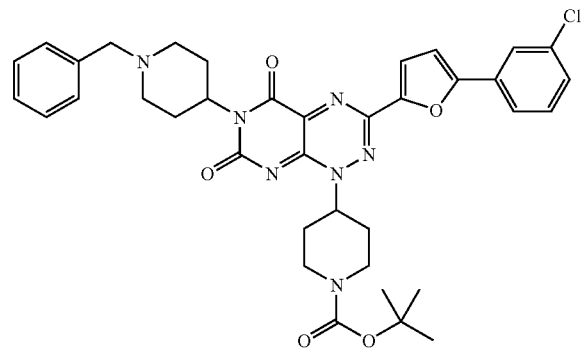

e) A mixture of intermediate 60 (0.0019 mol), tert-butyl-4-iodopiperidine-1-carboxylate (0.0058 mol) and K₂CO₃ (0.0038 mol) in dioxane (50 ml) was stirred and refluxed for 48 hours then filtered. The filtrate was evaporated. The residue was taken up in H₂O and extracted with CH₂Cl₂. The organic layer was separated, dried (MgSO₄), filtered, and the solvent was evaporated. The residue was purified by column chromatography over silica gel (eluent: CH₂Cl₂/CH₃OH/96/4; 15–40 µm). The pure fractions were collected and the solvent was evaporated. Yielding: 0.08 g of compound 29 (6%)

Preparation of (compound 30)

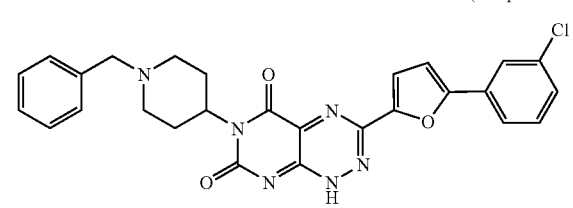

f) A mixture of compound 29 (0.0001 mol) in HCl 5–6N in isopropanol (0.2 ml) and isopropanol (10 ml) was stirred at 60° C. overnight. The precipitate was filtered off and dried. Yielding: 0.051 g of compound 30 (60%).

Example B17 a) Preparation of (compound 31)

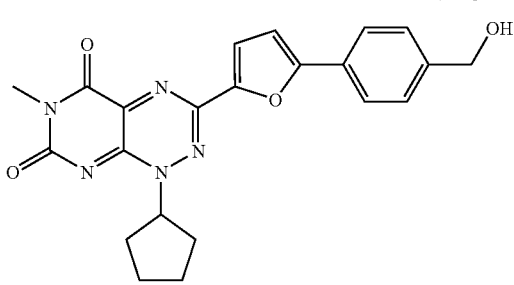

A mixture of intermediate 56 (0.0051 mol), bromocyclopentane (0.023 mol) and K₂CO₃ (0.0154 mol) in dioxane (180 ml) was stirred and refluxed at 120° C. for 48 hours, then brought to room temperature. The solvent was evaporated. The residue was taken up in CH₂Cl₂. The mixture was extracted with CH₂Cl₂. The organic layer was separated, dried (MgSO₄), filtered, and the solvent was evaporated. The residue (3.2 g) was purified by column chromatography over silica gel (eluent: CH₂Cl₂/CH₃OH/98/2; 15–40 µm). The pure fractions were collected and the solvent was evaporated. Yielding: 0.35 g of compound 31 (6.8%).

b) Preparation of (compound 32)

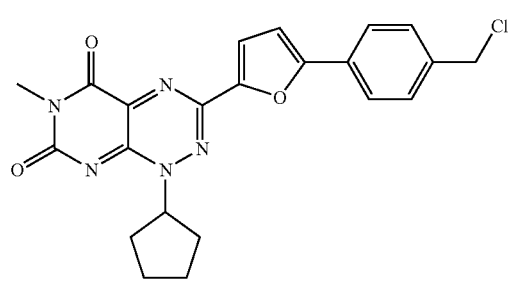

SOCl$_2$ (0.0033 mol) was added at room temperature to a mixture of compound 31 (0.0008 mol) in CH$_2$Cl$_2$ (16 ml). The mixture was stirred at room temperature for 2 hours. The solvent was evaporated. Yielding: 0.36 g of compound 32.

Preparation of (compound 33)

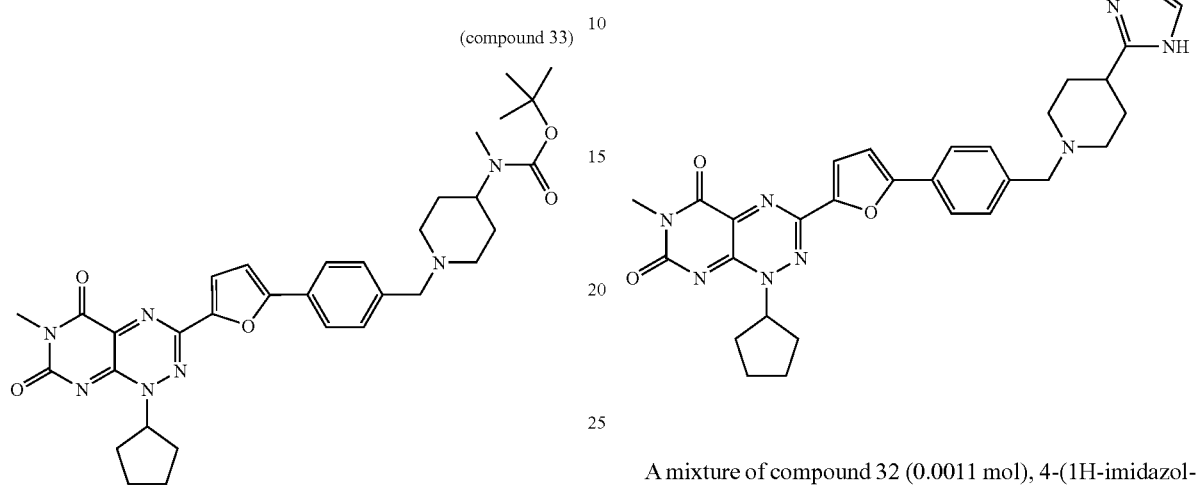

c) A mixture of compound 32 (0.0034 mol), 4-N-Boc-4-N-methyl-aminopiperidine (0.0034 mol) and K$_2$CO$_3$ (0.0034 mol) in CH$_3$CN (50 ml) was stirred at 50° C. overnight, then brought to room temperature. The solvent was evaporated yielding compound 33. This product was used directly in the next reaction step.

Preparation of (compound 34)

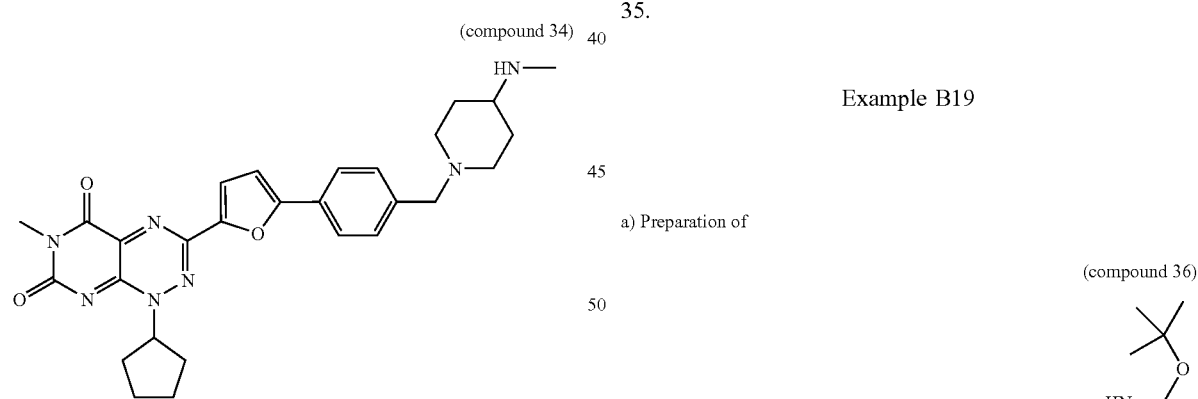

d) A mixture of compound 33 (0.0028 mol), HCl (5–6N) in isopropanol (3 ml) and isopropanol (50 ml) was heated up to reflux and stirred at 60° C. for 3 hours, then brought to room temperature. The crude reaction medium was purified by HPLC. The desired fractions were collected and the organic solvent was evaporated. The water layer was neutralized with K$_2$CO$_3$ and extracted with MeOH/CH$_2$Cl$_2$ (5/95). The organic layer was dried with MgSO$_4$, filtered and evaporated till dryness. The residue was stirred in DIPE. The precipitate was filtered off, washed and dried under vacuo at 50° C. Yielding 0.056 g of compound 34.

Example B18

Preparation of (compound 35)

A mixture of compound 32 (0.0011 mol), 4-(1H-imidazol-2-yl)-piperidine (0.0011 mol) and K$_2$CO$_3$ (0.0022 mol) in CH$_3$CN (15 ml) was stirred and refluxed at 50° C. overnight, then brought to room temperature. The crude reaction medium was purified by HPLC. The desired fractions were collected and the organic solvent was evaporated. The water layer was neutralized with K$_2$CO$_3$ and extracted with MeOH/CH$_2$Cl$_2$ (5/95). The organic layer was dried with MgSO$_4$, filtered and evaporated till dryness. The residue was stirred in DIPE. The precipitate was filtered off, washed and dried under vacuo at 60° C. Yielding 0.165 g of compound 35.

Example B19 a) Preparation of (compound 36)

A mixture of compound 32 (0.0022 mol), Boc-4-aminopiperidine (0.0022 mol) and K₂CO₃ (0.0022 mol) in CH₃CN (50 ml) was stirred and refluxed at 50° C. for 24 hours, then brought to room temperature. The solvent was evaporated yielding compound 36. This product was used directly in the next reaction step.

b) Preparation of (compound 37)

A mixture of compound 36 (0.0028 mol), HCl (5–6N) in isopropanol (3 ml) and isopropanol (50 ml) was heated up to reflux and stirred at 60° C. for 3 hours, then brought to room temperature. The crude reaction medium was purified by HPLC. The desired fractions were collected and the organic solvent was evaporated. The water layer was neutralized with K₂CO₃ and extracted with MeOH/CH₂Cl₂ (5/95). The organic layer was dried with MgSO₄, filtered and evaporated till dryness. The residue was stirred in DIPE. The precipitate was filtered off, washed and dried under vacuo at 50° C. Yielding 0.056 g of compound 37.

Example B20

Preparation of

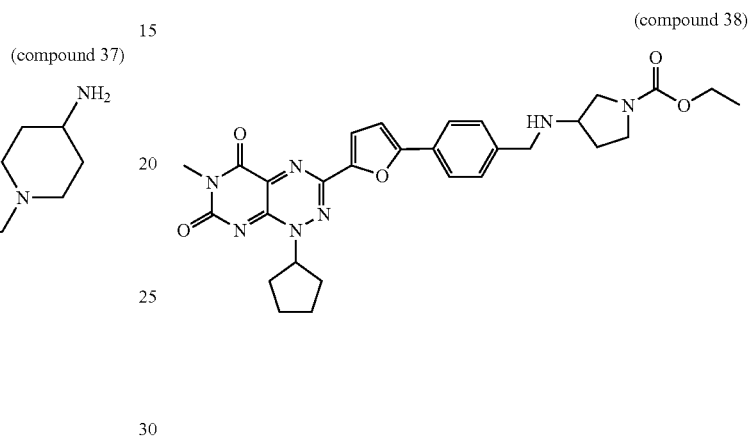

(compound 38)

A mixture of compound 32 (0.0010 mol), 1-pyrrolidinecarboxylic acid, 3-amino-, ethylester (0.0010 mol) and K₂CO₃ (0.0020 mol) in CH₃CN (15 ml) was stirred and refluxed at 50° C. overnight, then brought to room temperature. The crude reaction medium was purified by HPLC. The desired fractions were collected and the organic solvent was evaporated. The water layer was neutralized with K₂CO₃ and extracted with MeOH/CH₂Cl₂ (5/95). The organic layer was dried with MgSO₄, filtered and evaporated till dryness. The residue was stirred in DIPE. The precipitate was filtered off, washed and dried under vacuo at 50° C. Yielding 0.0261 g of compound 38.

Example B21 a) Preparation of

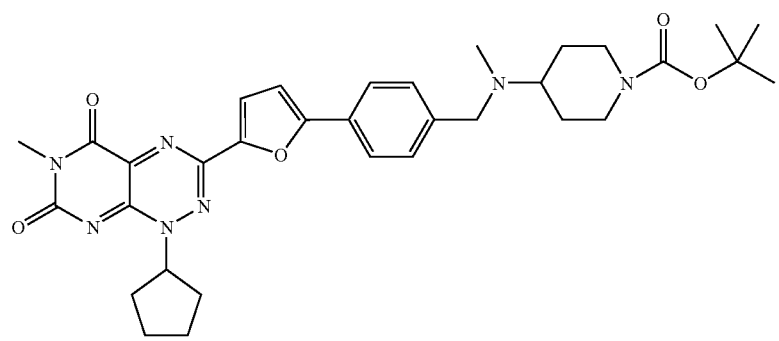

(compound 39)

A mixture of compound 32 (0.0010 mol), N-methyl-1-tert-butoxycarbonyl-4-piperidinamine (0.0010 mol) and K$_2$CO$_3$ (0.0020 mol) in CH$_3$CN (15 ml) was stirred and refluxed at 50° C. overnight, then brought to room temperature. The crude reaction medium was purified by HPLC. The desired fractions were collected and the organic solvent was evaporated. The water layer was neutralized with K$_2$CO$_3$ and extracted with MeOH/CH$_2$Cl$_2$ (5/95). The organic layer was dried with MgSO$_4$, filtered and evaporated till dryness. The residue was stirred in DIPE. The precipitate was filtered off, washed and dried under vacuo at 50° C. Yielding 0.0261 g of compound 39.

b) Preparation of (compound 40)

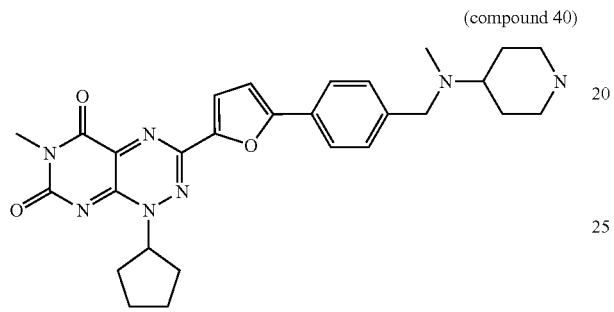

A mixture of compound 39 (0.0016 mol), HCl (5–6N) in isopropanol (1.5 ml) and isopropanol (15 ml) was heated up to reflux and stirred at 60° C. for 1 hour, then brought to room temperature. The solvent was removed under reduced pressure. The residue was stirred in DIPE. The precipitate was filtered off, washed and dried under vacuo at 50° C. Yielding 0.007 g of compound 40.

Example B22 a) Preparation of (compound 31)

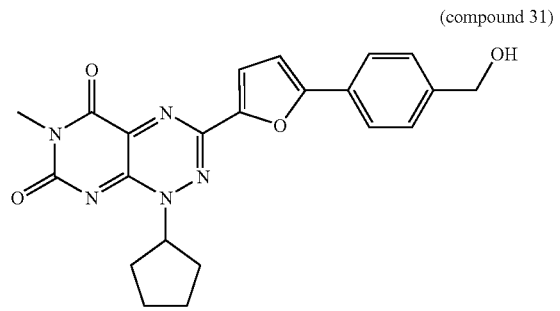

A solution of 5-phenyl-2-furaldehyde (0.030 mol), THF (250 ml) and Pd/C 10% (2 g) was stirred at room temperature and treated with H$_2$ for 15 minutes. The a solution of intermediate 62 (0.026 mol), thiophene (2 ml) and (Et)$_3$N (30 ml) was added drop wise over 2,5 hours. After addition, the reaction mixture was stirred further overnight under H$_2$ condition. The reaction mixture was filtered over decalite and the filtrate was concentrated under reduced pressure (=fraction 1). The residual fraction (decalite+compound 31) was stirred in DMF at 50° C., filtered over decalite, washed several times with DMF and concentrated under reduced pressure (=fraction 2). This fraction was stirred in Et$_2$O and the formed precipitate was filtered off, washed and dried. Yielding 7.3 g of compound 31 (67%).

b) Preparation of (compound 88)

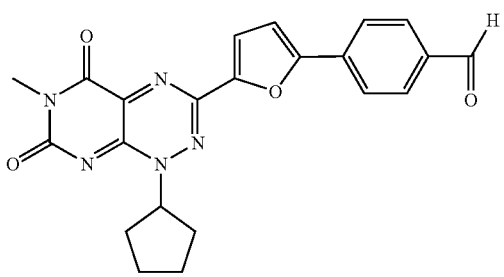

A mixture of compound 31, MnO$_2$ (2 g) and CH$_2$Cl$_2$ (200 ml) was stirred overnight at room temperature. An extra amount of MnO$_2$ (12 g) was added and stirred further for 1 day. The reaction was completed and filtered over decalite. The filtrate was concentrated under reduced pressure. The residual fraction was stirred in DIME, filtered, washed and dried under vacuum at 50° C. Yielding: 4 g of compound 88 (60%). The product was used as such in the next step.

c) Preparation of (compound 94)

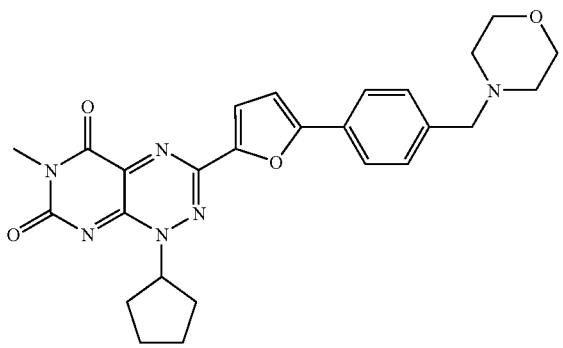

A mixture of thiophene (1 ml), Pd/C 10% (0.5 g), MeOH (50 ml) and THF (50 ml) was treated with H$_2$ for 15 minutes. Then compound 88 (0.004 mol) and morpholine (0.011 mol) were added at once and stirred further at room temperature under H$_2$ conditions for 18 hours. The reaction mixture was filtered over decalite and the filtrate was concentrated. The crude product was purified by HPLC, the desired fractions were collected and concentrated till the organic layer was removed. The water layer was neutralized with K$_2$CO$_3$ and the product was extracted with CH$_2$Cl$_2$. The organic layer was dried (MgSO$_4$), filtered and evaporated to dryness. The residual fraction was stirred in DIPE. The precipitate was filtered off and dried under vacuum at 50° C. Yielding: 1.5 g of compound 94 (97%).

Tables 1 & 2 list compounds of the present invention as prepared according to one of the above examples.

TABLE I

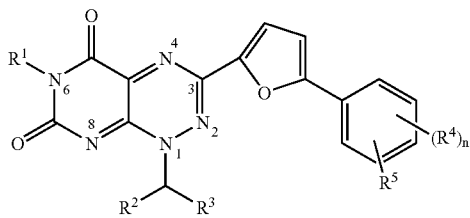

(I)

| Co. No. | R$^1$ | R$^2$ | R$^3$ | n | R$^4$ | R$^5$ | Physical data |
|---|---|---|---|---|---|---|---|
| 3 | CH$_3$ | H | H | 1 | 4-Cl | — | mp 253.8–284.8° C. |
| 7 | CH$_3$ | H | H | 1 | 3-Cl | — | — |
| 41 | CH$_3$ | H | H | 1 | 2-Cl | — | mp 228.5–290.2° C. |
| 42 | CH$_3$ | H | H | 1 | — | 2-NO$_2$ | — |
| 43 | CH$_3$ | H | H | 1 | 4-Br | — | — |
| 44 | CH$_3$ | H | H | 0 | — | 2-CF$_3$ | mp 179.1–185.9° C. |
| 45 | CH$_3$ | H | H | 0 | — | 3-CF$_3$ | mp 229.0–232.2° C. |
| 46 | CH$_3$ | H | H | 1 | 2-Cl | 5-CF$_3$ | mp 228.5–232.8° C. |
| 47 | CH$_3$ | H | H | 2 | 2,6(—Cl)$_2$ | 4-CF$_3$ | — |
| 48 | CH$_3$ | H | H | 1 | 4-Cl | — | mp 270.2–328.3° C. |
| 49 | CH$_3$ | H | H | 1 | 3-Cl | — | mp 256.8–322.6° C. |
| 50 | CH$_3$ | H | H | 1 | 2-Cl | — | — |
| 51 | CH$_3$ | H | H | 0 | — | 2-CF$_3$ | mp 205.3–212.3° C. |
| 52 | CH$_3$ | H | H | 0 | — | 3-CF$_3$ | mp 254.4–285.1° C. |
| 53 | CH$_3$ | H | H | 1 | 2-Cl | 5-CF$_3$ | mp 236.8–295.0° C. |
| 54 | CH$_3$ | H | H | 0 | — | 2-NO$_2$ | — |
| 55 | CH$_3$ | H | H | 2 | 2,6(Cl)$_2$ | 4-CF$_3$ | — |
| 56 | CH$_3$ | H | H | 2 | 2,4(Cl)$_2$ | — | — |
| 57 | CH$_3$ | H | H | 2 | 2,5(Cl)$_2$ | — | — |
| 58 | CH$_3$ | H | CH$_3$ | 1 | 3-Cl | — | mp 218.9–312.5° C. |
| 59 | CH$_3$ | H | CH$_3$ | 0 | — | 2-NO$_2$ | — |
| 60 | CH$_3$ | H | CH$_3$ | 1 | 2-Cl | — | — |
| 61 | CH$_3$ | H | —CH$_2$—OH | 1 | 3-Cl | — | — |
| 62 | 4-pyridyl-CH$_2$ | H | H | 1 | 3-Cl | — | mp 206.9–303.4° C. |
| 63 | C$_2$H$_5$—O—C(O)— | H | H | 1 | 3-Cl | — | mp 244.3–249.5° C. |
| 64 | morpholino-N—(CH$_2$)$_2$— | H | H | 1 | 3-Cl | — | mp 204.8–211.3° C. |
| 65 | H | H | H | 1 | 4-Cl | — | — |
| 14 | H | H | H | 1 | 3-Cl | — | mp 243.3–263.4° C. |
| 66 | 3-O$_2$N-C$_6$H$_4$-CH$_2$ | H | H | 1 | 3-Cl | — | mp 217.6–225.0° C. |
| 13 | 4-C$_2$H$_4$OH | H | H | 1 | 3-Cl | — | mp 180.6–230.5° C. |

TABLE I-continued (I)

| Co. No. | R¹ | R² | R³ | n | R⁴ | R⁵ | Physical data |
|---|---|---|---|---|---|---|---|
| 10 | CH₃ | H | H | 0 | — | 3-CH₂—NH—C(=O)—O—C(CH₃)₃ | mp 200.5–341.3° C. |
| 11 | CH₃ | H | —CH₂—C₆H₅ | 1 | 3-Cl | — | mp 203.4–215.1° C. |
| 9 | CH₃ | H | H | 1 | 4-CH₂OH | — | mp 246.3–300.7° C. |
| 26 | benzyl-4-methylpiperidine | H | H | 1 | 3-Cl | — | mp 210.4–241.0° C. |
| 67 | CH₃ | CH₃ | C₆H₅ | 1 | 3-Cl | — | — |
| 8 | CH₃ | H | H | 0 | — | 4-CH₂—N(4-methylpiperazine) | mp 189.0–278.5° C. |
| 69 | CH₃ | H | H | 0 | — | 4-CH₂—N(2-methylmorpholine) | mp 216.4–227.1° C. |
| 70 | CH₃ | CH₃ | (CH₂)₂—CH₃ | 1 | 3-Cl | — | mp 268.3–275.0° C. |
| 71 | CH₃ | CH₃ | C₃H₇ | 1 | 3-Cl | — | — |
| 6 | 4-CH₂—C≡N | H | H | 1 | 3-Cl | — | mp 241.1–244.8° C. |
| 72 | CH₃ | C₆H₅ | C₆H₅ | 1 | 3-Cl | — | mp 251.0–254.1° C. |
| 73 | CH₃ | C₆H₅ | C₆H₅ | 1 | 3-Cl | — | mp >260° C. |
| 74 | CH₃ | CH₃ | CH₃ | 1 | 3-Cl | — | — |
| 75 | CH₃ | CH₃ | CH₂—C₆H₅ | 1 | 3-Cl | — | mp 272.6–276.3° C. |
| 76 | CH₃ | CH(CH₃)₂ | C₆H₅ | 1 | 3-Cl | — | mp >250° C. |
| 5 | CH₃ | H | H | 1 | 3-CH₂OH | — | mp 223.7–227.7° C. |
| 4 | CH₃ | H | H | 0 | — | 4-S(=O)₂—N(morpholine) | mp 264.3–273.4° C. |
| 2 | CH₃ | H | H | 0 | — | 3-CH₂—NH—S(=O)₂—CH₃ | mp 215.1–236.6° C. |
| 1 | CH₃ | H | H | 0 | — | 3-CH₂—N(morpholine) | mp 209.3–219.8° C. |

TABLE I-continued

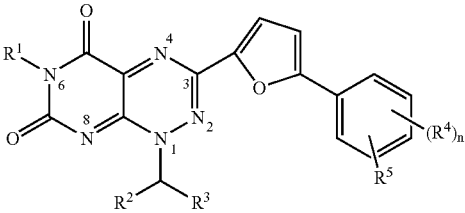

(I)

| Co. No. | R¹ | R² | R³ | n | R⁴ | R⁵ | Physical data |
|---|---|---|---|---|---|---|---|
| 77 | CH₃ | H | H | 0 | — | 4-CH₂-N(piperidine)-OH | — |
| 23 | CH₃ | H | H | 0 | — | 4-formyl | — |
| 78 | CH₃ | CH₃ | CH₃ | 0 | — | 4-CH₂-morpholine | 247.4–254.5° C. |
| 17 | (H₃C)₃C—O—C(=O)— | H | H | 1 | 4-CH₂OH | — | — |
| 79 | CH₃ | H | H | 0 | — | 4-O—C₂H₄-morpholine | — |
| 80 | CH₃ | H | H | 0 | — | 4-O—CH₂—C(=O)-N(piperazine)N—CH₃ | — |
| 81 | CH₃ | H | H | 0 | — | 4-O—C₂H₄-N(piperazine)N—CH₃ | — |
| 15 | CH₃ | H | H | 0 | — | 4-O—C₂H₄-N(piperazine)N—S(=O)₂—N(CH₃)₂ | — |
| 82 | CH₃ | CH₃ | CH₃ | 2 | 3,5 methoxy | 4-O—(CH₂)₂-N(piperidine) | mp 204.2–210.7° C. |
| 83 | CH₃ | CH₃ | CH₃ | 2 | 3,5 methoxy | 4-O—(CH₂)₂-morpholine | mp 215.5–222.6° C. |
| 84 | CH₃ | CH₃ | CH₃ | 0 | — | 4-CH₂OH | mp >250° C. |
| 85 | CH₃ | CH₃ | CH₃ | 0 | — | 4-CH₂Cl | — |
| 86 | CH₃ | CH₃ | CH₃ | 0 | — | 4-CH₂-N(piperazine)N—CH₃ | mp 225.3–228.9° C. |
| 87 | CH₃ | CH₃ | CH₃ | 0 | — | 4-CH₂-N(CH₃)—(CH₂)₂—OH | mp 229° C. |
| 24 | CH₃ | H | H | 0 | — | 4-CH=O | — |

TABLE I-continued (I)

[Structure: R¹-N⁶ fused pyrimidine-triazine system with carbonyl groups, connected via position 3 to furan-phenyl-(R⁴)ₙ with R⁵ substituent; N¹ bears CHR²R³ group]

| Co. No. | R¹ | R² | R³ | n | R⁴ | R⁵ | Physical data |
|---|---|---|---|---|---|---|---|
| 25 | CH₃ | CH₃ | CH₃ | 0 | — | 4-CH₂—NH—[piperidine]-N-SO₂-N(CH₃)₂ | mp 270.5–298.9° C. |
| 68 | CH₃ | CH₃ | CH₃ | 0 | — | 4-CH₂—N(CH₃)—[piperidine]-N-SO₂-NH₂ | — |

TABLE 2

(I)

[Same core structure (I) with R² and R³ joined as a ring]

| Co. No. | R¹ | R² R³ | n | R⁴ |
|---|---|---|---|---|
| 89 | CH₃ | (CH₂)₄ | 1 | 3-Cl |
| 90 | CH₃ | (CH₂)₆ | 1 | 3-Cl |
| 91 | CH₃ | (CH₂)₇ | 1 | 3-Cl |
| 92 | CH₃ | (CH₂)₅ | 1 | 3-Cl |
| 93 | CH₃ | (CH₂)₄ | 0 | — |
| 94 | CH₃ | (CH₂)₄ | 0 | — |
| 95 | CH₃ | (CH₂)₂—N(CO-O-C(CH₃)₃)—(CH₂)₂ | 1 | 3-Cl |
| 96 | CH₃ | (CH₂)₂—NH—(CH₂)₂ | 1 | 3-Cl |
| 97 | CH₃ | (CH₂)₄ | 0 | — |
| 27 | C₆H₅—CH₂—N[4-methylpiperidine] | (CH₂)₄ | | 3-Cl |
| 98 | CH₃ | (CH₂)₄ | 0 | — |
| 31 | CH₃ | (CH₂)₄ | 0 | — |
| 32 | CH₃ | (CH₂)₄ | 0 | — |
| 99 | CH₃ | (CH₂)₄ | 0 | — |
| 100 | CH₃ | (CH₂)₂—N(SO₂CH₃)—(CH₂)₂ | 1 | 3-Cl |

TABLE 2-continued (I)

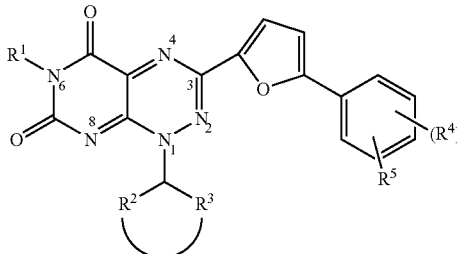

| # | R¹ / R²R³ group | chain | n | R⁴ |
|---|---|---|---|---|
| 101 | CH₃ | (CH₂)₂—N(SO₂N(CH₃)₂)—(CH₂)₂ | 1 | 3-Cl |
| 29 | C₆H₅—CH₂—N-piperidinyl-4-yl | (CH₂)₂—N(CO-O-C(CH₃)₃)—(CH₂)₂ | 1 | 3-Cl |
| 30 | C₆H₅—CH₂—N-piperidinyl-4-yl | (CH₂)₂—NH—(CH₂)₂ | 1 | 3-Cl |
| 102 | CH₃— | (CH₂)₂—N(SO₂N(CH₃)₂)—(CH₂)₂ | 0 | — |
| 103 | CH₃ | (CH₂)₄ | 0 | — |
| 104 | CH₃ | (CH₂)₄ | 0 | — |
| 105 | CH₃ | (CH₂)₄ | 0 | — |
| 28 | (CH₂)₂—N(SO₂N(CH₃)₂)—(CH₂)₂ | (CH₂)₄ | 0 | — |
| 106 | CH₃ | (CH₂)₄ | 0 | — |
| 107 | CH₃ | (CH₂)₄ | 0 | — |
| 108 | CH₃ | (CH₂)₂—N(CO-O-C(CH₃)₃)—(CH₂)₂ | 0 | — |
| 109 | CH₃ | (CH₂)₂—NH—(CH₂)₂ | 0 | — |
| 110 | CH₃ | (CH₂)₂—N(SO₂CH₃)—(CH₂)₂ | 0 | — |
| 111 | CH₃ | (CH₂)₄ | 0 | — |
| 112 | CH₃ | (CH₂)₄ | 0 | — |
| 113 | CH₃ | (CH₂)₄ | 0 | — |
| 114 | CH₃ | (CH₂)₂—N(SO₂NH₂)—(CH₂)₂ | 1 | 3-Cl |
| 115 | CH₃ | (CH₂)₄ | 0 | — |
| 33 | CH₃ | (CH₂)₄ | 0 | — |
| 34 | CH₃ | (CH₂)₄ | 0 | — |
| 35 | CH₃ | (CH₂)₄ | 0 | — |
| 116 | CH₃ | (CH₂)₄ | 0 | — |
| 36 | CH₃ | (CH₂)₄ | 0 | — |
| 37 | CH₃ | (CH₂)₄ | 0 | — |
| 18 | 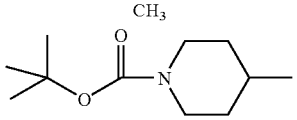 (tert-butoxycarbonyl-4-methylpiperidinyl) | (CH₂)₄ | 0 | — |
| 117 | CH₃ | (CH₂)₄ | 0 | — |
| 118 | CH₃ | (CH₂)₄ | 0 | — |
| 119 | CH₃ | (CH₂)₄ | 0 | — |
| 120 | CH₃ | (CH₂)₄ | 0 | — |

TABLE 2-continued

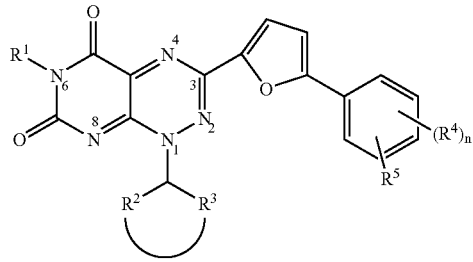

(I)

| Co. No. | R¹ | (R²,R³) | n | R⁴ |
|---|---|---|---|---|
| 19 | 4-piperidinyl (HN-piperidine) | (CH$_2$)$_4$ | 1 | 4-Cl |
| 20 | N-Boc-4-piperidinyl | (CH$_2$)$_4$ | 1 | 4-Cl |
| 21 | N-Boc-4-piperidinyl | (CH$_2$)$_4$ | 0 | — |
| 121 | CH$_3$ | (CH$_2$)$_4$ | 0 | — |
| 122 | CH$_3$ | (CH$_2$)$_4$ | 0 | — |
| 123 | CH$_3$ | (CH$_2$)$_4$ | 0 | — |
| 124 | CH$_3$ | (CH$_2$)$_4$ | 0 | — |
| 38 | CH$_3$ | (CH$_2$)$_4$ | 0 | — |
| 39 | CH$_3$ | (CH$_2$)$_4$ | 0 | — |
| 40 | CH$_3$ | (CH$_2$)$_4$ | 0 | — |
| 125 | CH$_3$ | (CH$_2$)$_4$ | 0 | — |
| 126 | CH$_3$ | (CH$_2$)$_4$ | 0 | — |
| 127 | CH$_3$ | (CH$_2$)$_2$—N(C(=NH)NH$_2$)—(CH$_2$)$_2$ | 1 | 3-Cl |
| 128 | CH$_3$ | (CH$_2$)$_4$ | 0 | — |
| 129 | CH$_3$ | (CH$_2$)$_4$ | 0 | — |
| 16 | CH$_3$ | (CH$_2$)$_2$ | 0 | — |
| 130 | CH$_3$ | (CH$_2$)$_4$ | 0 | — |
| 22 | 4-piperidinyl (HN-piperidine) | (CH$_2$)$_4$ | 0 | — |
| 131 | CH$_3$ | (CH$_2$)$_4$ | 0 | — |
| 132 | CH$_3$ | (CH$_2$)$_4$ | 0 | — |
| 133 | CH$_3$ | (CH$_2$)$_4$ | 0 | — |
| 134 | CH$_3$ | (CH$_2$)$_4$ | 0 | — |
| 135 | CH$_3$ | (CH$_2$)$_4$ | 2 | 3,5-methoxy |
| 136 | CH$_3$ | (CH$_2$)$_2$—N(C(=O)C$_6$H$_5$)—(CH$_2$)$_2$ | 0 | — |

| Co. No. | R⁵ | Physical data |
|---|---|---|
| 89 | — | mp >250° C. |
| 90 | — | mp >250° C. |
| 91 | — | mp >250° C. |
| 92 | — | mp >250° C. |
| 93 | 4-SO$_2$-morpholine | mp >250° C. |
| 94 | 4-CH$_2$-morpholine | mp 255° C. |

TABLE 2-continued (I)

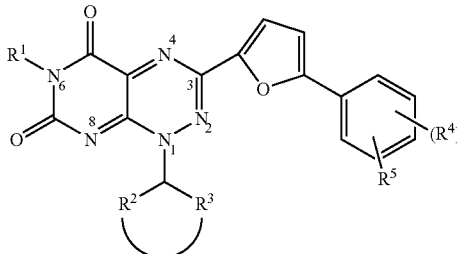

| # | | mp |
|---|---|---|
| 95 | — | mp >250° C. |
| 96 | — | mp >250° C. |
| 97 | 4-CH₂—NH—S(=O)₂—CH₃ | mp >250° C. |
| 27 | — | — |
| 98 | 3-CH₂—N(morpholine) | mp 155° C. |
| 31 | 4-CH₂OH | mp 182° C. |
| 32 | 4-CH₂Cl | — |
| 99 | 4-CH₂—N(piperazine)—CH₃ | mp 220° C. |
| 100 | — | mp >250° C. |
| 101 | — | mp >250° C. |
| 29 | — | — |
| 30 | — | — |
| 102 | — | mp 275.9° C. |
| 103 | 4-CH₂—N(piperidine)—OH | mp >250° C. |
| 104 | 4-CH₂—N(piperazine)—C(=O)—O—C(CH₃)₃ | mp 170° C. |
| 105 | 4-CH₂—N(piperazine)—NH | mp >276.5–308.40C |
| 28 | — | — |
| 106 | 4-CH₂—N(piperazine)—N—(CH₂)₂—OH | mp 175° C. |
| 107 | 4-CH₂—N(CH₃)—(CH₂)₂—OH | mp >250° C. |
| 108 | 4-CH₂—N(morpholine) | |
| 109 | 4-CH₂—N(morpholine) | |
| 110 | 4-CH₂—N(morpholine) | mp 177° C. |
| 111 | 3-CH=O | mp 248° C. |
| 112 | 4-CH₂—N(piperazine)—N—S(=O)₂—NH₂ | mp >250° C. |
| 113 | 4-CH₂—NH—(CH₂)₂OH | mp 240° C. |
| 114 | — | mp >250° C. |
| 115 | 4-CH₂—NH—O—CH₃ | mp 140° C. |

TABLE 2-continued

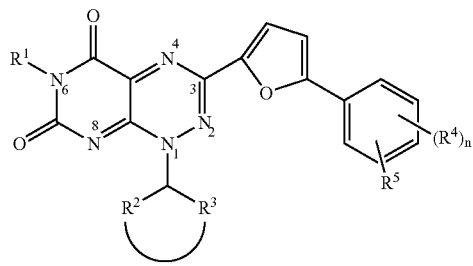

(I)

| # | | |
|---|---|---|
| 33 | 4-CH₂—N(piperidine)—N(CH₃)—C(=O)—O—C(CH₃)₃ | — |
| 34 | 4-CH₂—N(piperidine)—NH—CH₃ | — |
| 35 | 4-CH₂—N(piperidine)—(1H-imidazol-2-yl) | — |
| 116 | 4-CH₂—N(piperazine)—(1,4,5,6-tetrahydropyrimidin-2-yl) | mp 200.2° C. |
| 36 | 4-CH₂—N(piperidine)—NH—C(=O)—O—C(CH₃)₂ | — |
| 37 | 4-CH₂—N(piperidine)—NH₂ | — |
| 18 | 4-CH₂OH | — |
| 117 | 4-O—(CH₂)₂—N(morpholine) | mp 173° C. |
| 118 | 4-CH₂—N(piperazine)—S(=O)₂—N(CH₃)₂ | mp >250° C. |
| 119 | 4-O—CH₂—C(=O)—N(piperazine)—CH₃ | mp 252° C. |
| 120 | 4-O—(CH₂)₂—N(piperazine)—CH₃ | mp 196° C. |
| 19 | — | — |
| 20 | — | — |
| 21 | 4-CH₂—N(morpholine) | — |
| 121 | 4-CH₂—N(piperazine)—(CH₂)₂—O—(CH₂)₂—OH | mp >250° C. |
| 122 | 4-CH₂—NH—CH₂—(pyridin-3-yl) | mp 205° C. |
| 123 | 4-(piperidine)—N—C(=O)—O—C(CH₃)₃ | mp >250° C. |

TABLE 2-continued (I)

| | R² R³ structure | mp |
|---|---|---|
| 124 | 4-CH₂—N(piperidin-4-yl)—NH—S(O)₂—N(CH₃)₂ | mp >236.3° C. |
| 38 | 4-CH₂—NH—(pyrrolidin-3-yl), N-C(O)—O—C₂H₅ | — |
| 39 | 4-CH₂—N(CH₃)—(piperidin-4-yl), N-C(O)—O—C(CH₃)₃ | — |
| 40 | 4-CH₂—N(CH₃)—(piperidin-4-yl)NH | — |
| 125 | 4-CH₂—NH—(piperidin-4-yl), N—S(O)₂—N(CH₃)₂ | — |
| 126 | 4-CH₂—NH—C(CH₂OH)₃ | mp 241° C. |
| 127 | — | mp >260° C. |
| 128 | 4-(piperazin-1-yl), N-C(=O)—O—C(CH₃)₃ | mp 240° C. |
| 129 | 4-(piperazin-1-yl)NH | mp >250° C. |
| 16 | 4-O—CH₂CH₂—(piperazin-1-yl), N—S(O)₂—N(CH₃)₂ | — |
| 130 | 4-CH₂—N(piperidinyl) | mp >260° C. |
| 22 | 4-CH₂—N(morpholinyl) | — |
| 131 | 4-CH₂—N(pyrrolidinyl) | mp 218° C. |
| 132 | 4-CH₂—N(4-methoxypiperidin-1-yl) | mp 220° C. |

TABLE 2-continued (I)

[Structure of compound with R¹, N⁶, N⁴, N³, N², N¹, N⁸, O, furan, phenyl ring with (R⁴)ₙ and R⁵, R², R³ substituents]

| | | |
|---|---|---|
| 133 | 4-CH$_2$—N(piperazine)N—(CH$_2$)$_2$—O—CH$_3$ | mp 186° C. |
| 134 | 4-CH$_2$—N(C$_2$H$_4$OH)$_2$ | mp 242° C. |
| 135 | 4-O—C$_2$H$_4$—N(morpholine)O | mp 203.8–224.9° C. |
| 136 | 4-CH$_2$—N(piperazine)N—(CH$_2$)$_2$—O—CH$_3$ | — |

C. PHARMACOLOGICAL EXAMPLES

Example C.1

In Vitro Inhibition of cdk4 using a Scintillant Proximity Assay

The scintillant proximity assay (SPA) is in general described in U.S. Pat. No. 4,568,649 (Amersham Pharmacia Biotech). In the present cdk4 SPA kinase reaction assay, a kinase substrate consisting of a fragment of the restinoblastoma protein (pRb) tagged with glutathione-5-transferase (GST), is incubated with the aforementioned protein in the presence of ($^{33}$P) radiolabeled ATP. ($^{33}$P) phosporylation of the substrate is subsequently measured as light energy emitted using glutathione-coated SPA beads (Amersham Pharmacia Biotech) by trapping and quantifying the binding of the GST tagged and radiolabeled restinoblastoma protein.

DETAILED DESCRIPTION

The CDK4 SPA kinase reaction is performed at room temperature for 30 minutes in a 96-well microtiter plate. For each of the tested compounds a full dose response —$10^{-5}$M to $3.10^{-9}$M—has been performed. Flavopiridol was used as reference compound. The 100 µl reaction volume contains 50 mM Hepes, 10 mM NaF, 10 mM MgCl$_2$, 1 mM Na$_3$VO$_4$ pH 7.5, 1.5 µg CDK4-cell lysate/well, 0.2 µM unlabeled ATP, 1.7 µg/well GST-pRb, 1.7 nM AT$^{33}$P and 1 µl of a DMSO solution. The reaction is stopped by diluting the reaction mixture ½ with 0.1 mM Na$_2$EDTA, 0.1 mM non-labeled ATP, 0.05% Triton-X-100 and 10 mg/ml glutathion coated beads in PBS. The microtiterplates are centrifuges at 900 rpm for 10 minutes and the amount of phosphorylated ($^{33}$P) pRb is determined by counting (1 min/well) in a microtiterplate scintillation counter.

Example C.2

In Vitro Inhibition of AKT3 using a Scintillant Proximity Assay

The scintillant proximity assay (SPA) is in general described in U.S. Pat. No. 4,568,649 (Amersham Pharmacia Biotech). In the present AKT3 SPA kinase reaction assay, a kinase substrate consisting of a fragment of histone H$_2$B tagged with biotine, is incubated with the aforementioned protein in the presence of ($^{33}$P) radiolabeled ATP. ($^{33}$P) phosporylation of the substrate is subsequently measured as light energy emitted using streptavidine coated SPA beads (Amersham Pharmacia Biotech) by trapping and quantifying the binding of the biotine tagged and radiolabeled histone H2B fragment.

DETAILED DESCRIPTION

The AKT3 SPA kinase reaction is performed at 25° C. for 3 hrs in a 96-well microtiter plate. For each of the tested compounds a full dose response—$10^{-5}$M to $3.10^{-9}$M—has been performed. Staurosporine was used as reference compound [$10^{-7}$M to $10^{-9}$M]. The assays were performed in the presence of 25 mM Hepes, pH 7.0, containing 15 mM MgCl$_2$, 1 mM DTT Each assay was performed in a 100 µl reaction volume containing 111 nM AKT3 (diluted in 25 mM Hepes, pH 7.0, containing 15 mM MgCl$_2$, 1 mM DTT) and the 0.75 µM Biotinylated Histone H2B and 2 nM ATP-P$^{33}$. The reaction was terminated by addition of 100 µl Stop mix (50 µM ATP, 5 mM EDTA, 0.1% BSA, 0.1% Triton X-100 and 7.5 mg/ml Streptavidin coated PVT SPA beads. After allowing the beads to settle for 30 min, the assay mixture was counted in a microtiterplate scintillation counter.

Example C.3

In Vitro Inhibition of AKT3 using a Filter Assay

In the present AKT3 filter assay, a kinase substrate consisting of a fragment of histone H2B, is incubated with the aforementioned protein in the presence of ($^{33}$P) radio-labeled ATP. The ($^{33}$P)phosporylated substrate binds to a phosphocellulose cation exchange filter, that can easily be removed from the incubation mixture and counted using a microplate scintillation counter.

DETAILED DESCRIPTION

AKT3 filter assays were performed at 25° C. for 3 hrs in the presence of 25 mM Hepes, pH 7.0, containing 15 mM MgCl$_2$, 1 mM DTT Each assay was performed in a 100 µl reaction volume containing 111 nM AKT3 (diluted in 25 mM Hepes, pH 7.0, containing 15 mM MgCl$_2$, 1 mM DTT) and the 2.5 µM Histone H2B and 2 nM ATP-P$^{32}$. The reaction was terminated by addition of 100 µl 75 mM H$_3$PO$_4$, 90 µl of the assay mixture was filtered through Phosphocellulose cation exchange paper. After five times washing with 75 µM H$_3$PO$_4$, the filterpaper was counting in a microtiterplate scintillation counter.

Example C.4

Cellular Inhibition of AKT3 using an ELISA

The human breast adenocarcinoma cell line (MDA-MB 231) was used in an phosphospecific antibody cell ELISA (PACE) to assess the inhibitory effect of the compounds on AKT3 mediated phosphorylation of mitogen-activated protein kinase (MAPK). In the experiments the MDA-MB 231 cells were serum starved for 24 hours (5% CO$_2$; 37° C.). Subsequently, the cells are incubated at room temperature for 2 hours with 20 µM (in serum free medium) of the phosphatidylinositol 3-kinase inhibitor Ly294002 (Alexis, San Diego, Calif.) prior to the incubation for 30 minutes with the compounds at a final concentration ranging from 1 nM to 3 µM. After fixation (with 4.5% formaldehyde) for 20 minutes and washing with PBS (0.1M) the cells were successively incubated with for 5 minutes with 0.1% Triton X-100 in PBS, for 20 minutes with 0.6% H$_2$O$_2$ and 1 hour with a 2% BSA solution as blocking buffer. After overnight incubation with 0.4 µg mouse anti-phospho-MAPK E10 (NEB, # 9106) at 4° C., the phosphorylated MAPK was revealed using 0.5 µg anti mouse IgG HRP (Promega, # W402B) as secondary antibody followed by a 15 minutes incubation using OPD (Sigma, # 8287) as a detection buffer. The OD (490–655 nm) reflected the amount of phosphorylated MAPK and the pIC$_{50}$ of the compounds was based on their effect with respect to blanco (0.1% DMSO) or an internal reference compound treatment.

Example C.5

In Vitro Inhibition of CDC25B using the Fluorogenic Substrate 3-OMFP

CDC25B phosphatase activity is assessed using the fluorogenic substrate 3-O-methyl-flurorescein-phosphate (3-OMFP). The phosphatase-reaction is performed for 1 hour at room temperature in a black microtiter plate in a volume of 50 µl. The reaction mixture contains 4 µg/mlCDC25B, 15 µM (3-OMFP), 15 mM Tris, 50 mM NaCl, 1 mM DTT, 1 mM Na$_2$EDTA at pH 8.0 and 0.1% DMSO solution at 10$^{-5}$ M and the hits are tested in the same conditions in a full dose/response from 10$^{-5}$, 3.10$^{-6}$, 10$^{-6}$ and 3.10$^{-7}$ M. The enzymatic activity is determined by measuring the fluorescent signal at 485 nm (ex.) and 538 (em.).

Example C.6

Cellular Inhibition of AKT3 using an ELISA

The human breast adenocarcinoma cell line (MDA-MB 231) was used in an phosphospecific antibody cell ELISA (PACE) to assess the inhibitory effect of the compounds on AKT3 mediated phosphorylation of mitogen-activated protein kinase (MAPK). In the experiments the MDA-MB 231 cells were serum starved for 24 hours (5% CO$_2$; 37° C.). Subsequently, the cells are incubated at room temperature for 2 hours with 20 µM (in serum free medium) of the phosphatidylinositol 3-kinase inhibitor Ly294002 (Alexis, San Diego, Calif.) prior to the incubation for 30 minutes with the compounds at a final concentration ranging from 1 nM to 3 µM. After fixation (with 4.5% formaldehyde) for 20 minutes and washing with PBS (0.1M) the cells were successively incubated with for 5 minutes with 0.1% Triton X-100 in PBS, for 20 minutes with 0.6% H$_2$O$_2$ and 1 hour with a 2% BSA solution as blocking buffer. After overnight incubation with 0.4 µg mouse anti-phospho-MAPK E10 (NEB, # 9106) at 4° C., the phosphorylated MAPK was revealed using 0.5 µg anti mouse IgG HRP (Promega, # W402B) as secondary antibody followed by a 15 minutes incubation using OPD (Sigma, # 8287) as a detection buffer. The OD (490–655 nm) reflected the amount of phosphorylated MAPK and the pIC$_{50}$ of the compounds was based on their effect with respect to blanco (0.1% DMSO) or an internal reference compound treatment.

| Compound number | CDK4 SPA (Ex. C1): pIC50 values | AKT3 pep. (Ex. C3): pIC50 values | AKT cel (Ex. C6): pIC50 values | Cytotox/survival of A2780 cell after 3 days - pIC50 values | CDC25B WT (Ex. C5): pIC50 values |
|---|---|---|---|---|---|
| 67 | NT | 6.794 | 6.145 | 6.708 | 7.671 |
| 93 | NT | 7.271 | 6.327 | 7.277 | 7.96 |
| 94 | NT | 7.242 | 7.195 | 7.276 | 7.949 |
| 96 | NT | 7.207 | 8.467 | 8.000 | 8.037 |
| 2 | NT | 7.139 | 6.679 | 6.310 | 7.682 |
| 1 | NT | 7.494 | 7.207 | 7.208 | >9 |
| 98 | NT | 6.972 | 6.955 | 6.971 | 7.822 |
| 31 | 6.862 | 7.354 | 6.558 | 7.131 | 7.86 |

-continued

| Compound number | CDK4 SPA (Ex. C1): pIC50 values | AKT3 pep. (Ex. C3): pIC50 values | AKT cel (Ex. C6): pIC50 values | Cytotox/survival of A2780 cell after 3 days - pIC50 values | CDC25B WT (Ex. C5): pIC50 values |
|---|---|---|---|---|---|
| 103 | NT | 7.068 | 7.184 | 7.216 | 7.795 |
| 105 | NT | 6.939 | 7.008 | 7.264 | 7.78 |
| 106 | NT | 7.074 | 6.99 | 7.153 | 7.807 |
| 107 | NT | 7.403 | 7.019 | 7.216 | 7.796 |
| 112 | 6.933 | 7.196 | 6.694 | 6.848 | 7.704 |
| 113 | NT | 7.488 | 7.459 | 7.346 | 7.847 |
| 114 | NT | 7.345 | 6.729 | 6.959 | 7.819 |
| 115 | NT | 7.318 | 7.126 | 7.329 | 7.878 |
| 78 | NT | 7.237 | 6.858 | 7.098 | 7.946 |
| 37 | NT | 7.286 | 7.464 | 7.171 | NT |
| 117 | 6.543 | 7.306 | 6.09 | 6.750 | 7.723 |
| 119 | 6.888 | 7.268 | 6.328 | 7.318 | 7.755 |
| 121 | 6.794 | 7.242 | 6.391 | 6.863 | 7.921 |
| 122 | 7.041 | 7.51 | 6.909 | 7.152 | 7.853 |
| 126 | 7.106 | 7.096 | 6.565 | 5.955 | 7.028 |
| 131 | 7.285 | 7.039 | 7.144 | 7.210 | 7.731 |
| 87 | 7.093 | 7.137 | 7.454 | 7.212 | 7.614 |
| 132 | 7.105 | 7.328 | 7.234 | 7.057 | 7.695 |
| 133 | 6.949 | 7.215 | 7.169 | 6.924 | 7.937 |
| 134 | 6.956 | 7.223 | 7.407 | 7.278 | 7.891 |
| 25 | 7.225 | 7.19 | 6.627 | 7.058 | 7.731 |

D. COMPOSITION EXAMPLES

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

Example D.1

Film-coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

Example D.2

2% Topical Cream

To a solution of hydroxypropyl βcyclodextrin (200 mg) in purified water is added A.I. (20 mg) while stirring. Hydrochloric acid is added until complete dissolution and next sodium hydroxide is added until pH 6.0. While stirring, glycerol (50 mg) and polysorbate 60 (35 mg) are added and the mixture is heated to 70° C. The resulting mixture is added to a mixture of mineral oil (100 mg), stearyl alcohol (20 mg), cetyl alcohol (20 mg), glycerol monostearate (20 mg) and sorbate 60 (15 mg) having a temperature of 70° C. while mixing slowly. After cooling down to below 25° C., the rest of the purified water q.s. ad 1 g is added and the mixture is mixed to homogenous.

The invention claimed is:

1. A Compound having the formula

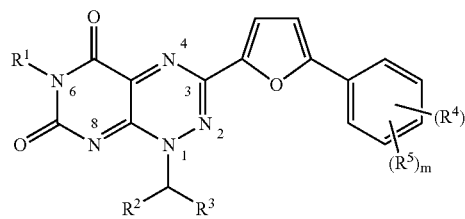

(I)

a N-oxide form, a pharmaceutically acceptable addition salt or a stereochemically isomeric form thereof, wherein:
   m represents an integer being 0 or 1;
   n represents an integer being 0, 1 or 2;

R¹ represents hydrogen, $C_{1-4}$alkyl, hydroxy$C_{1-4}$alkyl, $C_{1-4}$alkyloxycarbonyl or $C_{1-4}$alkyl substituted with phenyl, pyridinyl or morpholinyl,
  phenyl or phenyl substituted with one or where possible more substituents each independently being selected from $C_{1-4}$alkyl, $C_{1-4}$alkyloxycarbonyl, —$NO_2$ or cyano-$C_{1-4}$alkyl,
  piperidinyl or piperidinyl substituted with one or where possible more substituents each independently being selected from $C_{1-4}$alkyl, $C_{1-4}$alkyloxycarbonyl or phenyl-$C_{1-4}$alkyl,
  phenyl-$C_{1-4}$alkyl or $C_{1-4}$alkyloxycarbonyl;
R² represents hydrogen, phenyl, $C_{1-4}$alkyl or $C_{1-4}$alkyl substituted with phenyl or hydroxy;
R³ represents hydrogen, phenyl, $C_{1-4}$alkyl or $C_{1-4}$alkyl substituted with phenyl or hydroxy; or
R² and R³ taken together with the carbon atom to which they are attached form a $C_{3-8}$cycloalkyl or Het¹ wherein said $C_{3-8}$cycloalkyl or Het¹ each independently may optionally be substituted with one, or where possible, two or three substituents each independently selected from $C_{1-4}$alkyloxycarbonyl, phenylcarbonyl $C_{1-4}$alkylsulfonyl, aminosulfonyl, mono- or di($C_{1-4}$alkyl)aminosulfonyl or —C(=NH)—$NH_2$;
R⁴ represents halo, hydroxy, hydroxy$C_{1-4}$alkyl or $C_{1-4}$alkyloxy;
R⁵ represents formyl, $C_{1-4}$alkyl, $C_{1-4}$alkyloxy, Het², —$NO_2$, —$SO_2$-Het⁶, aminosulfonyl, —$SO_2$—$NR^{12}R^{13}$,
  $C_{1-4}$alkyl substituted with one or where possible more substituent being selected from hydroxy, halo, Het³, $NR^6R^7$ or formyl,
  $C_{1-4}$alkyloxy substituted with one or where possible more substituents being selected from Het⁴, $NR^8R^9$ or —C(=O)-Het⁴;
R⁶ and R⁷ are each independently selected from hydrogen, $C_{1-4}$alkyl, -Het⁵, aminosulphonyl, mono- or di($C_{1-4}$alkyl)aminosulfonyl, $C_{1-4}$alkylsulfonyl, $C_{1-4}$alkyloxycarbonyl, $C_{1-4}$alkyloxy$C_{1-4}$alkyl, methoxy$C_{1-4}$alkyl or $C_{1-4}$alkyl substituted with one or where possible more substituents being selected from hydroxy, Het⁵, $C_{1-4}$alkyloxycarbonyl or $C_{1-4}$alkylsulfonyl;
R⁸ and R⁹ are each independently selected from hydrogen, mono- or di($C_{1-4}$alkyl)aminosulphonyl or aminosulphonyl;
R¹² and R¹³ are each independently selected from hydrogen, $C_{1-4}$alkyl, $C_{1-4}$alkyloxy$C_{1-4}$alkyl;
Het¹ represents piperidinyl;
Het² represents a heterocycle selected from piperidinyl, or piperazinyl wherein said monocyclic heterocycles each independently may optionally be substituted with one, or where possible two or three substituents each independently selected from $C_{1-4}$alkyloxycarbonyl;
Het³ represents a heterocycle selected from morpholinyl, pyrrolidinyl, piperidinyl, or piperazinyl wherein said monocyclic heterocycles each independently may optionally be substituted with one, or where possible two or three substituents each independently selected from hydroxy, $C_{1-4}$alkyl, $C_{1-4}$alkyloxycarbonyl, hydroxy$C_{1-4}$alkyl, aminosulfonyl, mono- or di($C_{1-4}$alkyl)aminosulfonyl, $NR^{10}R^{11}$, imidazolyl, tetrahydropyrimidinyl, amino, $NH_2$—$SO_2$—O—, mono- or di($C_{1-4}$alkyl)amino-$SO_2$—O—, $NH_2$—$SO_2$—NH—, mono- or di($C_{1-4}$alkyl)amino-$SO_2$—NH—, hydroxy$C_{1-4}$alkyloxy$C_{1-4}$alkyl, $C_{1-4}$alkyloxy$C_{1-4}$alkyl or $C_{1-4}$alkyloxy;
R¹⁰ and R¹¹ are each independently selected from hydrogen, $C_{1-4}$alkyl, $C_{1-4}$alkyloxycarbonyl, or mono- or di($C_{1-4}$alkyl)aminosulfonyl;
Het⁴ represents a heterocycle selected from morpholinyl, piperidinyl or piperazinyl wherein said monocyclic heterocycles each independently may optionally be substituted with one, or where possible two or three substituents each independently selected from $C_{1-4}$alkyl, aminosulphonyl, mono- or di($C_{1-4}$alkyl)aminosulfonyl or $C_{1-4}$alkyl substituted with one or more hydroxy;
Het⁵ represents a heterocycle selected from pyridinyl, pyrrolidinyl, or piperidinyl wherein said monocyclic heterocycles each independently may optionally be substituted with one, or where possible two or three substituents each independently selected from $C_{1-4}$alkyl, aminosulfonyl, $C_{1-4}$alkyloxycarbonyl or mono- or di($C_{1-4}$alkyl)aminosulfonyl;
Het⁶ represents morpholinyl.

2. A compound according to claim 1 wherein;
m represents an integer being 0 or 1;
n represents an integer being 0, 1 or 2;
R¹ represents $C_{1-4}$alkyl, $C_{1-4}$alkyl substituted with pyridinyl, phenyl, piperidinyl or piperidinyl substituted with $C_{1-4}$alkyloxycarbonyl;
R² represents hydrogen or $C_{1-4}$alkyl;
R³ represents hydrogen or $C_{1-4}$alkyl; or
R² and R³ taken together with the carbon atom to which they are attached form cyclopentyl or piperidinyl wherein said cyclopentyl or piperidinyl each independently may optionally be substituted with one, or where possible, two or three substituents each independently selected from $C_{1-4}$alkyloxycarbonyl, phenylcarbonyl or —C(=NH)—$NH_2$;
R⁴ represents halo or $C_{1-4}$alkyloxy;
R⁵ represents Het², $C_{1-4}$alkyl substituted with one or where possible more substituents being selected from hydroxy, halo, Het³ or $NR^6R^7$, or R⁵ represents $C_{1-4}$alkyloxy substituted with one or where possible more substituents being selected from Het⁴ or —C(=O)-Het⁴;
R⁶ and R⁷ are each independently selected from hydrogen, $C_{1-4}$alkyl, Het⁵ or $C_{1-4}$alkyl substituted with one or where possible more substituents being selected from hydroxy or Het⁵;
Het² represents piperazinyl;
Het³ represents a heterocycle selected from morpholinyl, pyrrolidinyl, piperidinyl, or piperazinyl wherein said monocyclic heterocycles each independently may optionally be substituted with one, or where possible two or three substituents each independently selected from $C_{1-4}$alkyl, aminosulfonyl, mono- or di($C_{1-4}$alkyl)aminosulfonyl, hydroxy$C_{1-4}$alkyloxy$C_{1-4}$alkyl, $C_{1-4}$alkyloxy$C_{1-4}$alkyl or $C_{1-4}$alkyloxy;
Het⁴ represents a heterocycle selected from morpholinyl or piperazinyl wherein said monocyclic heterocycles each independently may optionally be substituted with one, or where possible two or three $C_{1-4}$alkyl substituents;
Het⁵ represents a heterocycle selected from pyridinyl, pyrrolidinyl or piperidinyl wherein said monocyclic heterocycles each independently may optionally be substituted with one, or where possible two or three substituents each independently selected from aminosulfonyl, $C_{1-4}$alkyloxycarbonyl or mono- or di($C_{1-4}$alkyl)aminosulfonyl.

3. A compound according to claim 1 wherein;

m represents an integer being 0 or 1;

n represents an integer being 0, 1 or 2;

$R^1$ represents $C_{1-4}$alkyl, $C_{1-4}$alkyl substituted with phenyl, or $R^1$ represents piperidinyl or piperidinyl substituted with $C_{1-4}$alkyloxycarbonyl;

$R^2$ represents hydrogen, phenyl, $C_4$alkyl or $C_{1-4}$alkyl substituted with phenyl;

$R^3$ represents hydrogen, phenyl, $C_{1-4}$alkyl or $C_{1-4}$alkyl substituted with phenyl; or $R^2$ and $R^3$ taken together with the carbon atom to which they are attached form cyclopentyl or piperidinyl wherein said cyclopentyl or piperidinyl each independently may optionally be substituted with one, or where possible, two or three substituents each independently selected from $C_{1-4}$alkyloxycarbonyl, $C_{1-4}$alkylsulfonyl, mono- or di($C_{1-4}$alkyl)aminosulfonyl or phenylcarbonyl;

$R^4$ represents halo, or $R^4$ represents $C_{1-4}$alkyloxy;

$R^5$ represents formyl, $C_{1-4}$alkyl substituted with one or where possible more substituent being selected from hydroxy, Het$^3$ or $NR^6R^7$, or $R^5$ represents $C_{1-4}$alkyloxy substituted with one or where possible more substituents being selected from Het$^4$ or —C(=O)-Het$^4$;

$R^6$ and $R^7$ are each independently selected from hydrogen, $C_{1-4}$alkyl, -Het$^5$, $C_{1-4}$alkylsulfonyl, methoxy$C_{1-4}$alkyl, or $C_{1-4}$alkyl substituted with one or where possible more substituents being selected from hydroxy or Het$^5$;

Het$^2$ represents piperidinyl optionally substituted with $C_{1-4}$alkyloxycarbonyl;

Het$^3$ represents a heterocycle selected from morpholinyl, pyrrolidinyl, piperidinyl, or piperazinyl wherein said monocyclic heterocycles each independently may optionally be substituted with one, or where possible two or three substituents each independently selected from hydroxy, $C_{1-4}$alkyl, $C_{1-4}$alkyloxycarbonyl, hydroxy$C_{1-4}$alkyl, aminosulfonyl, mono- or di($C_{1-4}$alkyl)aminosulfonyl, $NR^{10}R^{11}$, imidazolyl, tetrahydropyrimidinyl, amino, hydroxy$C_{1-4}$alkyloxy$C_{1-4}$alkyl, $C_{1-4}$alkyloxy$C_{1-4}$alkyl or $C_{1-4}$alkyloxy;

$R^{10}$ and $R^{11}$ are each independently selected from hydrogen or $C_{1-4}$alkyl;

Het$^4$ represents a heterocycle selected from morpholinyl or piperazinyl wherein said monocyclic heterocycles each independently may optionally be substituted with one, or where possible two or three $C_{1-4}$alkyl substituents;

Het$^5$ represents a heterocycle selected from pyridinyl, pyrrolidinyl or piperidinyl wherein said monocyclic heterocycles each independently may optionally be substituted with one, or where possible two or three substituents each independently selected from $C_{1-4}$alkyl, aminosulfonyl, $C_{1-4}$alkyloxycarbonyl or mono- or di($C_{1-4}$alkyl)aminosulfonyl.

4. A compound as claimed in claim 1, wherein $R^2$ and $R^3$ taken together with the carbon atom to which they are attached form a $C_{3-8}$cycloalkyl.

5. A compound as claimed in claim 1, provided that when $R^5$ represents a $C_{1-4}$alkyloxy substituted with Het$^4$, said Het$^4$ is being selected from the group consisting of morpholinyl, piperidinyl, piperazinyl and piperazinyl substituted with one $C_{1-4}$alkyl.

6. A compound as claimed in claim 1, provided that when $R^5$ represents a $C_{1-4}$alkyloxy substituted with —C(=O)-Het$^4$, said Het$^4$ consists of piperazinyl.

7. A pharmaceutical composition comprising a pharmaceutically acceptable carrier and, as active ingredient, an effective kinase inhibitory amount of a compound as described in claim 1.

8. A process of preparing a pharmaceutical composition as defined in claim 7, comprising a pharmaceutically acceptable carrier is intimately mixed with an effective kinase inhibitory amount of a compound as described in claim 1.

9. A process of preparing a compound as described in claim 1, comprising i) reacting a primary amine of formula (V) with an aldehyde of formula (VI);

wherein Q is defined as

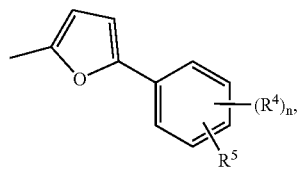

in a condensation reaction using ethanol as a suitable solvent;

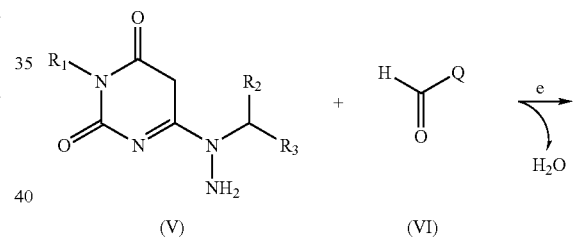

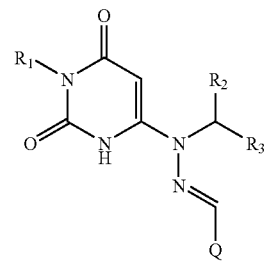

ii) followed by a nitrosative cyclisation of the thus obtained Schiff's bases of formula (II) with NaNO$_2$ in acetic acid, and refluxing the nitroso intermediates of formula (III) in a suitable solvent such as acetic anhydride or ethanol further comprising dithiothreitol (DTT);

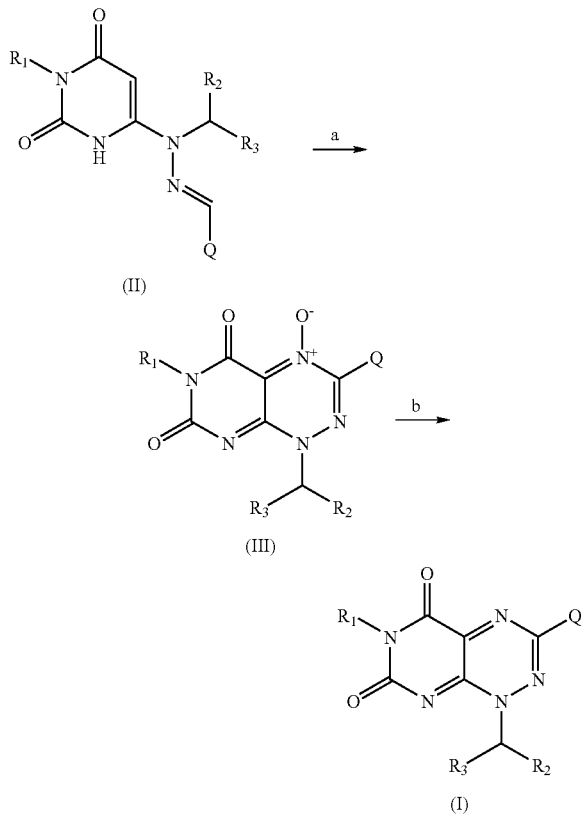

a) NaNO$_2$, AcOH, H$_2$O  b) DTT, EtOH

10. A compound as claimed in claim 2, wherein R$^2$ and R$^3$ taken together with the carbon atom to which they are attached form a C$_{3-8}$cycloalkyl.

11. A compound as claimed in claim 3, wherein R$^2$ and R$^3$ taken together with the carbon atom to which they are attached form a C$_{3-8}$cycloalkyl.

12. A compound as claimed in claim 2, provided that when R$^5$ represents a C$_{1-4}$alkyloxy substituted with Het$^4$, said Het$^4$ is selected from the group consisting of morpholinyl, piperidinyl, piperazinyl and piperazinyl substituted with one C$_{1-4}$alkyl.

13. A compound as claimed in claim 3, provided that when R$^5$ represents a C$_{1-4}$alkyloxy substituted with Het$^4$, said Het$^4$ is selected from the group consisting of morpholinyl, piperidinyl, piperazinyl and piperazinyl substituted with one C$_{1-4}$alkyl.

14. A compound as claimed in claim 4, provided that when R$^5$ represents a C$_{1-4}$alkyloxy substituted with Het$^4$, said Het$^4$ is selected from the group consisting of morpholinyl, piperidinyl, piperazinyl and piperazinyl substituted with one C$_{1-4}$alkyl.

15. A compound as claimed in claim 2, provided that when R$^5$ represents a C$_{1-4}$alkyloxy substituted with —C(=O)-Het$^4$, said Het$^4$ consists of piperazinyl.

16. A compound as claimed in claim 3, provided that when R$^5$ represents a C$_{1-4}$alkyloxy substituted with —C(=O)-Het$^4$, said Het$^4$ consists of piperazinyl.

17. A compound as claimed in claim 4, provided that when R$^5$ represents a C$_{1-4}$alkyloxy substituted with —C(=O)-Het$^4$, said Het$^4$ consists of piperazinyl.

* * * * *